US012727814B2

(12) United States Patent
Thatcher et al.

(10) Patent No.: US 12,727,814 B2
(45) Date of Patent: Sep. 8, 2026

(54) SPECTRAL IMAGING SYSTEMS AND METHODS FOR HISTOLOGICAL ASSESSMENT OF WOUNDS

(71) Applicant: SPECTRAL MD, INC., Dallas, TX (US)

(72) Inventors: Jeffrey E. Thatcher, Irving, TX (US); Wensheng Fan, Plano, TX (US); Kevin Plant, Richardson, TX (US); Faliu Yi, Allen, TX (US)

(73) Assignee: SPECTRAL MD, INC., Dallas, TX (US)

( * ) Notice: Subject to any disclaimer, the term of this patent is extended or adjusted under 35 U.S.C. 154(b) by 748 days.

(21) Appl. No.: 18/152,654

(22) Filed: Jan. 10, 2023

(65) Prior Publication Data

US 2023/0148951 A1 May 18, 2023

Related U.S. Application Data

(63) Continuation of application No. PCT/US2021/041134, filed on Jul. 9, 2021.
(Continued)

(51) Int. Cl.
*A61B 5/00* (2006.01)
*G06T 7/00* (2017.01)

(52) U.S. Cl.
CPC ............ *A61B 5/445* (2013.01); *A61B 5/0075* (2013.01); *A61B 5/4842* (2013.01);
(Continued)

(58) Field of Classification Search
None
See application file for complete search history.

(56) References Cited

U.S. PATENT DOCUMENTS 4,170,987 A 10/1979 Anselmo et al.
4,693,255 A 9/1987 Beall
(Continued)

FOREIGN PATENT DOCUMENTS

CA 2287687 5/2000
CN 1543325 11/2004
(Continued)

OTHER PUBLICATIONS

"MC85 Gangrene", ICD-11 for Mortality and Morbidity Statistics, World Health Organization, webpage accessed Apr. 3, 2024, in 1 page. URL: https://icd.who.int/browse/2024-01/mms/en#188156827.
(Continued)

*Primary Examiner* — Thomas D Lee
(74) *Attorney, Agent, or Firm* — KNOBBE, MARTENS, OLSON & BEAR, LLP

(57) ABSTRACT

The present disclosure relates to systems and methods for assessing or predicting the status of wounds such as burns. Systems can include at least one light detection element and one or more processors configured to receive a signal from the at least one light detection element representing light reflected from a tissue region, generate an image having a plurality of pixels depicting the tissue region, and determine a burn status of a subset of pixels of the image using one or more deep learning algorithms. Systems can further be configured to generate a classified image of the tissue region and/or determine a predictive score associated with healing of the wound.

31 Claims, 39 Drawing Sheets

Related U.S. Application Data

(60) Provisional application No. 63/051,308, filed on Jul. 13, 2020.

(52) U.S. Cl.
CPC .......... *A61B 5/7267* (2013.01); *A61B 5/7275* (2013.01); *G06T 7/0012* (2013.01); *G06T 2207/20084* (2013.01); *G06T 2207/30088* (2013.01); *G06T 2207/30101* (2013.01)

(56) References Cited

U.S. PATENT DOCUMENTS 5,074,306 A 12/1991 Green et al.
5,701,902 A 12/1997 Vari et al.
5,982,497 A 11/1999 Hopkins
6,008,889 A 12/1999 Zeng et al.
6,058,352 A 5/2000 Lu et al.
6,081,612 A 6/2000 Gutkowicz-Krusin et al.
6,352,517 B1 3/2002 Flock et al.
6,353,753 B1 3/2002 Flock et al.
6,381,488 B1 4/2002 Dickey et al.
6,411,907 B1 6/2002 Lu et al.
6,638,668 B2 10/2003 Buchsbaum et al.
6,640,132 B1 10/2003 Freeman et al.
6,889,075 B2 5/2005 Marchitto et al.
7,433,042 B1 10/2008 Cavanaugh et al.
7,612,822 B2 11/2009 Ajito et al.
7,648,808 B2 1/2010 Buchsbaum et al.
7,729,750 B2 6/2010 Tromberg et al.
7,733,389 B2 6/2010 Kurosawa et al.
7,835,002 B2 11/2010 Muhammed et al.
7,860,554 B2 12/2010 Leonardi et al.
8,081,311 B2 12/2011 Themelis
8,233,148 B2 7/2012 Bodkin et al.
8,488,024 B2 7/2013 Yano et al.
8,509,879 B2 8/2013 Dukin et al.
8,583,216 B2 11/2013 Pershing et al.
8,605,172 B2 12/2013 Nikkanen et al.
8,655,433 B2 2/2014 Freeman et al.
8,692,912 B2 4/2014 Fish et al.
8,704,917 B2 4/2014 Rodrigues et al.
8,812,083 B2 8/2014 Papazoglou et al.
8,838,211 B2 9/2014 Melendez et al.
8,892,192 B2 11/2014 Cuccia et al.
9,031,306 B2 5/2015 Parvin et al.
9,078,619 B2 7/2015 Panasyuk et al.
9,295,402 B1 3/2016 Arbab et al.
9,372,118 B1 6/2016 Tablin et al.
9,547,178 B2 1/2017 Erdogan et al.
9,648,254 B2 5/2017 Darty et al.
9,717,417 B2 8/2017 DiMaio et al.
9,766,382 B2 9/2017 Darty
9,962,090 B2 5/2018 DiMaio et al.
9,990,472 B2 6/2018 Gurcan et al.
9,996,925 B2 6/2018 Pedersen et al.
10,066,997 B2 9/2018 Körner et al.
10,198,832 B2 * 2/2019 De Fauw .............. G06F 18/217
10,248,713 B2 4/2019 Pallath et al.
10,740,884 B2 8/2020 McCall et al.
10,750,992 B2 8/2020 Fan et al.
10,783,632 B2 9/2020 Fan et al.
11,182,888 B2 11/2021 McCall et al.
11,195,281 B1 12/2021 Schoess et al.
11,304,604 B2 4/2022 DiMaio et al.
11,337,643 B2 5/2022 Fan et al.
11,599,998 B2 3/2023 Fan et al.
11,631,164 B2 4/2023 McCall et al.
11,948,300 B2 4/2024 Fan et al.
11,989,860 B2 5/2024 McCall et al.
2002/0016533 A1 2/2002 Marchitto et al.
2002/0044691 A1 4/2002 Matsugu
2004/0239923 A1 12/2004 Adams et al.
2005/0025118 A1 2/2005 Hao et al.
2005/0033145 A1 2/2005 Graham et al.
2005/0254704 A1 11/2005 Komiya et al.
2006/0155193 A1 7/2006 Leonardi et al.
2006/0184043 A1 8/2006 Tromberg et al.
2006/0241495 A1 10/2006 Kurtz
2007/0016079 A1 1/2007 Freeman et al.
2007/0024946 A1 2/2007 Panasyuk et al.
2007/0038042 A1 2/2007 Freeman et al.
2007/0179482 A1 8/2007 Anderson
2007/0232930 A1 10/2007 Feeman et al.
2007/0249913 A1 10/2007 Freeman et al.
2008/0194928 A1 8/2008 Bandic et al.
2008/0278602 A1 11/2008 Otsu
2008/0294032 A1 11/2008 Levenson et al.
2009/0072142 A1 3/2009 Blitzer
2009/0118600 A1 5/2009 Ortiz et al.
2009/0118622 A1 5/2009 Dukin et al.
2009/0275808 A1 11/2009 DiMaio et al.
2009/0275841 A1 11/2009 Melendez et al.
2009/0309960 A1 12/2009 Park et al.
2010/0042004 A1 2/2010 Dhawan
2010/0056928 A1 3/2010 Zuzak et al.
2010/0111396 A1 5/2010 Boucheron
2010/0210931 A1 8/2010 Cuccia
2010/0292549 A1 11/2010 Shuler
2011/0117025 A1 5/2011 Dacosta et al.
2011/0124987 A1 5/2011 Papazoglou et al.
2011/0124988 A1 5/2011 Cuccia
2011/0205052 A1 8/2011 Clawson
2012/0078088 A1 3/2012 Whitestone et al.
2012/0141000 A1 6/2012 Jeanne et al.
2012/0172243 A1 7/2012 Davicioni et al.
2012/0190944 A1 7/2012 Thaveeprungsriporn et al.
2012/0195486 A1 8/2012 Kirenko et al.
2012/0200700 A1 8/2012 Bennett et al.
2012/0209095 A1 8/2012 Huiku
2012/0242870 A1 9/2012 Koizumi
2012/0245473 A1 9/2012 Mycek et al.
2012/0288230 A1 11/2012 Pologe et al.
2012/0307056 A1 12/2012 Zuzak et al.
2012/0321759 A1 12/2012 Marinkovich et al.
2013/0021447 A1 1/2013 Brisedoux et al.
2013/0027543 A1 1/2013 Boeykens et al.
2013/0051651 A1 2/2013 Leary et al.
2013/0064441 A1 3/2013 Kask
2013/0137961 A1 5/2013 Barnes et al.
2013/0274612 A1 10/2013 Cuccia et al.
2013/0342670 A1 12/2013 Kyal et al.
2014/0012225 A1 1/2014 Yoo et al.
2014/0092288 A1 4/2014 Hattery et al.
2014/0128744 A1 5/2014 Cuccia et al.
2014/0155757 A1 6/2014 Yang et al.
2014/0155818 A1 6/2014 Salinas et al.
2014/0193050 A1 7/2014 Miller
2014/0193061 A1 7/2014 Miller
2014/0213910 A1 7/2014 Durkin et al.
2014/0257113 A1 9/2014 Panasyuk et al.
2015/0011892 A1 1/2015 Sostek
2015/0025342 A1 1/2015 Papazoglou et al.
2015/0044098 A1 2/2015 Smart et al.
2015/0051498 A1 2/2015 Darty
2015/0080742 A1 3/2015 Andre et al.
2015/0119721 A1 4/2015 Pedersen et al.
2015/0141839 A1 5/2015 Cuccia et al.
2015/0177429 A1 6/2015 Darty
2015/0190061 A1 7/2015 Godavarty et al.
2015/0208923 A1 7/2015 Akl et al.
2015/0223695 A1 8/2015 Chong
2015/0285685 A1 10/2015 Wax et al.
2015/0369664 A1 12/2015 Garsha et al.
2015/0374276 A1 12/2015 Farkas et al.
2015/0374309 A1 12/2015 Farkas et al.
2016/0000395 A1 1/2016 Perumpanani et al.
2016/0033328 A1 2/2016 Walters
2016/0100790 A1 4/2016 Cantu et al.
2016/0245698 A1 8/2016 Pau et al.
2016/0321414 A1 11/2016 Salganicoff et al.
2016/0345888 A1 12/2016 Wu et al.
2016/0349228 A1 12/2016 Kester et al.
2017/0079530 A1 3/2017 DiMaio et al.

(56) References Cited

U.S. PATENT DOCUMENTS

| | | | |
|---|---|---|---|
| 2017/0084024 A1 | 3/2017 | Gurevich | |
| 2017/0135646 A1 | 5/2017 | Chin | |
| 2017/0150903 A1 | 6/2017 | Barnes et al. | |
| 2017/0167980 A1 | 6/2017 | Dimitriadis et al. | |
| 2017/0178322 A1 | 6/2017 | Hakuk et al. | |
| 2017/0223316 A1 | 8/2017 | Zeng et al. | |
| 2017/0262984 A1 | 9/2017 | Barnes et al. | |
| 2017/0272666 A1 | 9/2017 | Darty et al. | |
| 2017/0299435 A1 | 10/2017 | Rhoads et al. | |
| 2017/0319073 A1 | 11/2017 | DiMaio et al. | |
| 2017/0354358 A1 | 12/2017 | Rajab | |
| 2017/0367580 A1 | 12/2017 | DiMaio et al. | |
| 2018/0028079 A1 | 2/2018 | Gurevich et al. | |
| 2018/0061046 A1 | 3/2018 | Bozorgtabar et al. | |
| 2018/0176488 A1 | 6/2018 | Dvir | |
| 2018/0184015 A1 | 6/2018 | Richarte et al. | |
| 2018/0226154 A1 | 8/2018 | Gurcan et al. | |
| 2018/0237783 A1 | 8/2018 | Dallas et al. | |
| 2018/0245978 A1 | 8/2018 | Wang et al. | |
| 2018/0247153 A1 | 8/2018 | Ganapati et al. | |
| 2018/0310828 A1 | 11/2018 | Dimaio et al. | |
| 2019/0038602 A1* | 2/2019 | Granville | A61K 47/32 |
| 2019/0057268 A1 | 2/2019 | Burge et al. | |
| 2019/0082998 A1 | 3/2019 | Nowroozi et al. | |
| 2019/0277753 A1 | 9/2019 | Waxman et al. | |
| 2019/0290117 A1 | 9/2019 | Wang et al. | |
| 2020/0137301 A1 | 4/2020 | Fields et al. | |
| 2020/0138360 A1 | 5/2020 | Fan et al. | |
| 2020/0193580 A1 | 6/2020 | McCall et al. | |
| 2020/0193597 A1* | 6/2020 | Fan | H04N 25/135 |
| 2021/0082094 A1 | 3/2021 | McCall et al. | |
| 2021/0169400 A1 | 6/2021 | Fan et al. | |
| 2021/0201479 A1 | 7/2021 | Fan et al. | |
| 2022/0142484 A1 | 5/2022 | DiMaio et al. | |
| 2022/0156903 A1 | 5/2022 | McCall et al. | |
| 2022/0240783 A1 | 8/2022 | Fan et al. | |
| 2023/0181042 A1 | 6/2023 | Fan et al. | |
| 2023/0206413 A1 | 6/2023 | McCall et al. | |
| 2023/0222654 A1 | 7/2023 | Fan et al. | |
| 2024/0048823 A1 | 2/2024 | Yu et al. | |
| 2024/0281966 A1 | 8/2024 | Fan et al. | |
| 2025/0005761 A1 | 1/2025 | Thatcher et al. | |

FOREIGN PATENT DOCUMENTS

| | | |
|---|---|---|
| CN | 1745294 | 3/2006 |
| CN | 1784185 | 6/2006 |
| CN | 101394782 | 3/2009 |
| CN | 101627902 | 1/2010 |
| CN | 101784227 | 7/2010 |
| CN | 102099671 | 6/2011 |
| CN | 102598683 | 7/2012 |
| CN | 102641126 | 8/2012 |
| CN | 103228205 | 7/2013 |
| CN | 103973957 | 8/2014 |
| CN | 103815875 | 6/2015 |
| CN | 105143448 | 12/2015 |
| CN | 103327894 | 5/2016 |
| CN | 105636512 | 6/2016 |
| CN | 106580328 | 4/2017 |
| CN | 106714670 | 5/2017 |
| CN | 107209934 | 9/2017 |
| CN | 107483774 | 12/2017 |
| CN | 107750345 | 3/2018 |
| CN | 108053482 | 5/2018 |
| CN | 108882896 | 11/2018 |
| EP | 1531629 | 5/2005 |
| EP | 2944930 | 11/2015 |
| EP | 2955496 | 12/2015 |
| JP | H05-505117 | 8/1993 |
| JP | H08-320287 | 12/1996 |
| JP | H10-505768 | 6/1998 |
| JP | 2000-139846 | 5/2000 |
| JP | 2001-503645 | 3/2001 |
| JP | 2005-502895 | 1/2005 |
| JP | 2008-525158 | 7/2008 |
| JP | 2008-283692 | 11/2008 |
| JP | 2010-021614 | 1/2010 |
| JP | 2010-043979 | 2/2010 |
| JP | 2010-503475 | 2/2010 |
| JP | 2011-521237 | 7/2011 |
| JP | 2015-523135 | 8/2015 |
| JP | 2016-540622 | 12/2016 |
| JP | 2017-524935 | 8/2017 |
| JP | 2017-529514 | 10/2017 |
| JP | 2018-036177 | 3/2018 |
| JP | 2018-534965 | 11/2018 |
| JP | 2019-211475 | 12/2019 |
| JP | 2020-046489 | 3/2020 |
| JP | 2022-513486 | 2/2022 |
| RU | 2459574 | 8/2012 |
| TW | 512058 | 12/2002 |
| WO | WO 98/33813 | 8/1998 |
| WO | WO 03/025546 | 3/2003 |
| WO | WO 2004/005895 | 1/2004 |
| WO | WO 2004/012461 | 2/2004 |
| WO | WO 2008/105370 | 9/2008 |
| WO | WO 2009/131989 | 10/2009 |
| WO | WO 2009/140757 | 11/2009 |
| WO | WO 2014/007869 | 1/2014 |
| WO | WO 2014/041543 | 3/2014 |
| WO | WO 2014/125250 | 8/2014 |
| WO | WO 2014/143235 | 9/2014 |
| WO | WO 2015/116823 | 8/2015 |
| WO | WO 2015/185662 | 12/2015 |
| WO | WO 2016/069788 | 5/2016 |
| WO | WO 2016/088483 | 6/2016 |
| WO | WO 2016/153741 | 9/2016 |
| WO | WO 2017/026296 | 2/2017 |
| WO | WO 2017/053609 | 3/2017 |
| WO | WO 2017/074505 | 5/2017 |
| WO | WO 2017/086788 | 5/2017 |
| WO | WO 2017/202535 | 11/2017 |
| WO | WO 2017/223206 | 12/2017 |
| WO | WO 2018/018160 | 2/2018 |
| WO | WO 2018/160963 | 9/2018 |
| WO | WO 2018/217162 A1 | 11/2018 |
| WO | WO 2020/123722 | 6/2020 |
| WO | WO 2020/123724 A1 | 6/2020 |
| WO | WO 2020/123724 A4 | 6/2020 |
| WO | WO 2021/173763 | 9/2021 |
| WO | WO 2021/0202438 | 10/2021 |
| WO | WO 2022/015597 | 1/2022 |
| WO | WO 2022/212413 | 10/2022 |
| WO | WO 2023/141216 | 7/2023 |
| WO | WO 2023/141216 A2 | 7/2023 |
| WO | WO 2023/141216 A9 | 7/2023 |

OTHER PUBLICATIONS

2011 National Burn Repository: Report of Data from 2001-2010. American Burn Association (2011) pp. 134.

Afromowitz et al., "Clinical Evaluation of Burn Injuries Using an Optical Reflectance Technique," IEEE Transactions on Biomedical Engineering, 1987; 34(2):114-27.

Afromowitz et al., "Multispectral imaging of burn wounds: a new clinical instrument for evaluating burn depth". IEEE transactions on bio-medical engineering, 1988; 35(10):842-850.

Aldrich, John, "R. A. Fisher and the Making of Maximum likelihood 1912-1922", Statistical Science, 1997; 12(3):162-176.

Alian et al., "Photoplethysmography," Best Pract. Res. Clin. Anaesthesiol., 2014; 28(4):395-406; ePub Sep. 9, 2014.

Allen, John, "Photoplethysmography and its application in clinical physiological measurement.," Physiol. Meas., 2007; 28:R1-R39.

Anselmo et al., "Multispectral Photographic Analysis—A New Quantitative Tool to Assist in the Early Diagnosis of Thermal Burn Depth." Annals of Biomed Engin. 1977; 5:179-193.

Antonutto et al., "Noninvasive assessment of cardiac output from arterial pressure profiles during exercise," Eur J Appl Physiol. 1995; 72:18-24.

(56) References Cited

OTHER PUBLICATIONS

Arsenault et al., "The Use of Transcutaneous Oximetry to Predict Healing Complications of Lower Limb Amputations: A Systematic Review and Meta-Analysis," Eur J Vasc Endovasc Surg. 2012; 43:329-336.
Badrinarayanan et al., "SegNet: A Deep Convolutional Encoder-Decoder Architecture for Image Segmentation", IEEE Transactions on Pattern Analysis and Machine Intelligence, Oct. 2016, vol. 39, No. 12, pp. 2481-2495.
Badrinarayanan et al., "SegNet: A Deep Convolutional Encoder-Decoder Architecture for Robust Semantic Pixel-Wise Labelling", Computer Science, CVPR 2015, https://arxiv.org/abs/1505.07293, May 2015.
Bajwa et al., "Assessment of Tissue Perfusion in the Lower Limb: Current Methods and Techniques Under Development," Circ Cardiovasc Imag. Sep. 2014; 7:836-843.
Bak et al., "Hemodynamic Changes During Resuscitation After Burns Using the Parkland Formula". J Trauma-Injury Infect Crit Care, 2009; 66(2):329-336.
Baxter, R.D. et al., "Development of a Non-Invasive Imaging Device for Prediction of Diabetic Foot Ulcer Healing Potential", Poster presented at Symposium on Advanced Wound Care, May 7-11, 2019, in 2 pages.
Benitez et al., "Contemporary assessment of foot perfusion in patients with critical limb ischemia," Semin Vasc Surg. Mar. 2014; 27:3-15.
Blanpain et al., "Epidermal homeostasis: A balancing act of stem cells in the skin", Nature Reviews Molecular Cell Biology, Mar. 2009, vol. 10, pp. 207-217.
Branski et al., "A porcine model of full-thickness burn, excision, and skin autografting," Burns 2008; 34(8):1119-1127.
Burgess et al., "Segmental Transcutaneous Measurements of PO2 in Patients Requiring Below-The-Knee Amputation for Peripheral Vascular Insufficiency," J Bone Jt Surg Am 1982; 64:378-82.
Cai, S. et al., "Multi-view distributed video coding using epipolar geometry", Computer Engineering and Applications, 2010, vol. 46(17), pp. 121-124.
Cancio et al., "Burn Support for Operation Iraqi Freedom and related operations, 2003 to 2004", J Burn Care Rehabil. (2005) 26(2): 151-161.
CDC, Diabetes Public Health Resource, "Number (in Thousands) of Hospital Discharges for Non-Traumatic Lower Extremity Amputation with Diabetes as a Listed Diagnosis, United States, 1988-2006," Centers for Disease Control and Prevention, Oct. 20, 2016, Available at: http://www.cdc.gov/diabetes/statistics/lea/fig1.htm; 3 pages.
Cheong et al., "A Review of the Optical Properties of Biological Tissues", IEEE J Quantum Electronics; 1990; 26(12): 2166-2185.
Cortes et al., "Support-Vectors Networks," Machine Learning 1995; 20:273-297.
Cousineau et al., "Outliers detection and treatment: a review," Inter J Psycholog Res. 2010; 3(1):58-67.
Cover et al., "Nearest Neighbor Pattern Classification", IEEE Transactions on Information Theory; 1967; 13(1):21-27.
Cross et al., "Near infrared point and imaging spectroscopy for burn depth assessment", Int'l Congress Series (2005) 1281: 137-142.
Cross et al., "Clinical Utilization of Near-infrared Spectroscopy Devices for burn depth assessment", Wound Rep Reg. (2007) 15: 332-340.
Cuccia et al., "Quantitation and mapping of tissue optical properties using modulated imaging," J Biomed Opt., 2009; 14(2): 1-31.
Desai et al., "Early Burn Wound Excision Significantly Reduces Blood Loss," Ann. Surg. 1990; 211(6):753-762.
Devagn et al., "Modalities for the Assessment of Burn Wound Depth", Journal of Burns and Wounds, Feb. 2006, vol. 5, pp. 7-15.
Dillingham et al., "Reamputation, Mortality, and Health Care Costs Among Persons with Dysvascular Lower-Limb Amputations," Arch Phys Med Rehabil. 2005; 86:480-486.
Downing et al., "Multi-aperture hyperspectral imaging", Applied Industrial Optics: Spectroscopy, Imaging, and Metrology, Jun. 2013, in 3 pages.
Duda et al., *Pattern Classification*, Second Edition, John Wiley & Sons, Nov. 2000.
Eisenbeiss et al., "Reflection-optical multispectral imaging method for objective determination of burn depth," Burns. 1999; 25:697-704.
El Gamal, A. et al., "CMOS Image Sensors: An introduction to the technology, design and performance limits, presenting recent developments and future directions", IEEE Circuits and Devices Magazine, 2005, vol. 21(3), pp. 6-20.
Elmasry et al., "Chapter 1: Principles of Hyperspectral Imaging Technology", *Hyperspectral Imaging for Food Quality Analysis and Control*, Dec. 2010, pp. 3-43.
Eneroth, M., "Factors affecting wound healing after major amputation for vascular disease: a review," Prosth Ortho Internat. 1999; 23:195-208.
Engrav et al., "Early Excision and Grafting vs. Nonoperative Treatment of Burns of Indeterminant Depth: A Randomized Prospective Study," J of Trauma, 1983; 23(11):1001-1004.
Fischer et al., "Multispectral and Hyperspectral imaging technologies in conservation: current research and potential applications," Stud Conserv. 2006; 7: 3-16.
Franklin et al., "Cost of lower-limb amputation in US veterans with diabetes using health services data in fiscal years 2004 and 2010," J Rehabil Res Dev (JRRD) 2014; 51(8):1325-1330.
Garcin et al., "Hair Follicle Bulge Stem Cells Appear Dispensable for the Acute Phase of Wound Re-epithelialization", Stem Cells, Jan. 2016, vol. 34, pp. 1377-1385.
Graham et al., "Wound Healing of Cutaneous Sulfur Mustard Injuries: Strategies for the Development of Improved Therapies," J Burns and Wounds. 2005; 4:1-45.
Grubbs, Frank E., "Procedures for detecting outlying observations in samples", Ballistic Research Laboratories, Aberdeen Proving Ground, 1974; BRL Report No. 1713; 53 pages.
Grubbs, Frank E., "Procedures for Detecting Outlying Observations in Samples", Technometrics, vol. 11(1), Feb. 1969, pp. 1-21.
Guo et al., "Factors Affecting Wound Healing," J Dent Res. 2010; 89(3):219-229.
Gurfinkel et al., "Development of a Novel Animal Burn Model Using Radiant Heat in Rats and Swine," Acad Emerg Med. 2010; 17(5):514-520.
Gurfinkel et al., "Histological assessment of tangentially excised burn eschars," Can J Plast Surg. 2010; 18(3):e33-e36.
Gurtner et al., "Wound repair and regeneration", Nature, May 2008, vol. 453, pp. 314-321.
Guyon et al., "An Introduction to Variables and Feature Selection", J Machine Learn Res. 2003; 3:1157-1182.
HCUP Nationwide Inpatient Sample (NIS)—2009, Healthcare Cost and Utilization Project—HCUP, A Federal-State-Industry Partnership in Health Data Issued May 2011, Updated Nov. 2015, 89 pages, Retrievable at http://www.hcup-us.ahrq.gov; 89 pages.
Haberal et al., "Fluid management in major burn injuries", Indian J. Plast. Surg., Sep. 2010, vol. 43(Suppl), S29-S36.
Heimbach et al., *Surgical management of the burn wound*, Cover and Table of Contents, New York: Raven Press, 1984; TOC only.
Heimbach, David M., "Early Burn Excision and Grafting," Surgical Clinics of North America [Burns], 1987; 67(1):93-107.
Heimbach et al., "Burn depth: A review", World Journal of Surgery, Jan.-Feb. 1992, vol. 16, pp. 10-15.
Heredia-Juesas et al., "Non-Invasive Optical Imaging Techniques for Burn-Injured Tissue Detection for Debridement Surgery," Conf Proc IEEE/EMBS, Aug. 2016; 2893-2896.
Hu et al., "Development of Effective Photoplethysmographic Measurement Techniques: From Contact to Non-Contact and from Point to Imaging." 31st Annual International Conference of the IEEE/EMBS. 2009; 6550-6553.
Huot et al., "Time-resolved multispectral imaging of combustion reaction", Proc. SPIE 9485, Thermosense: Thermal Infrared Applications XXXVII, 94851C, May 2015.

(56) References Cited

OTHER PUBLICATIONS

HyperMed Imaging Inc., FDA-DHHS Reply to 510(k), "Hyperview Hyperspectral Tissue Oxygenation Measurement System" dated Dec. 16, 2016 with enclosures; in 15 pages.
HyperMed Medical Spectral Imaging, Product Overview "HyperView", 2017 in 4 pages.
Imec, "Hyperspectral Imaging", downloaded from https://www.imec-int.com/en/hyperspectral-imaging on Jul. 24, 2018 in 10 pages.
Imms et al., "A high performance biometric signal and image processing method to reveal blood perfusion towards 3D oxygen saturation mapping", Progress Biomed Optics & Imaging [SPIE] (2014) 8947:89470 in 11 pages.
Israel et al., "Variations in Burn Excision and Grafting: A Survey of the American Burn Association", J Burn Care Res. (2017) 38(1): 125-132.
Ioffe et al., "Batch Normalization: Acceleration Deep Network Training by Reducing Internal Covariate Shift", 2015, arXiv:1502.03167v3, https://arxiv.org/abs/1502.03167.
Ito et al., "Stem cells in the hair follicle bulge contribute to wound repair but not to homeostasis of the epidermis", Nature Medicine, Dec. 2005, vol. 11, pp. 1351-1354.
Jackson D. "The diagnosis of the depth of burning." Br J Surg. 1953; 40:588-596.
Jacques et al., "Absorption spectra for biological tissues," ECE532 Biomedical Optics, 1998, Available from: http://omlc.org/education/ece532/class3/muaspectra.html; 1 page.
Jacques, Steven L., "Optical properties of biological tissues: A review", Phys Med. Biol., 2013, 58 (12), R37-61 and Corrigendum 2013 58:5007-5008.
Jaskille et al., "Critical Review of burn depth assessment techniques: Part II. Review of Laser Doppler Technology", J Burn Care Res. (2010) 31(1): 151-157.
Jolivot et al., "Skin Parameter Map Retrieval from a Dedicated Multispectral Imaging System Applied to Dermatology/Cosmetology", International Journal of Biomedical Imaging, Sep. 2013; vol. 3:978289, in 16 pages.
Jones et al., "Snapshot Spectral Imaging Technologies for On-Site Inspection", Presentation given at CTBTO Science and Technology 2015 (SnT2015) Jun. 26, 2015; Vienna, Austria; in 20 pages.
Kaiser et al., "Noninvasive assessment of burn wound severity using optical technology: A review of current and future modalities." Burns. 2011; 37(3): 377-386.
Kauvar et al., "Comparison of Combat and Non-Combat Burns from Ongoing U.S. Military Operations", J Surg Res. (2006) 132(1): 195-200.
Kearns et al., "Disaster planning: The past, present, and future concepts and principles of managing a surge of burn injured patients for those involved in hospital facility planning and preparedness," J Burn Care Res. Jan./Feb. 2014; 35(1):e33-e42.
Kendall et al., "Bayesian SegNet: Model Uncertainty in Deep Convolutional Encoder-Decoder Architectures for Scene Understanding", Oct. 2016, https://arxiv.org/abs/1511.02680.
King, Paul, Book Reviews; "*Design of Pulse Oximeters*," IEEE Eng. Med. Biol. Mag., 1998; p. 117.
King et al., "Surgical wound debridement sequentially characterized in a porcine burn model with multispectral imaging," Burns, 2015; 41:1478-1487.
Kono et al., "Identifying the incidence of and risk factors for reamputation among patients who underwent foot amputation," Ann Vasc Surg 2012; 26:1120-1126.
Lee et al., "Operative wound management," Chapter 13, © 2012 Elsevier Ltd, Inc, BV, DOI: 10.1016/B978-1-4377-2786-9100013-8, pp. 157-172e2.
Li et al., "Review of spectral imaging technology in biomedical engineering: achievements and challenges," J Biomed Optics. 2013; 18(10):100901; 29 pages.
Li et al., "Burn injury diagnostic imaging device's accuracy improved by outlier detection and removal," Proc. of SPIE, vol. 9472, 2015 SPIE, pp. 947206-1 to 947206-11.
Li et al., "Outlier detection and removal improves accuracy of machine learning approach to multispectral burn diagnostic imaging," J. Bio. Optics. Dec. 2015; 20(12):121305-1 to 121305-9.
Lieberman, J.I. et al., National Preparedness: Countermeasures for Thermal Burns. United States Government Accountability Office. GAO-12-304R, Feb. 22, 2012.
Liu et al., "Toward integrating feature selection algorithms for classification and clustering." IEEE Transactions on Knowledge and Data Engineering. 2005. 17(4): 491-502; 35 pages.
Lu et al., "Medical hyperspectral imaging: A review," J Biomed Optics Jan. 2014; 19(1):0101901, 24 pages.
Macri et al., "Immediate burn excision fails to reduce injury progression," J Burn Care Res. 2013; 34(3):153-160.
Marimont et al., "Nearest Neighbor searches and the curse of Dimensionality," J Inst Math Applics 1979; 24 (1): 59-70.
Mertens et al., "Outpatient Burn Management," Nursing Clinics of North America, Burn Mgmt. 1997; 32(2):343-364.
Meyerholz et al., "Morphological Parameters for Assessment of Burn Severity in an Acute Burn Injury Rat Model", International Journal of Experimental Pathology, 2009, vol. 90, pp. 26-33.
Middelkoop et al., "Porcine wound models for skin substitution and burn treatment," Biomaterials. 2004; 25:1559-1567.
Mo et al., "The importance of illumination in a non-contact photoplethysmography imaging system for burn wound assessment", Proc. SPIE 9303 Photonic Therapeutics and Diagnostics XI, 93030M, Feb. 2015; 10 pages.
Mohler, Emile R., "Screening for Peripheral Artery Disease", Circulation, Aug. 2012, vol. 126:e111-e112, in 2 pages.
Monstrey et al., "Assessment of Burn Depth and Burn Wound Healing Potential", Burns, 2008, vol. 34, pp. 761-769.
Mook et al., "Instruments and techniques: Spectrophotometric determination of oxygen saturation of blood independent of the presence of indocyanine green," Cardiovascular Research, 1979; 13:233-237.
Moor Instruments, "Early and Accurate Burn Assessment with Laser Doppler Imaging", Product Brochure; Dec. 2014; 16 pages.
Moza et al., "Deep-Tissue Dynamic Monitoring of Decubitus Ulcers: Wound Care and Assessment," IEEE Eng Med Biol Mag. 2010; 29(2):71-77.
National Limb Loss Information Center, "Fact Sheet: Amputation Statistics by Cause: Limb Loss in the United States," National Limb Loss Information Center, Fact Sheet. Revised 2008, 3 pages.
Nehler et al., "Functional outcome in a contemporary series of major lower extremity amputations," J Vasc Surg. 2003; 38:7-14.
Nguyen et al., "Spatial frequency domain imaging of burn wounds in a preclinical model of graded burn severity." J Biomed Optics. 2013; 18(6): 066010; 8 pages.
Nilsson, Lena M. "Respiration Signals from Photoplethysmography. ," Anesth Analg. 2013; 117(4):859-65.
Norgren et al., Inter-Society Consensus for the Management of Peripheral Arterial Disease (TASC II), J Vasc Surg. 2007; 45(Supp 1):S5A-S67A.
Nouri et al., "Colour and multispectral imaging for wound healing evaluation in the context of a comparative preclinical study", Proc Opt Diagnostics of Living Cells II, (2013) 8669:866923 in 11 pages.
Obermeyer et al., "Predicting the Future—Big Data, Machine Learning, and Clinical Medicine", N Engl J Med. (Sep. 2016) 375(13): 1216-1219.
OPTICS.org—The business of photonics, IMEC Launches TDI, multispectral and hyperspectral sensors; News-Release of Feb. 8, 2017; SPIE Europe in 4 pages.
Orgill, D., "Excision and skin grafting of thermal burns," New Eng J Med. 2011; 360:893-901.
Ortiz-Pujols et al., "Burn care: Are there sufficient providers and facilities?" Chapel Hill, North Carolina. American College of Surgeons Health Policy Research Institute, Nov. 2011; 9:4 pages.
Pan, Z-W et al., "Fast Multispectral Imaging by Spatial Pixel-Binning and Spectral Unmixing", IEEE Transactions on Image Processing, Aug. 2016, vol. 25, No. 8, pp. 3612-3625. doi: 10.1109/TIP.2016.2576401.
Pape et al., "An audit of the use of laser Doppler imaging (LDI) in the assessment of burns of intermediate depth," Burns 2001; 27:233-239.

(56) References Cited

OTHER PUBLICATIONS

Papp et al., "The progression of burn depth in experimental burns: A histological and methodological study", Burns, 2004, vol. 30, pp. 684-690.
Peng et al., "Feature Selection Based on Mutual Information: Criteria of Max-Dependency, Max-Relevance, and Min-Redundancy," IEEE Trans. on Pattern Analysis and Machine Intelligence, 2005; 27(8):1226-1238.
Perkins et al., "GENIE: A Hybrid Genetic Algorithm for Feature Classification in Multi-Spectral Images", in *Applications and science of neural networks, fuzzy systems, and evolutionary computation III*; Inter'l Society of Optics and Photonics (2000) 4120:52-63.
Petricoin et al., "SELDI-TOF-based serum proteomic pattern diagnostics for early detection of cancer", Curr Opin Biotechnol. (2004) 15(1): 24-30.
Regensteiner et al, "The impact of peripheral arterial disease on health-related quality of life in the Peripheral Arterial Disease Awareness, Risk, and Treatment: New Resources for Survival (PARTNERS) Program", Vascular Medicine, Feb. 2008, vol. 13:15-24.
Reisner et al., "Utility of the Photoplethysmogram in Circulatory Monitoring", Anesthesiol. 2008; 108:950-958.
Resch et al., "Estimation of burn depth at burn centers in the United States: a survey." J Burn Care Res. Nov./Dec. 2014; 35: 491-497.
Resurge International, "Burns: The Neglected but Solvable Health Crisis" from Reconstructive Surgery for the World's Poor since 1969; accessed <http://www.resurge.org/transforming_lives/story_burns.cfm> Accessed Feb. 9, 2015; 3 pages.
Rittie, L., "Cellular mechanisms of skin repair in humans and other mammals", Journal of Cell Communication and Signaling, 2016, vol. 10, pp. 103-120.
Rogers et al., "The right to bear legs—An amendment to healthcare: how preventing amputations can save billions for the US health-care system," J Am Podiatr Med Assoc 2008; 98:166-168.
Rousseeuw, Peter J. "Least Median of Squares Regression". J Am Stat Assoc. 1984; 79(388):871-880.
Rowan et al., "Burn wound healing and treatment: review and advancements", Critical Care, 2015, vol. 19, in 12 pages.
Severinghaus et al., "History of Blood Gas Analysis. VII. Pulse Oximetry." J Clin Monitor. 1987; 3(2):135-138.
Sheng et al., "BurnCalc assessment study of computer-aided individual three-dimensional burn area calculation", Journal of Translational Medicine, Sep. 2014, vol. 12, p. 242, in 12 pages.
Siew, Ronian [Ed.], Multiple-Field Multispectral Imaging Using Wide-Angle Lenses, Inopticalsolutions Notebook Series (2018); Chapter 1, pp. 1-12.
Robnik-Sikonja et al., "Evaluation of prognostic factors and prediction of chronic wound healing rate by machine learning tools", Artificial Intelligence in Medicine, Jan. 2003, in 10 pages. URL: http://lkm.fri.uni-lj.si/rmarko/papers/robnik01-aime.pdf.
Singer et al., "A porcine burn model," Meth Mol Med. 2003; 78:107-119.
Singer et al., "Standardized Burn Model Using a Multiparametric Histologic Analysis of Burn Depth", Academic Emergency Medicine, Jan. 2000, vol. 7, pp. 1-6.
Sokolova et al., "A systematic analysis of performance measures for classification tasks." Info Proc Manag. 2009; 45: 427-437.
Sowa et al., "Near infrared spectroscopic assessment of hemodynamic changes in the early post-burn period", Burns (2001) 27: 241-249.
Sowa et al., "Classification of burn injuries using near-infrared spectroscopy", J Biomed Optics. (Sep. 2006) 11(5): 6 pages.
Spectral MD, Inc., "DeepView Digital Video Physiological Portable Imaging System", FDA Traditional 510(k) Application as filed Dec. 28, 2012; 528 pages.
Spigulis et al., "A Device for Multimodal Imaging of Skin", Multimodal Biomedical Imaging VIII, Proc. SPIE, vol. 8574, p. 85740J, Feb. 2013, in 7 pages.
Squiers et al., "Multispectral imaging burn wound tissue classification system: a comparison of test accuracies between several common machine learning algorithms," Proc. of SPIE, 2016; 9785:97853L-1 to 97853L-10.
Steinberg et al., "Sample size for positive and negative predictive value in diagnostic research using case-control designs", Biostatistics, vol. 10, No. 1, pp. 94-105, 2009.
Takeo et al., "Wound Healing and Skin Regeneration", Cold Spring Harbor Perspectives Medicine, 2015, vol. 5, in 13 pages.
Thatcher et al., "Dynamic tissue phantoms and their use in assessment of a noninvasive optical plethysmography imaging device," SPIE Sensing Technology + Applications, May 2014; 910718, 18 pages.
Thatcher et al., "Imaging Techniques for Clinical Burn Assessment with a Focus on Multispectral Imaging," Advan Wound Care, Mar. 2016; 5(8):360-378.
Thatcher et al., "Multispectral and Photophlethysmography Optical Imaging Techniques Identify Important Tissue Characteristics in an Animal Model of Tangential Burn Excision," J Burn Care & Res., Jan./Feb. 2016, 37(1):38-52.
Themelis et al., "Multispectral Imaging Using Multiple-bandpass filters", Opt Lett., May 2008; 33(9):1023-1025.
Tiwari, V.K., "Burn wound: How it differs from other wounds?" Indian Journal of Plastic Surgery, May-Aug. 2012, vol. 45, pp. 364-373.
Li et al., "Simultaneous measurement of deep tissue blood flow and oxygenation using noncontact diffuse correlation spectroscopy flow-oximeter", Scientific Reports, Feb. 2013, 3:1358, pp. 1-10.
Tuchin, Valery V., "Light-Tissue Interactions", Biomedical Photonics Handbook, CRC Press, Boca Raton, Florida 2003; Chapter 3; pp. 123-167.
Usman et al., "Second Derivative of Photoplethysmogram in Estimating Vascular Aging Among Diabetic Patients," in Internet Conf for Technical Postgraduates 2009, TECHPOS 2009, 3 pages.
Vemulapalli et al., "Peripheral arterial testing before lower extremity amputation among Medicare beneficiaries, 2000 to 2010," Circ Cardiovasc Qual Outcomes, Jan. 2014, 7:142-150.
Vogel et al., "Using Non-Invasive Multi-Spectral Imaging to Quantitatively Assess Tissue Vasculature", J Biomed Optics (2007) 12(5): 051604 in 32 pages.
Wang et al., "A Unified Framework for Automatic Wound Segmentation and Analysis with Deep Convolutional Neural Networks", 2015 37th Annual International Conference of the IEEE Engineering in Medicine and Biology Society (EMBC), Aug. 2015, pp. 2415-2418.
Waters et al., "Energy cost of walking of amputees: the influence of level of amputation," J Bone Joint Surg. 1975; 58(1):42-46.
Watts et al., "Burn depth and its histological measurement," Burns 27 (2001) 154-160.
Webb, Steve [Ed.], *The physics of medical imaging*, © 1988, IOP Publishing Ltd., TOC only.
Webster, J.G. [Ed.], *Design of Pulse Oximeters*, Medical Science Series, © IOP Publishing Ltd. 1997; TOC only.
Worsley et al., "Back to basics: biophysical methods in tissue viability research," (Draft); J Wound Care, 2013; 22(8):434-439.
Wütschert et al., "Determination of Amputation Level in Ischemic Limbs—Reappraisal of the measurement of $TcPo_2$", Diabetes Care, 1997; 20(8):1315-1318.
Xie et al., "Skin appendage-derived stem cells: cell biology and potential for wound repair", Burns and Trauma, 2016, vol. 4(38), in 6 pages.
Ziegler-Graham et al., "Estimating the Prevalence of Limb Loss in the United States: 2005 to 2050," Arch Phys Med Rehabil. 2008; 89:422-429.
Zonios et al., "Skin melanin, hemoglobin, and light scattering properties can be quantitatively assessed in vivo using diffuse reflectance spectroscopy", J Invest Dermatol. (2001) 117(6): 1452-1457.
International Search Report and Written Opinion dated Oct. 13, 2021 for PCT/US2021/041134.

(56) References Cited

OTHER PUBLICATIONS

Goyal, M. et al., "Fully convolutional networks for diabetic foot ulcer segmentation", 2017 IEEE International Conference on Systems, Man, and Cybernetics (SMC), 2017, pp. 618-623. doi: 10.1109/SMC.2017.8122675.

Mukherjee, R. et al., "Diagnostic and Prognostic Utility of Non-Invasive Multimodal Imaging in Chronic Wound Monitoring: a Systemic Review", Journal of Medical Systems, Feb. 2017, vol. 41, No. 3, in 17 pages.

Scholz, I., "Reconstruction and Modeling of Static and Dynamic Light Fields", University of Erlangen-Nürnberg, Jan. 2008, pp. 1-268. URL: https://citeseerx.ist.psu.edu/viewdoc/download?doi=10.1.1.643.3427&rep=rep1&type=pdf.

Yang, Q. et al., "Investigation of the Performance of Hyperspectral Imaging by Principal Component Analysis in the Prediction of Healing of Diabetic Foot Ulcers", Journal of Imaging, Dec. 2018, vol. 4, No. 12, in 11 pages.

* cited by examiner

SECTION C-C

SPECTRAL IMAGING SYSTEMS AND METHODS FOR HISTOLOGICAL ASSESSMENT OF WOUNDS

CROSS-REFERENCE TO RELATED APPLICATIONS

This application is a continuation of International Application No. PCT/US2021/041134, filed Jul. 9, 2021, titled "SPECTRAL IMAGING SYSTEMS AND METHODS FOR HISTOLOGICAL ASSESSMENT OF WOUNDS," which claims the benefit of U.S. Provisional Application Ser. No. 63/051,308, filed Jul. 13, 2020, both of which are hereby expressly incorporated by reference in their entirety and for all purposes.

STATEMENT REGARDING FEDERALLY SPONSORED R&D

Some of the work described in this disclosure was made with United States Government support under Contract No. HHSO100201300022C, awarded by the Biomedical Advanced Research and Development Authority (BARDA), within the Office of the Assistant Secretary for Preparedness and Response in the U.S. Department of Health and Human Services. Some of the work described in this disclosure was made with United Government support under Contract Nos. W81XWH-17-C-0170 and/or W81XWH-18-C-0114, awarded by the U.S. Defense Health Agency (DHA). The United States Government may have certain rights in this invention.

TECHNICAL FIELD

The systems and methods disclosed herein are directed to spectral imaging, and, more particularly, to systems and methods for histological assessment of wounds based on spectral imaging.

BACKGROUND

The electromagnetic spectrum is the range of wavelengths or frequencies over which electromagnetic radiation (e.g., light) extends. In order from longer wavelengths to shorter wavelengths, the electromagnetic spectrum includes radio waves, microwaves, infrared (IR) light, visible light (that is, light that is detectable by the structures of the human eye), ultraviolet (UV) light, x-rays, and gamma rays. Spectral imaging refers to a branch of spectroscopy and photography in which some spectral information or a complete spectrum is collected at locations in an image plane. Multispectral imaging systems can capture multiple spectral bands (on the order of a dozen or less and typically at discrete spectral regions), for which spectral band measurements are collected at each pixel, and can refer to bandwidths of about tens of nanometers per spectral channel. Hyperspectral imaging systems measure a greater number of spectral bands, for example as many as 200 or more, with some providing a continuous sampling of narrow bands (e.g., spectral bandwidths on the order of nanometers or less) along a portion of the electromagnetic spectrum.

SUMMARY

The multispectral imaging systems and techniques disclosed herein have several features, no single one of which is solely responsible for its desirable attributes. Without limiting the scope as expressed by the claims that follow, certain features of the disclosed spectral imaging will now be discussed briefly. One skilled in the art will understand how the features of the disclosed spectral imaging provide several advantages over traditional systems and methods.

In a first aspect, a system for assessing or predicting wound status comprises at least one light detection element configured to collect light of at least a first wavelength after being reflected from a tissue region comprising a burn; and one or more processors in communication with the at least one light detection element and configured to: receive a signal from the at least one light detection element, the signal representing light of the first wavelength reflected from the tissue region; generate, based on the signal, an image having a plurality of pixels depicting the tissue region; determine, based on the signal, a reflectance intensity value at the first wavelength for each pixel of at least a subset of the plurality of pixels; determine, using at least one deep learning (DL) algorithm, a burn status corresponding to each pixel of the subset of pixels depicting the tissue region; and generate a classified image based at least in part on the image and the determined burn status corresponding to each pixel of the subset of pixels depicting the tissue region.

In some embodiments, the classified image comprises pixels having different visual representations based on the burn status corresponding to each pixel.

In some embodiments, the one or more processors are further configured to cause a visual display of the classified image.

In some embodiments, the burn status corresponding to each pixel is selected from a non-healing burn status and a healing burn status.

In some embodiments, the burn status corresponding to each pixel is a status associated with burn depth. In some embodiments, the burn status corresponding to each pixel is selected from a first degree burn status, a superficial second degree burn status, a deep second degree burn status, and a third degree burn status.

In some embodiments, the burn status corresponds to necrosis of adnexal structures within at least a portion of the burn. In some embodiments, determining the burn status corresponding to each pixel of the subset of pixels depicting the tissue region comprises identifying a percentage of necrotic adnexal structures within the at least a portion of the burn. In some embodiments, a non-healing burn status corresponds to necrosis of greater than 50.0% of the adnexal structures. In some embodiments, a non-healing burn status corresponds to necrosis of greater than 0.0% of the adnexal structures.

In some embodiments, the at least one DL algorithm comprises a convolutional neural network. In some embodiments, the convolutional neural network comprises a SegNet.

In some embodiments, the at least one DL algorithm comprises an ensemble of a plurality of DL algorithms. In some embodiments, the at least one DL algorithm comprises a weighted averaging ensemble. In some embodiments, the at least one DL algorithm comprises a TPR ensemble.

In some embodiments, the at least one DL algorithm is trained using a wound database. In some embodiments, the wound database comprises a burn database.

In some embodiments, the at least one DL algorithm is trained based at least in part on a plurality of ground truth masks, wherein at least some of the ground truth masks are generated based at least in part on the presence of necrotic adnexal structures in burn tissue biopsies.

In some embodiments, the one or more processors are further configured to determine, based at least in part on the burn status corresponding to each pixel of the subset of pixels depicting the tissue region, a predictive score associated with healing of the burn over a predetermined time interval following generation of the image. In some embodiments, the predictive score corresponds to a probability of healing without surgery or skin grafting. In some embodiments, the predetermined time interval is 21 days.

In a second aspect, a method of detecting cellular viability or damage, collagen denaturation, damage to adnexal structures or adnexal structure necrosis and/or damage to blood vessels of a subject after a wound, preferably a burn comprises selecting a subject having a wound, preferably a burn; imaging a region of the wound, preferably a burn, using the multispectral image system of any one of the preceding aspects; evaluating the image data using a DL algorithm trained with a wound, preferably a burn, database; displaying whether cells of the wound are viable or damaged, collagen is denatured, adnexal structures are damaged or necrotic and/or blood vessels are damaged within the imaged region of the wound, preferably a burn; and optionally, providing a predictive score for healing of the wound, preferably a burn, over a set time period, preferably 21-30 days, without advanced care such as surgery or skin grafting.

In some embodiments, the damaged adnexal structures evaluated comprise hair follicles, sebaceous glands, apocrine glands and/or eccrine sweat glands.

In some embodiments, the cell viability or damage, collagen denaturation, damage to adnexal structures or adnexal structure necrosis and/or damage to blood vessels of the subject are evaluated in the papillary region of the skin.

In some embodiments, the cell viability or damage, collagen denaturation, damage to adnexal structures or adnexal structure necrosis and/or damage to blood vessels of the subject are evaluated in the reticular dermis of the skin.

In some embodiments, the cell viability or damage, collagen denaturation, damage to adnexal structures or adnexal structure necrosis and/or damage to blood vessels of the subject are evaluated deeper than the reticular dermis of the skin.

In some embodiments, hyalinized collagen or lack of detectable individual collagen fibers is detected.

In some embodiments, the cellular damage is cell swelling, cytoplasmic vacuolization, or nuclear pyknosis.

In some embodiments, when 50% or greater of the adnexual structures analyzed is identified as being damaged or necrotic, a predictive score of non-healing burn is provided and, optionally said subject is provided guidance to receive advanced care such as skin grafting or surgery or said subject is provided skin grafting or surgery.

In some embodiments, the DL algorithm was trained using stochastic gradient descent with a momentum optimizer and cross-entropy loss.

In some embodiments, the DL algorithm is selected from SegNet, SegNet with filter-bank regularization, SegNet with auxiliary loss, U-Net, Dilated fully connected neural network (dFCN), Averaging Ensemble, TPR-ensemble, or Weighted Averaging Ensemble. In some embodiments, the DL algorithm is SegNet.

DETAILED DESCRIPTION

Figure 1A:
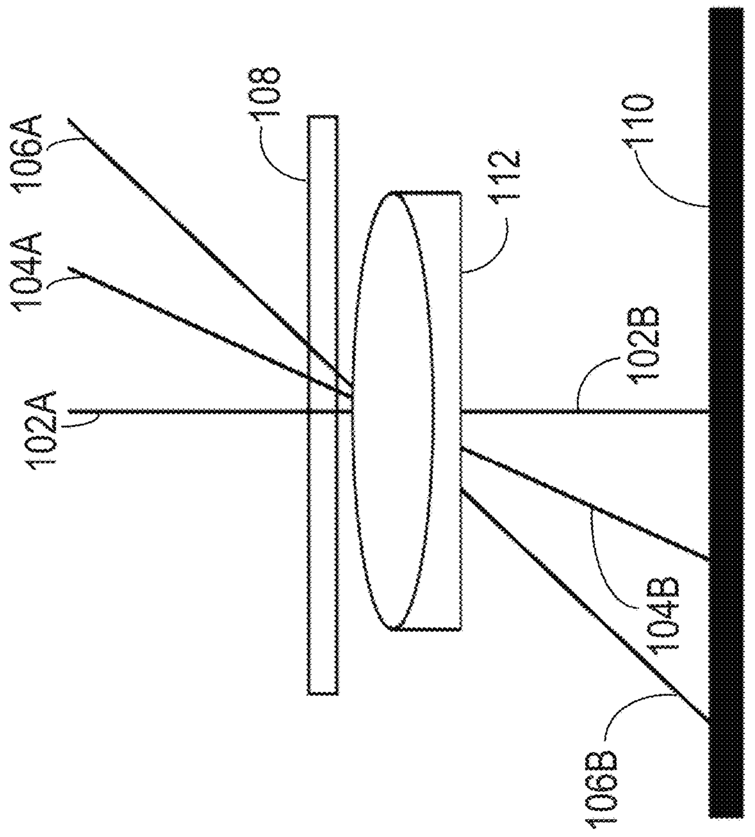
FIG. 1A illustrates an example of light incident on a filter at different chief ray angles.

Generally described, the present disclosure relates to spectral imaging using a multi-aperture system with curved multi-bandpass filters positioned over each aperture. The present disclosure further relates to techniques for implementing spectral unmixing and image registration to generate a spectral datacube using image information received from such imaging systems. The disclosed technology addresses a number of challenges that are typically present in spectral imaging, described below, in order to yield image data that represents precise information about wavelength bands that were reflected from an imaged object. In some embodiments, the systems and methods described herein acquire images from a wide area of tissue (e.g., 5.9×7.9 inches) in a short amount of time (e.g., within 6 seconds or less) and can do so without requiring the injection of imaging contrast agents. In some aspects, for example, the multispectral image system described herein is configured to acquire images from a wide area of tissue, e.g., 5.9×7.9 inches, within 6 seconds or less and, wherein said multispectral image system is also configured to provide tissue analysis information, such as identification of a plurality of burn states, wound states, healing potential, a clinical characteristic including a cancerous or non-cancerous state of the imaged tissue, wound depth, a margin for debridement, or the presence of a diabetic, non-diabetic, or chronic ulcer in the absence of imaging contrast agents. Similarly, in some of the methods described herein, the multispectral image system acquires images from a wide area of tissue, e.g., 5.9×7.9 inches, within 6 seconds or less and said multispectral image system outputs tissue analysis information, such as identification of a plurality of burn states, wound states, healing potential, a clinical characteristic including a cancerous or non-cancerous state of the imaged tissue, wound depth, a margin for debridement, or the presence of a diabetic, non-diabetic, or chronic ulcer in the absence of imaging contrast agents.

One such challenge in existing solutions is that captured images can suffer from color distortions that compromise the quality of the image data. This can be particularly problematic for applications that depend upon precise detection and analysis of certain wavelengths of light using optical filters. Specifically, color shading is a position dependent variation in the wavelength of light across the area of the image sensor, due to the fact that transmittance of a color filter shifts to shorter wavelengths as the angle of light incident on the filter increases. Typically, this effect is observed in interference-based filters, which are manufactured through the deposition of thin layers with varying refractive indices onto a transparent substrate. Accordingly, longer wavelengths (such as red light) can be blocked more at the edges of the image sensor due to larger incident light ray angles, resulting in the same incoming wavelength of light being detected as a spatially non-uniform color across the image sensor. If left uncorrected, color shading manifests as shift in color near the edges of the captured image.

The technology of the present disclosure provides advantages relative to other multi-spectral imaging systems on the market because it is not restrictive in the configuration of lens and/or image sensors and their respective fields of view or aperture sizes. It will be understood that changes to lenses, image sensors, aperture sizes, or other components of the presently disclosed imaging systems may involve other adjustments to the imaging system as would be known to those of ordinary skill in the art. The technology of the present disclosure also provides improvements over other multi-spectral imaging systems in that the components that perform the function of resolving wavelengths or causing the system as a whole to be able to resolve wavelengths (e.g., optical filters or the like) can be separable from the components that transduce light energy into digital outputs (e.g., image sensors or the like). This reduces the cost, complexity, and/or development time to re-configure imaging systems for different multi-spectral wavelengths. The technology of the present disclosure may be more robust than other multi-spectral imaging systems in that it can accomplish the same imaging characteristics as other multi-spectral imaging systems on the market in a smaller and lighter form factor. The technology of the present disclosure is also advantageous relative to other multi-spectral imaging systems in that it can acquire multi-spectral images in a snapshot, video rate, or high speed video rate. The technology of the present disclosure also provides a more robust implementation of multi-spectral imaging systems based on multi-aperture technology as the ability to multiplex several spectral bands into each aperture reduces the number of apertures necessary to acquire any particular number of spectral bands in an imaging data set, thus reducing costs through a reduced number of apertures and improved light collection (e.g., as larger apertures may be used within the fixed size and dimensions of commercially available sensor arrays). Finally, the technology of the present disclosure can provide all of these advantages without a trade-off with respect to resolution or image quality.

Figure 1B:
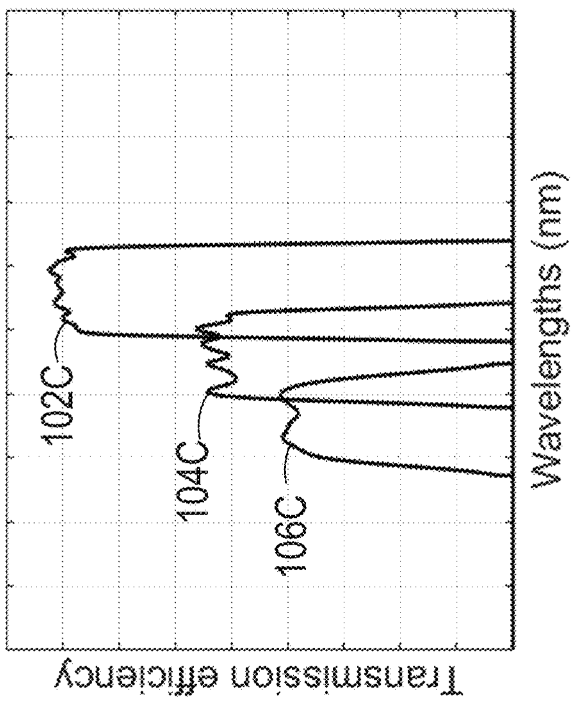
FIG. 1B is a graph illustrating example transmission efficiencies provided by the filter of FIG. 1A for various chief ray angles.

FIG. 1A illustrates an example of a filter 108 positioned along the path of light towards an image sensor 110, and also illustrates light incident on the filter 108 at different ray angles. The rays 102A, 104A, 106A are represented as lines which, after passing through the filter 108, are refracted onto the sensor 110 by a lens 112, which may also be substituted with any other image-forming optics, including but not limited to a mirror and/or an aperture. The light for each ray is presumed in FIG. 1A to be broadband, for example, having a spectral composition extending over a large wavelength range to be selectively filtered by filter 108. The three rays 102A, 104A, 106A each arrive at the filter 108 at a different angle. For illustrative purposes, light ray 102A is shown as being incident substantially normal to filter 108, light ray 104A has a greater angle of incidence than light ray 102A, and light ray 106A has a greater angle of incidence than light ray 104A. The resulting filtered rays 102B, 104B, 106B exhibit a unique spectrum due to the angular dependence of the transmittance properties of the filter 108 as seen by the sensor 110. The effect of this dependence causes a shift in the bandpass of the filter 108 towards shorter wavelengths as the angle of incidence increases. Additionally, the dependence may cause a reduction in the transmission efficiency of the filter 108 and an altering of the spectral shape of the bandpass of the filter 108. These combined effects are referred to as the angular-dependent spectral transmission. FIG. 1B depicts the spectrum of each light ray in FIG. 1A as seen by a hypothetical spectrometer at the location of sensor 110 to illustrate the shifting of the spectral bandpass of filter 108 in response to increasing angle of incidence. The curves 102C, 104C, and 106C demonstrate the shortening of the center wavelength of the bandpass; hence, the shortening of the wavelengths of light passed by the optical system in the example. Also shown, the shape of the bandpass and the peak transmission are altered due to the angle incidence as well. For certain consumer applications, image processing can be applied to remove the visible effects of this angular-dependent spectral transmission. However, these post-processing techniques do not allow for recovery of precise information regarding which wavelength of light was actually incident upon the filter 108. Accordingly, the resulting image data may be unusable for certain high-precision applications.

Figure 2A:
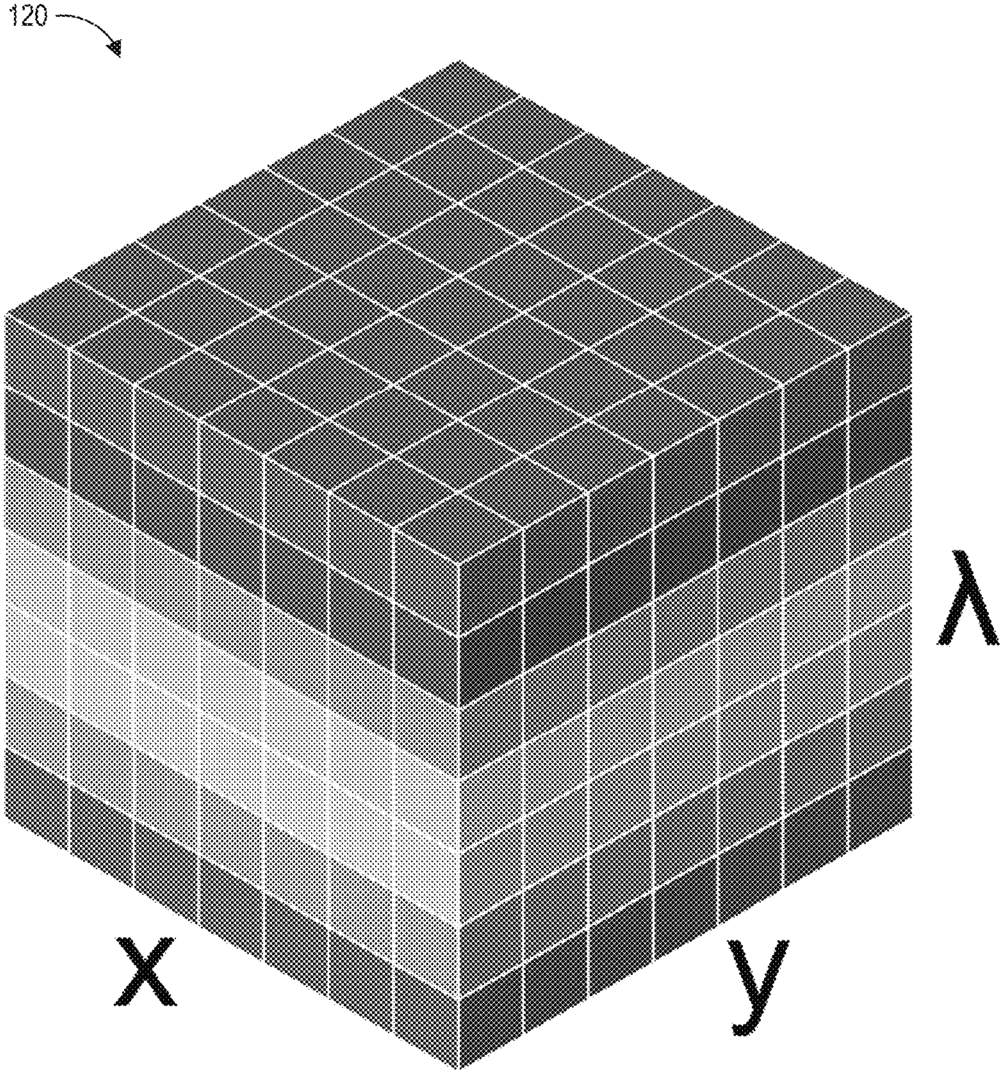
FIG. 2A illustrates an example of a multispectral image datacube.

Another challenge faced by certain existing spectral imaging systems is the time required for capture of a complete set of spectral image data, as discussed in connection with FIGS. 2A and 2B. Spectral imaging sensors sample the spectral irradiance $I(x,y,\lambda)$ of a scene and thus collect a three-dimensional (3D) dataset typically called a datacube. FIG. 2A illustrates an example of a spectral image datacube 120. As illustrated, the datacube 120 represents three dimensions of image data: two spatial dimensions (x and y) corresponding to the two-dimensional (2D) surface of the image sensor, and a spectral dimension (λ) corresponding to a particular wavelength band. The dimensions of the datacube 120 can be given by $N_xN_yN_\lambda$, where $N_x$, $N_y$, and $N_\lambda$ are the number of sample elements along the (x, y) spatial dimensions and spectral axes λ, respectively. Because datacubes are of a higher dimensionality than 2D detector arrays (e.g., image sensors) that are currently available, typical spectral imaging systems either capture time-sequential 2D slices, or planes, of the datacube 120 (referred to herein as "scanning" imaging systems), or simultaneously measure all elements of the datacube by dividing it into multiple 2D elements that can be recombined into datacube 120 in processing (referred to herein as "snapshot" imaging systems).

Figure 2B:
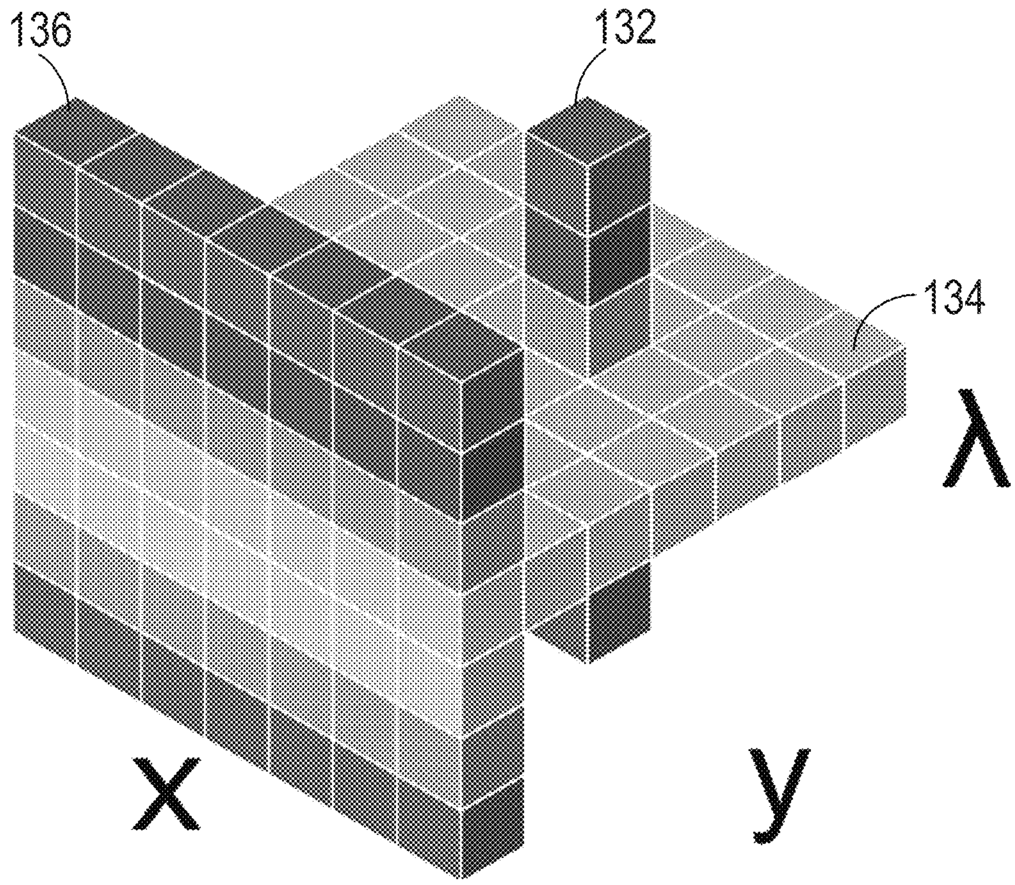
FIG. 2B illustrates examples of how certain multispectral imaging technologies generate the datacube of FIG. 2A.

FIG. 2B illustrates examples of how certain scanning spectral imaging technologies generate the datacube 120. Specifically, FIG. 2B illustrates the portions 132, 134, and 136 of the datacube 120 that can be collected during a single detector integration period. A point scanning spectrometer, for example, can capture a portion 132 that extends across all spectral planes/at a single (x, y) spatial position. A point scanning spectrometer can be used to build the datacube 120 by performing a number of integrations corresponding to each (x, y) position across the spatial dimensions. A filter wheel imaging system, for example, can capture a portion 134 that extends across the entirety of both spatial dimensions x and y, but only a single spectral plane λ. A wavelength scanning imaging system, such as a filter wheel imaging system, can be used to build the datacube 120 by performing a number of integrations corresponding to the number of spectral planes λ. A line scanning spectrometer, for example, can capture a portion 136 that extends across all spectral dimensions 2 and all of one of the spatial dimension (x or y), but only a single point along the other spatial dimension (y or x). A line scanning spectrometer can be used to build the datacube 120 by performing a number of integrations corresponding to each position of this other spatial dimension (y or x).

For applications in which the target object and imaging system are both motionless (or remain relatively still over the exposure times), such scanning imaging systems provide the benefit of yielding a high resolution datacube 120. For line scanning and wavelength scanning imaging systems, this can be due to the fact that each spectral or spatial image is captured using the entire area of the image sensor. However, movement of the imaging system and/or object between exposures can cause artifacts in the resulting image data. For example, the same (x, y) position in the datacube 120 can actually represent a different physical location on the imaged object across the spectral dimension λ. This can lead to errors in downstream analysis and/or impose an additional requirement for performing registration (e.g., aligning the spectral dimension λ so that a particular (x, y) position corresponds to the same physical location on the object).

Figure 2C:
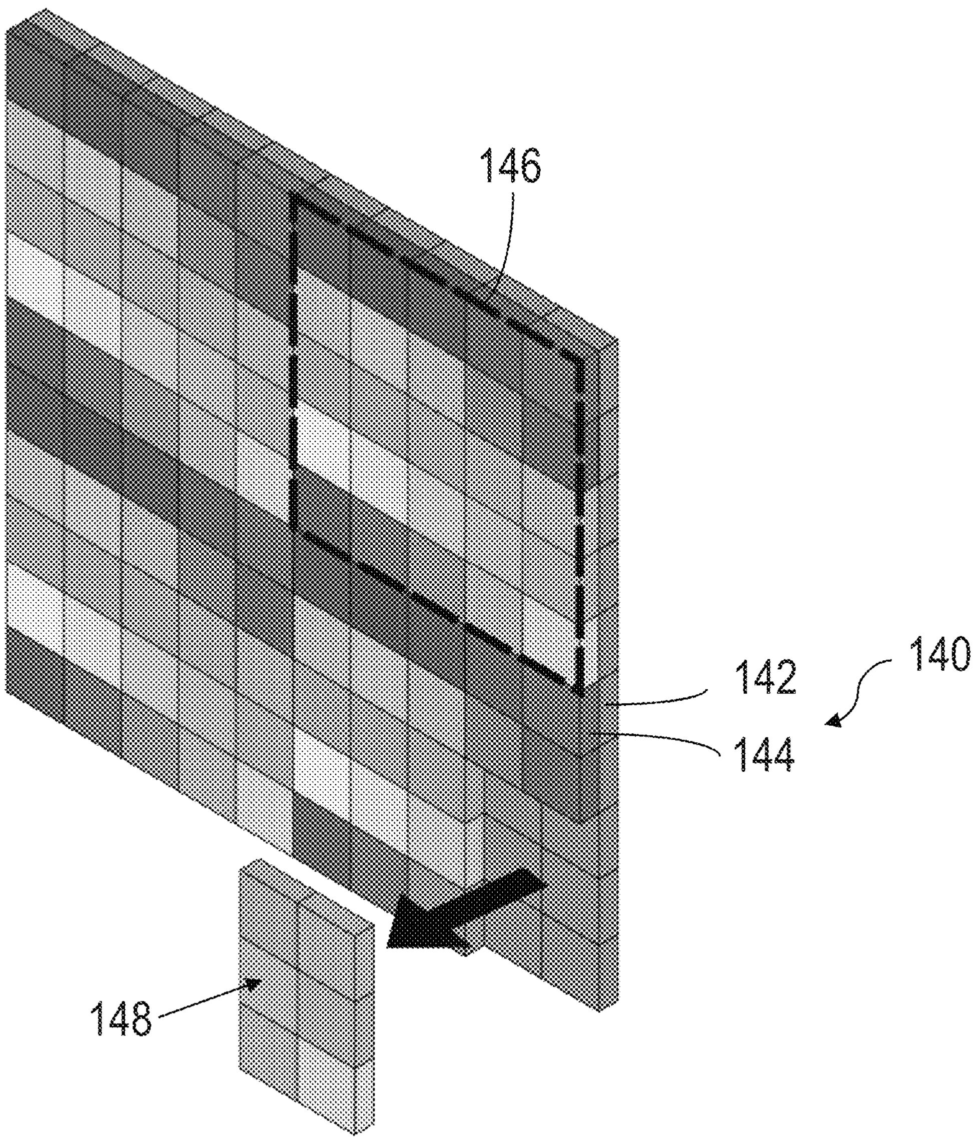
FIG. 2C depicts an example snapshot imaging system that can generate the datacube of FIG. 2A.

In comparison, a snapshot imaging system 140 can capture an entire datacube 120 in a single integration period or exposure, thereby avoiding such motion-induced image quality issues. FIG. 2C depicts an example image sensor 142 and an optical filter array such as a color filter array (CFA) 144 that can be used to create a snapshot imaging system. The CFA 144 in this example is a repeating pattern of color filter units 146 across the surface of the image sensor 142. This method of acquiring spectral information can also be referred to as a multispectral filter array (MSFA) or a spectrally resolved detector array (SRDA). In the illustrated example, the color filter unit 146 includes a 5×5 arrangement of different color filters, which would generate 25 spectral channels in the resulting image data. By way of these different color filters, the CFA can split incoming light into the bands of the filters, and direct the split light to dedicated photoreceptors on the image sensor. In this way, for a given color 148, only $1/25^{th}$ of the photoreceptors actually detect a signal represent light of that wavelength. Thus, although 25 different color channels can be generated in a single exposure with this snapshot imaging system 140, each color channel represents a smaller quantity of measured data than the total output of the sensor 142. In some embodiments, a CFA may include one or more of a filter array (MSFA), a spectrally resolved detector array (SRDA), and/or may include a conventional Bayer filter, CMYK filter, or any other absorption-based or interference-based filters. One type of interference based filter would be an array of thin film filters arranged in a grid with each element of the grid corresponding to one or more sensor elements. Another type of interference based filter is a Fabry-Pérot filter. Nano-etched interference Fabry-Pérot filters, which exhibit typical bandpass full-width-at-half-maxima (FWHM) on the order of 20 to 50 nm, are advantageous because they can be used in some embodiments due to the slow roll-off of the filters' passband seen in the transition from its center wavelength to its blocking band. These filters also exhibit a low OD in these blocking bands further enabling increased sensitivity to light outside of their passbands. These combined effects makes these specific filters sensitive to spectral regions that would otherwise be blocked by the fast roll-off of a high OD interference filter with a similar FWHM made with many thin film layers in a coating deposition process such as in evaporative deposition or in ion-beam sputtering. In embodiments with dye-based CMYK or RGB (Bayer) filter configurations, the slow spectral roll-off and the large FWHM of individual filter passbands are preferred and provide a unique spectral transmission percentage to individual wavelengths throughout an observed spectrum.

Accordingly, the datacube 120 that results from a snapshot imaging system will have one of two properties that can be problematic for precision imaging applications. As a first option, the datacube 120 that results from a snapshot imaging system can have smaller $N_x$ and $N_y$ sizes than the (x, y) size of the detector array and, thus be of lower resolution than the datacube 120, which would be generated by a scanning imaging system having the same image sensor. As a second option, the datacube 120 that results from a snapshot imaging system can have the same $N_x$ and $N_y$ sizes as the (x, y) size of the detector array due to interpolating values for certain (x, y) positions. However, the interpolation used to generate such a datacube means that certain values in the datacube are not actual measurements of the wavelength of light incident on the sensor, but rather estimates of what the actual measurement may be based on surrounding values.

Another existing option for single-exposure multispectral imaging is the multispectral beamsplitter. In such imaging systems, beamsplitter cubes split incident light into distinct color bands, with each band observed by independent image sensors. While one can change the beamsplitter designs to adjust the measured spectral bands, it is not easy to divide the incident light into more than four beams without compromising the system performance. Thus, four spectral channels appear to be the practical limit of this approach. A closely related method is to use thin-film filters instead of the bulkier beamsplitter cubes/prisms to split the light, however this approach is still limited to about six spectral channels due to space limitations and cumulative transmission losses through successive filters.

The aforementioned problems, among others, are addressed in some embodiments by the disclosed multi-aperture spectral imaging system with curved multi-bandpass filters to filter light incoming through each aperture, and the associated image data processing techniques. This particular configuration is able to achieve all of the design goals of fast imaging speeds, high resolution images, and precise fidelity of detected wavelengths. Accordingly, the disclosed optical design and associated image data processing techniques can be used in portable spectral imaging systems and/or to image moving targets, while still yielding a datacube suitable for high precision applications (e.g., clinical tissue analysis, biometric recognition, transient clinical events). These higher precision applications may include the diagnosis of melanoma in the preceeding stages (0 through 3) before metastasis, the classification of burn wound severity on skin tissue, or the tissue diagnosis of diabetic foot ulcer severity. Accordingly, the small form factor and the snapshot spectral acquisition as depicted in some embodiments will enable the use of this invention in clinical environments with transient events, which include the diagnosis of several different retinopathies (e.g. non proliferative diabetic retinopathy, proliferative diabetic retinopathy, and age-related macular degeneration) and the imaging of moving pediatric patients. Accordingly, it will be appreciated by one of skill in the art that the use of a multi-aperture system with flat or curved multi-bandpass filters, as disclosed herein, represents a significant technological advance over prior spectral imaging implementations. Specifically, the multi-aperture system may enable the collection of 3D spatial images of or relating to object curvature, depth, volume, and/or area based on the calculated disparity of the perspective differences between each aperture. However, the multi-aperture strategies presented here are not limited to any specific filter and may include flat and/or thin filters, based on either interference or absorptive filtering. This invention, as disclosed herein, can be modified to include flat filters in the image space of the imaging system in the event of suitable lenses or apertures that use a small or acceptable range of incidence angles. Filters may also be placed at the aperture stop or at the entrance/exit pupil of the imaging lenses as one skilled in the art of optical engineering may see fit to do so.

Various aspects of the disclosure will now be described with regard to certain examples and embodiments, which are intended to illustrate but not limit the disclosure. Although the examples and embodiments described herein will focus, for the purpose of illustration, on specific calculations and algorithms, one of skill in the art will appreciate the examples are to illustrate only, and are not intended to be limiting. For example, although some examples are presented in the context of a multispectral imaging, the disclosed multi-aperture imaging system and associated filters can be configured to achieve hyperspectral imaging in other implementations. Further, although certain examples are presented as achieving benefits for handheld and/or moving target applications, it will be appreciated that the disclosed imaging system design and associated processing techniques can yield a high precision datacube suitable for fixed imaging systems and/or for analysis of relatively motionless targets.

Overview of Electromagnetic Ranges and Image Sensors

Certain colors or portions of the electromagnetic spectrum are referred to herein, and will now be discussed with respect to their wavelength as defined by the ISO 21348 definitions of irradiance spectral categories. As described further below, in certain imaging applications the wavelength ranges for specific colors can be grouped together to pass through a certain filter.

Electromagnetic radiation ranging from wavelengths of or approximately 760 nm to wavelengths of or approximately 380 nm are typically considered the "visible" spectrum, that is, the portion of the spectrum recognizable by the color receptors of the human eye. Within the visible spectrum, red light typically is considered to have a wavelength of or approximately 700 nanometers (nm), or to be in the range of or approximately 760 nm to 610 nm or approximately 610 nm. Orange light typically is considered to have a wavelength of or approximately 600 nm, or to be in the range of or approximately 610 nm to approximately 591 nm or 591 nm. Yellow light typically is considered to have a wavelength of or approximately 580 nm, or to be in the range of or approximately 591 nm to approximately 570 nm or 570 nm. Green light typically is considered to have a wavelength of or approximately 550 nm, or to be in the range of or approximately 570 nm to approximately 500 nm or 500 nm. Blue light typically is considered to have a wavelength of or approximately 475 nm, or to be in the range of or approximately 500 nm to approximately 450 nm or 450 nm. Violet (purple) light typically is considered to have a wavelength of or approximately 400 nm, or to be in the range of or approximately 450 nm to approximately 360 nm or 360 nm.

Turning to ranges outside of the visible spectrum, infrared (IR) refers to electromagnetic radiation with longer wavelengths than those of visible light, and is generally invisible to the human eye. IR wavelengths extend from the nominal red edge of the visible spectrum at approximately 760 nm or 760 nm to approximately 1 millimeter (mm) or 1 mm. Within this range, near infrared (NIR) refers to the portion of the spectrum that is adjacent to the red range, ranging from wavelengths between approximately 760 nm or 760 nm to approximately 1400 nm or 1400 nm.

Ultraviolet (UV) radiation refers to some electromagnetic radiation with shorter wavelengths than those of visible light, and is generally invisible to the human eye. UV wavelengths extend from the nominal violet edge of the visible spectrum at approximately 40 nm or 40 nm to approximately 400 nm. Within this range, near ultraviolet (NUV) refers to the portion of the spectrum that is adjacent to the violet range, ranging from wavelengths between approximately 400 nm or 400 nm to approximately 300 nm or 300 nm, middle ultraviolet (MUV) ranges from wavelengths between approximately 300 nm or 300 nm to approximately 200 nm or 200 nm, and far ultraviolet (FUV) ranges from wavelengths between approximately 200 nm or 200 nm to approximately 122 nm or 122 nm.

The image sensors described herein can be configured to detect electromagnetic radiation in any of the above-described ranges, depending upon the particular wavelength ranges that are suitable for a particular application. The spectral sensitivity of a typical silicon-based charge-coupled device (CCD) or complementary metal-oxide-semiconductor (CMOS) sensor extends across the visible spectrum, and also extends considerably into the near-infrared (IR) spectrum and sometimes into the UV spectrum. Some implementations can alternatively or additionally use back-illuminated or front-illuminated CCD or CMOS arrays. For applications requiring high SNR and scientific-grade measurements, some implementations can alternatively or additionally use either scientific complementary metal-oxide-semiconductor (sCMOS) cameras or electron multiplying CCD cameras (EMCCD). Other implementations can alternatively or additionally use sensors known to operate in specific color ranges (e.g., short-wave infrared (SWIR), mid-wave infrared (MWIR), or long-wave infrared (LWIR)) and corresponding optical filter arrays, based on the intended applications. These may alternatively or additionally include cameras based around detector materials including indium gallium arsenide (InGaAs) or indium antimonide (InSb) or based around microbolometer arrays.

The image sensors used in the disclosed multispectral imaging techniques may be used in conjunction with an optical filter array such as a color filter array (CFA). Some CFAs can split incoming light in the visible range into red (R), green (G), and blue (B) categories to direct the split visible light to dedicated red, green, or blue photodiode receptors on the image sensor. A common example for a CFA is the Bayer pattern, which is a specific pattern for arranging RGB color filters on a rectangular grid of photosensors. The Bayer pattern is 50% green, 25% red and 25% blue with rows of repeating red and green color filters alternating with rows of repeating blue and green color filters. Some CFAs (e.g., for RGB-NIR sensors) can also separate out the NIR light and direct the split NIR light to dedicated photodiode receptors on the image sensor.

As such, the wavelength ranges of the filter components of the CFA can determine the wavelength ranges represented by each image channel in a captured image. Accordingly, a red channel of an image may correspond to the red wavelength regions of the color filter and can include some yellow and orange light, ranging from approximately 570 nm or 570 nm to approximately 760 nm or 760 nm in various embodiments. A green channel of an image may correspond to a green wavelength region of a color filter and can include some yellow light, ranging from approximately 570 nm or 570 nm to approximately 480 nm or 480 nm in various embodiments. A blue channel of an image may correspond to a blue wavelength region of a color filter and can include some violet light, ranging from approximately 490 nm or 490 nm to approximately 400 nm or 400 nm in various embodiments. As a person of ordinary skill in the art will appreciate, exact beginning and ending wavelengths (or portions of the electromagnetic spectrum) that define colors of a CFA (for example, red, green, and blue) can vary depending upon the CFA implementation.

Further, typical visible light CFAs are transparent to light outside the visible spectrum. Therefore, in many image sensors the IR sensitivity is limited by a thin-film reflective IR filter at the face of the sensor that blocks the infrared wavelength while passing visible light. However, this may be omitted in some of the disclosed imaging systems to allow of passage of IR light. Thus, the red, green, and/or blue channels may also be used to collect IR wavelength bands. In some implementations the blue channel may also be used to collect certain NUV wavelength bands. The distinct spectral responses of the red, green, and blue channels with regard to their unique transmission efficiencies at each wavelength in a spectral image stack may provide a uniquely weighted response of spectral bands to be unmixed using the known transmission profiles. For example, this may include the known transmission response in IR and UV wavelength regions for the red, blue, and green channels, enabling their use in the collection of bands from these regions.

As described in further detail below, additional color filters can be placed before the CFA along the path of light towards the image sensor in order to selectively refine the specific bands of light that become incident on the image sensor. Some of the disclosed filters can be either a combination of dichroic (thin-film) and/or absorptive filters or a single dichroic and/or absorptive filter. Some of the disclosed color filters can be bandpass filters that pass frequencies within a certain range (in a passband) and reject (attenuates) frequencies outside that range (in a blocking range). Some of the disclosed color filters can be multi-bandpass filters that pass multiple discontinuous ranges of wavelengths. These "wavebands" can have smaller passband ranges, larger blocking range attenuation, and sharper spectral roll-off, which is defined as the steepness of the spectral response as the filter transitions from the passband to the blocking range, than the larger color range of the CFA filter. For example, these disclosed color filters can cover a passband of approximately 20 nm or 20 nm or approximately 40 nm or 40 nm. The particular configuration of such color filters can determine the actual wavelength bands that are incident upon the sensor, which can increase the precision of the disclosed imaging techniques. The color filters described herein can be configured to selectively block or pass specific bands of electromagnetic radiation in any of the above-described ranges, depending upon the particular wavelength bands that are suitable for a particular application.

As described herein, a "pixel" can be used to describe the output generated by an element of the 2D detector array. In comparison, a photodiode, a single photosensitive element in this array, behaves as a transducer capable of converting photons into electrons via the photoelectric effect, which is then in turn converted into a usable signal used to determine the pixel value. A single element of the datacube can be referred to as a "voxel" (e.g., a volume element). A "spectral vector" refers to a vector describing the spectral data at a particular (x, y) position in a datacube (e.g., the spectrum of light received from a particular point in the object space). A single horizontal plane of the datacube (e.g., an image representing a single spectral dimension), is referred to herein as a an "image channel". Certain embodiments described herein may capture spectral video information, and the resulting data dimensions can assume the "hypercube" form $N_xN_yN_\lambda N_t$, where $N_t$ is the number of frames captured during a video sequence.

Figure 3A:
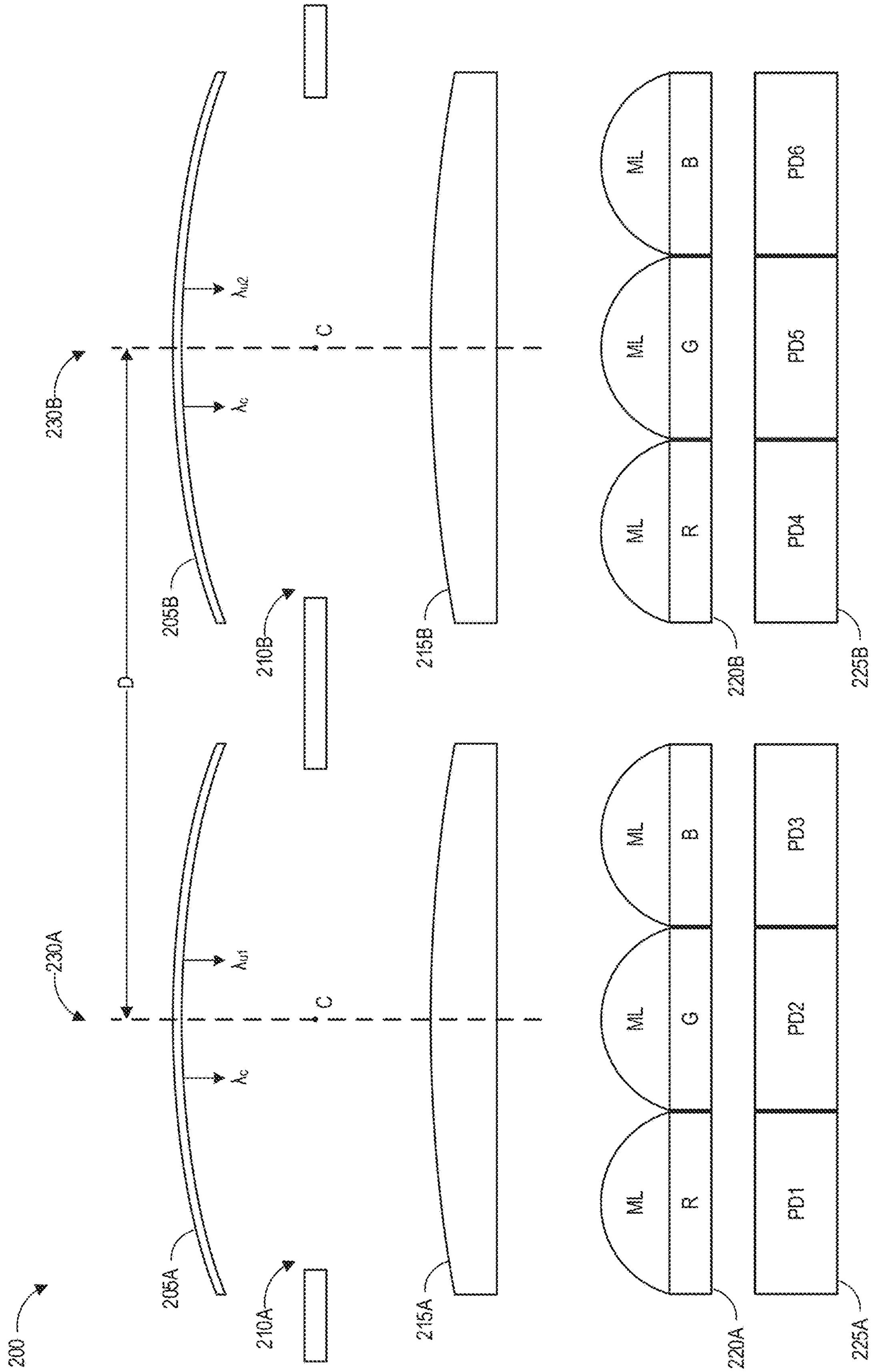
FIG. 3A depicts a schematic cross-sectional view of an optical design of an example multi-aperture imaging system with curved multi-bandpass filters, according to the present disclosure.

Overview of Example Multi-Aperture Imaging Systems with Curved Multi-Bandpass Filters FIG. 3A depicts a schematic view of an example multi-aperture imaging system 200 with curved multi-bandpass filters, according to the present disclosure. The illustrated view includes a first image sensor region 225A (photodiodes PD1-PD3) and a second image sensor region 225B (photodiodes PD4-PD6). The photodiodes PD1-PD6 can be, for example, photodiodes formed in a semiconductor substrate, for example in a CMOS image sensor. Generally, each of the photodiodes PD1-PD6 can be a single unit of any material, semiconductor, sensor element or other device that converts incident light into current. It will be appreciated that a small portion of the overall system is illustrated for the purpose of explaining its structure and operation, and that in implementation image sensor regions can have hundreds or thousands of photodiodes (and corresponding color filters). The image sensor regions 225A and 225B may be implemented as separate sensors, or as separate regions of the same image sensor, depending upon the implementation. Although FIG. 3A depicts two apertures and corresponding light paths and sensor regions, it will be appreciated that the optical design principles illustrated by FIG. 3A can be extended to three or more apertures and corresponding light paths and sensor regions, depending upon the implementation.

The multi-aperture imaging system 200 includes a first opening 210A that provides a first light path towards the first sensor region 225A, and a second opening 210B that provides a first light path towards the second sensor region 225B. These apertures may be adjustable to increase or decrease the brightness of the light that falls on the image, or so that the duration of particular image exposures can be changed and the brightness of the light that falls on the image sensor regions does not change. These apertures may also be located at any position along the optical axes of this multi-aperture system as deemed reasonable by one skilled in the art of optical design. The optical axis of the optical components positioned along the first light path is illustrated by dashed line 230A and the optical axis of the optical components positioned along the second light path is illustrated by dashed line 230B, and it will be appreciated that these dashed lines do not represent a physical structure of the multi-aperture imaging system 200. The optical axes 230A, 230B are separated by a distance D, which can result in disparity between the images captured by the first and second sensor regions 225A, 225B. Disparity refers to the distance between two corresponding points in the left and right (or upper and lower) images of a stereoscopic pair, such that the same physical point in the object space can appear in different locations in each image. Processing techniques to compensate for and leverage this disparity are described in further detail below.

Each optical axis 230A, 230B passes through a center C of the corresponding aperture, and the optical components can also be centered along these optical axes (e.g., the point of rotational symmetry of an optical component can be positioned along the optical axis). For example, the first curved multi-bandpass filter 205A and first imaging lens 215A can be centered along the first optical axis 230A, and the second curved multi-bandpass filter 205B and second imaging lens 215B can be centered along the second optical axis 230B.

As used herein with respect to positioning of optical elements, "over" and "above" refer to the position of a structure (for example, a color filter or lens) such that light entering the imaging system 200 from the object space propagates through the structure before it reaches (or is incident upon) another structure. To illustrate, along the first light path, the curved multi-bandpass filter 205A is positioned above the aperture 210A, the aperture 210A is positioned above imaging lens 215A, the imaging lens 215A is positioned above the CFA 220A, and the CFA 220A is positioned above the first image sensor region 225A. Accordingly, light from the object space (e.g., the physical space being imaged) first passes through the curved multi-bandpass filter 205A, then the aperture 210A, then the imaging lens 215A, then the CFA 220A, and finally is incident on the first image sensor region 225A. The second light path (e.g., curved multi-bandpass filter 205B, aperture 210B, imaging lens 215B, CFA 220B, second image sensor region 225B) follows a similar arrangement. In other implementations, the aperture 210A, 210B and/or imaging lenses 215A, 215B can be positioned above the curved multi-bandpass filter 205A, 205B. Additionally, other implementations may not use a physical aperture and may rely on the clear aperture of the optics to control the brightness of light that is imaged onto the sensor region 225A, 225B. Accordingly, the lens 215A, 215B may be placed above the aperture 210A, 210B and curved multi-bandpass filter 205A, 205B. In this implementation, the aperture 210A, 210B and lens 215A, 215B may be also be placed over or under each other as deemed necessary by one skilled in the art of optical design.

The first CFA 220A positioned over the first sensor region 225A and the second CFA 220B positioned over the second sensor region 225B can act as wavelength-selective pass filters and split incoming light in the visible range into red, green, and blue ranges (as indicated by the R, G, and B notation). The light is "split" by allowing only certain selected wavelengths to pass through each of the color filters in the first and second CFAs 220A, 220B. The split light is received by dedicated red, green, or blue diodes on the image sensor. Although red, blue, and green color filters are commonly used, in other embodiments the color filters can vary according to the color channel requirements of the captured image data, for example including ultraviolet, infrared, or near-infrared pass filters, as with an RGB-IR CFA.

As illustrated, each filter of the CFA is positioned over a single photodiode PD1-PD6. FIG. 3A also illustrates example microlenses (denoted by ML) that can be formed on or otherwise positioned over each color filter, in order to focus incoming light onto active detector regions. Other implementations may have multiple photodiodes under a single filter (e.g., clusters of 2, 4, or more adjacent photodiodes). In the illustrated example, photodiode PD1 and photodiode PD4 are under red color filters and thus would output red channel pixel information; photodiode PD2 and photodiode PD5 are under green color filters and, thus would output green channel pixel information; and photodiode PD3 and photodiode PD6 are under blue color filters and thus would output blue channel pixel information. Further, as described in more detail below, the specific color channels output by given photodiodes can be further limited to narrower wavebands based on activated illuminants and/or the specific wavebands passed by the multi-bandpass filters 205A, 205B, such that a given photodiode can output different image channel information during different exposures.

The imaging lenses 215A, 215B can be shaped to focus an image of the object scene onto the sensor regions 225A, 225B. Each imaging lens 215A, 215B may be composed of as many optical elements and surfaces needed for image formation and are not limited to single convex lenses as presented in FIG. 3A, enabling the use of a wide variety of imaging lenses or lens assemblies that would be available commercially or by custom design. Each element or lens assembly may be formed or bonded together in a stack or held in series using an optomechanical barrel with a retaining ring or bezel. In some embodiments, elements or lens assemblies may include one or more bonded lens groups, such as two or more optical components cemented or otherwise bonded together. In various embodiments, any of the multi-bandpass filters described herein may be positioned in front of a lens assembly of the multispectral image system, in front of a singlet of the multispectral image system, behind a lens assembly of the multispectral image system, behind a singlet of the multispectral image system, inside a lens assembly of the multispectral image system, inside a bonded lens group of the multispectral image system, directly onto a surface of a singlet of the multispectral image system, or directly onto a surface of an element of a lens assembly of the multispectral image system. Further, the aperture 210A and 210B may be removed, and the lenses 215A, 215B may be of the variety typically used in photography with either digital-single-lens-reflex (DSLR) or mirrorless cameras. Additionally, these lenses may be of the variety used in machine vision using C-mount or S-mount threading for mounting. Focus adjustment can be provided by movement of the imaging lenses 215A, 215B relative to the sensor regions 225A, 225B or movement of the sensor regions 225A, 225B relative to the imaging lenses 215A, 215B, for example based on manual focusing, contrast-based autofocus, or other suitable autofocus techniques.

The multi-bandpass filters 205A, 205B can be each configured to selectively pass multiple narrow wavebands of light, for example wavebands of 10-50 nm in some embodiments (or wider or narrower wavebands in other embodiments). As illustrated in FIG. 3A, both multi-bandpass filters 205A, 205B can pass waveband $\lambda_c$ (the "common waveband"). In implementations with three or more light paths, each multi-bandpass filter can pass this common waveband. In this manner, each sensor region captures image information at the same waveband (the "common channel"). This image information in this common channel can be used to register the sets of images captured by each sensor region, as described in further detail below. Some implementations may have one common waveband and corresponding common channel, or may have multiple common wavebands and corresponding common channels.

In addition to the common waveband $\lambda_c$, each multi-bandpass filters 205A, 205B can be each configured to selectively pass one or more unique wavebands. In this manner, the imaging system 200 is able to increase the number of distinct spectral channels captured collectively by the sensor regions 205A, 205B beyond what can be captured by a single sensor region. This is illustrated in FIG. 3A by multi-bandpass filters 205A passing unique waveband $\lambda_{u1}$, and multi-bandpass filters 205B passing unique waveband $\lambda_{u2}$, where $\lambda_{u1}$ and $\lambda_{u2}$ represent different wavebands from one another. Although depicted as passing two wavebands, the disclosed multi-bandpass can each pass a set of two or more wavebands. For example, some implementations can pass four wavebands each, as described with respect to FIGS. 11A and 11B. In various embodiments, a larger number of wavebands may be passed. For example, some four-camera implementations may include multi-bandpass filters configured to pass 8 wavebands. In some embodiments, the number of wavebands may be, for example, 4, 5, 6, 7, 8, 9, 10, 12, 15, 16, or more wavebands.

The multi-bandpass filters 205A, 205B have a curvature selected to reduce the angular-dependent spectral transmission across the respective sensor regions 225A, 225B. As a result, when receiving narrowband illumination from the object space, each photodiode across the area of the sensor regions 225A, 225B that is sensitive to that wavelength (e.g., the overlying color filter passes that wavelength) should receive substantially the same wavelength of light, rather than photodiodes near the edge of the sensor experiencing the wavelength shift described above with respect to FIG. 1A. This can generate more precise spectral image data than using flat filters.

Figure 3B:
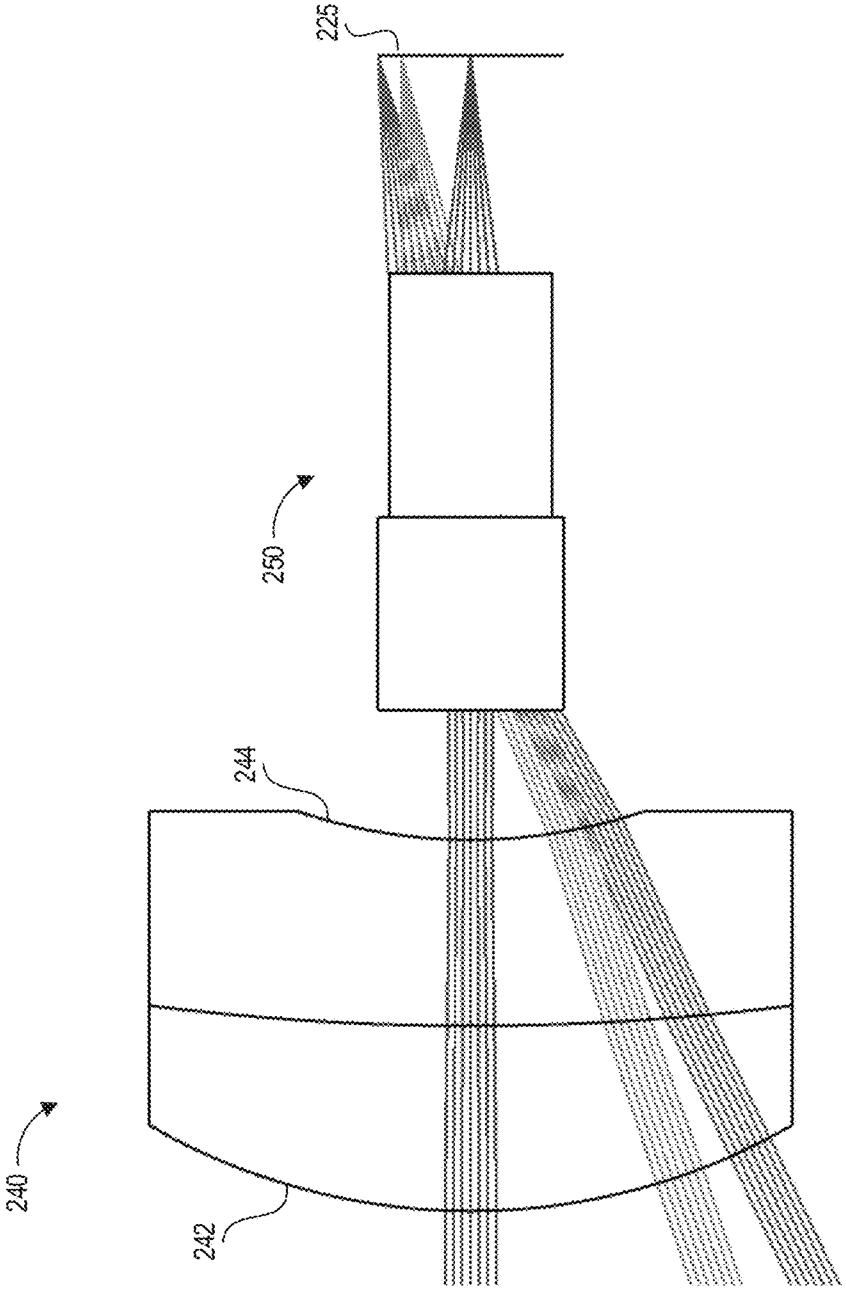
FIGS. 3B-3D depict example optical designs for optical components of one light path of the multi-aperture imaging system of FIG. 3A.

FIG. 3B depicts an example optical design for optical components of one light path of the multi-aperture imaging system of FIG. 3A. Specifically, FIG. 3B depicts a custom achromatic doublet 240 that can be used to provide the multi-bandpass filters 205A, 205B. The custom achromatic doublet 240 passes light through a housing 250 to an image sensor 225. The housing 250 can include openings 210A, 210B and imaging lens 215A, 215B described above.

The achromatic doublet 240 is configured to correct for optical aberrations as introduced by the incorporation of surfaces required for the multi-bandpass filter coatings 205A, 205B. The illustrated achromatic doublet 240 includes two individual lenses, which can be made from glasses or other optical materials having different amounts of dispersion and different refractive indices. Other implementations may use three or more lenses. These achromatic doublet lenses can be designed to incorporate the multi-bandpass filter coatings 205A, 205B on the curved front surface 242 while eliminating optical aberrations introduced that would otherwise be present through the incorporation of a curved singlet optical surface with the deposited filter coatings 205A, 205B while still limiting optical or focusing power provided by the achromatic doublet 240 due to the combinatorial effect of the curved front surface 242 and the curved back surface of 244 while still keeping the primary elements for focusing light restricted to the lenses housed in housing 250. Thus, the achromatic doublet 240 can contribute to the high precision of image data captured by the system 200. These individual lenses can be mounted next to each other, for example being bonded or cemented together, and shaped such that the aberration of one of the lenses is counterbalanced by that of the other. The achromatic doublet 240 curved front surface 242 or the curved back surface 244 can be coated with the multi-bandpass filter coating 205A, 205B. Other doublet designs may be implemented with the systems described herein.

Figure 3C:
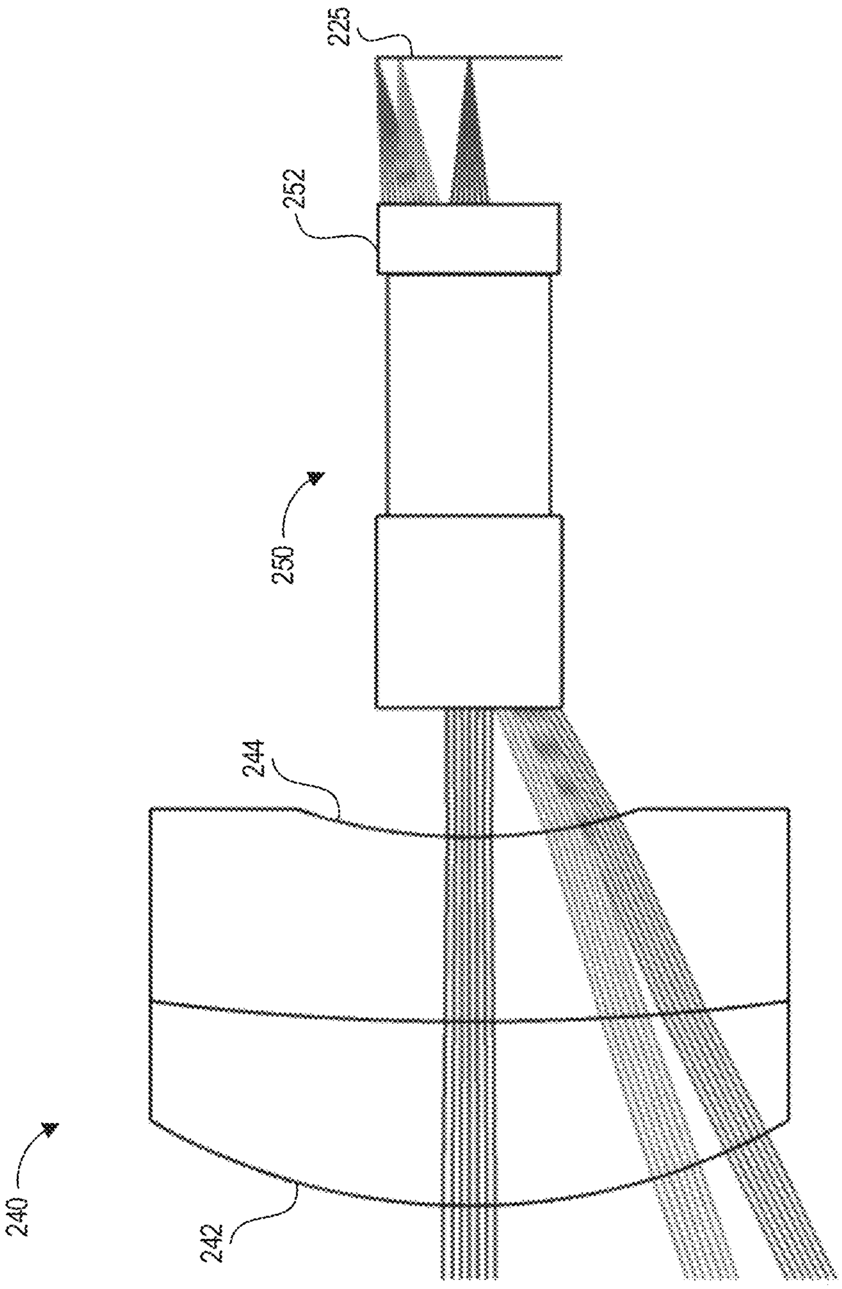
Figure 3D:
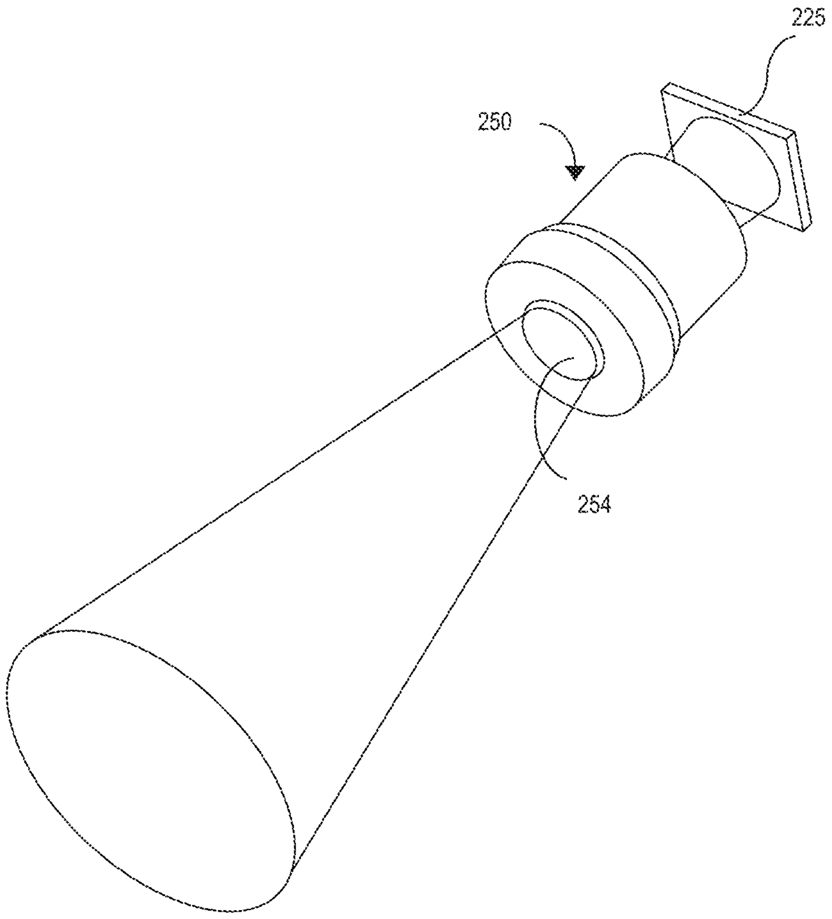

Further variations of the optical designs described herein may be implemented. For example, in some embodiments a light path may include a singlet or other optical singlet such as of the positive or negative meniscus variety as depicted in FIG. 3A instead of the doublet 240 depicted in FIG. 3B. FIG. 3C illustrates an example implementation in which a flat filter 252 is included between the lens housing 250 and the sensor 225. The achromatic doublet 240 in FIG. 3C provides optical aberration correction as introduced by the inclusion of the flat filter 252 containing a multi-bandpass transmission profile while not significantly contributing to the optical power as provided by the lenses contained in housing 250. FIG. 3D illustrates another example of an implementation in which the multi-bandpass coating is implemented by means of a multi-bandpass coating 254 applied to the front surface of the lens assembly contained within the housing 250. As such, this multi-bandpass coating 254 may be applied to any curved surface of any optical element residing within housing 250.

Figure 4A:
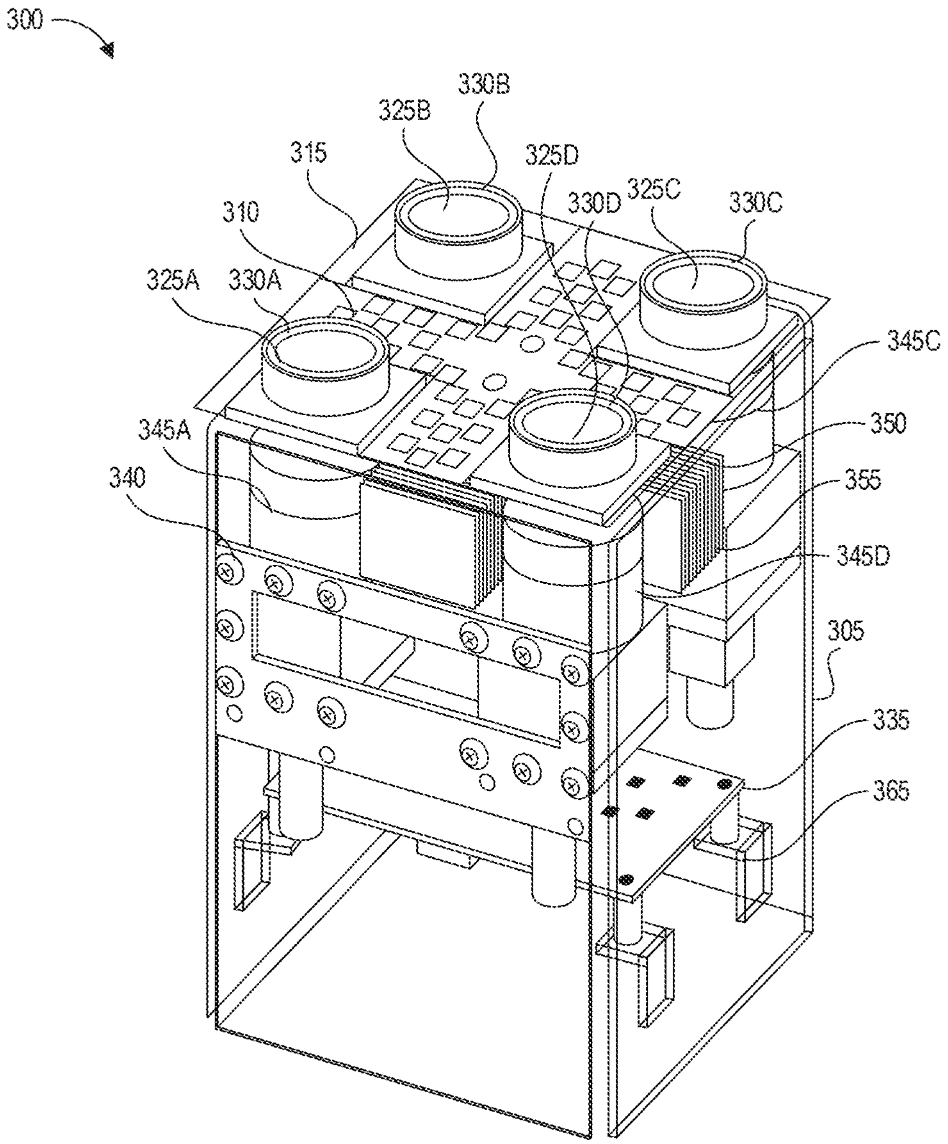
FIGS. 4A-4E depict an embodiment of a multispectral multi-aperture imaging system, with an optical design as described with respect to FIGS. 3A and 3B.
Figure 4C:
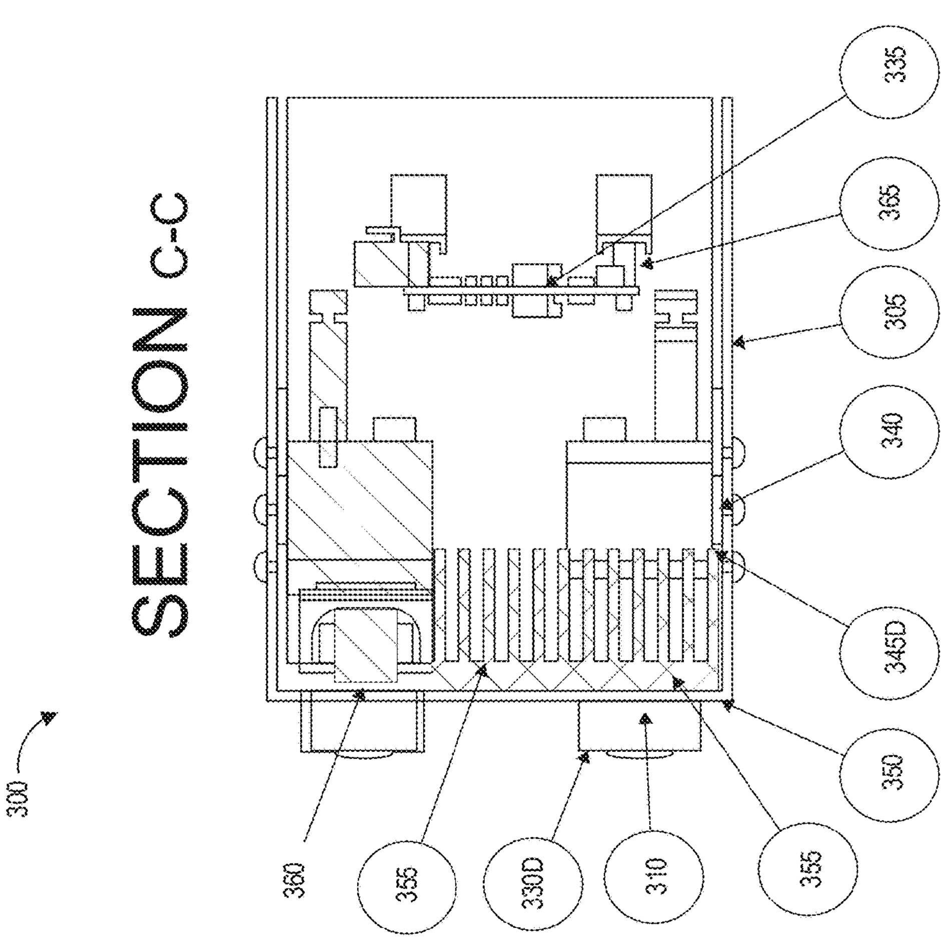
Figure 4B:
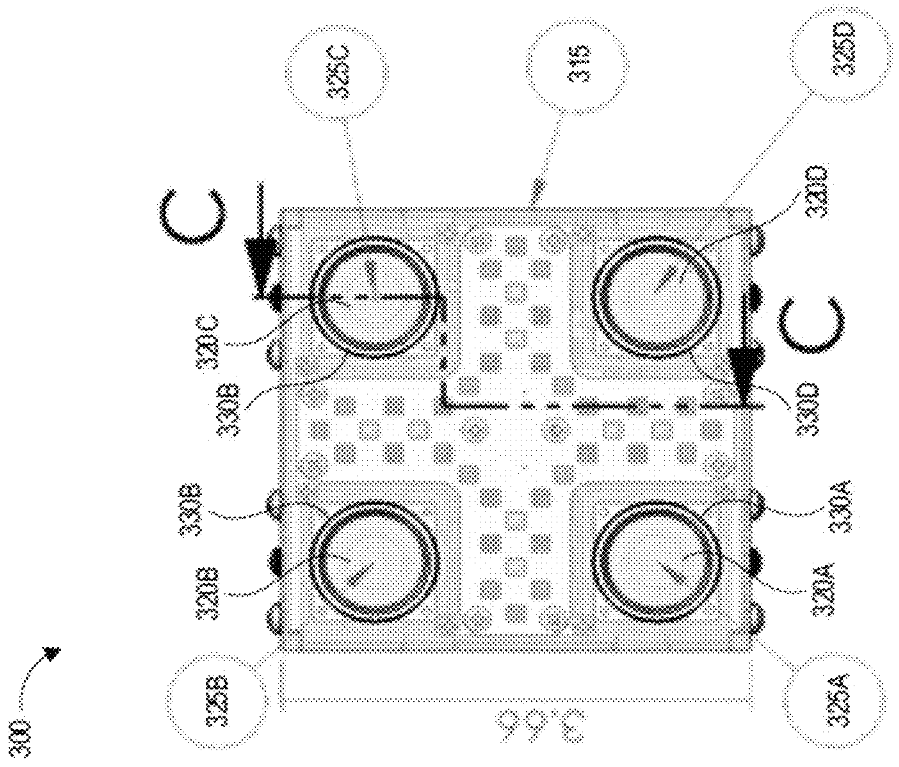
Figure 4E:
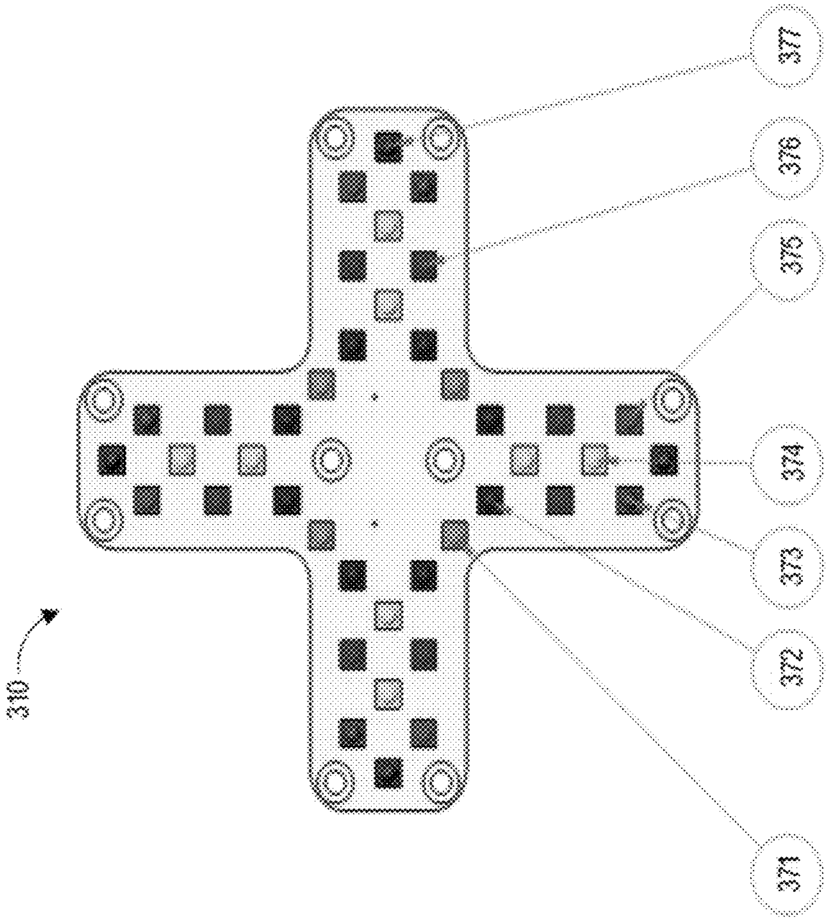
Figure 4D:
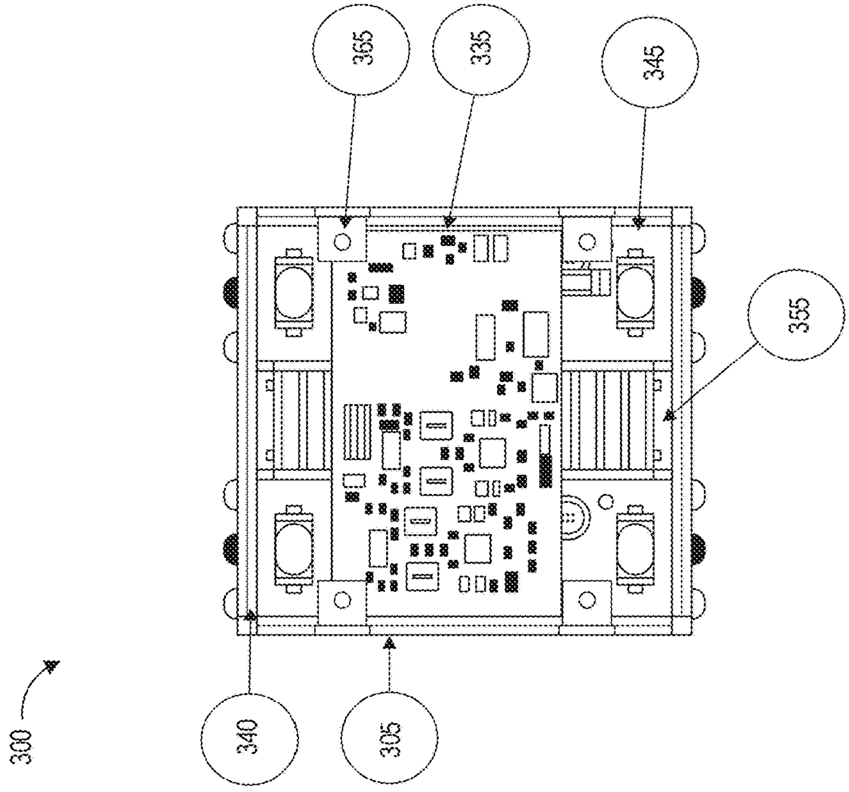

FIGS. 4A-4E depict an embodiment of a multispectral, multi-aperture imaging system 300, with an optical design as described with respect to FIGS. 3A and 3B. Specifically, FIG. 4A depicts a perspective view of the imaging system 300 with the housing 305 illustrated with translucency to reveal interior components. The housing 305 may be larger or smaller relative to the illustrated housing 305, for example, based on a desired amount of embedded computing resources. FIG. 4B depicts a front view of the imaging system 300. FIG. 4C depicts a cutaway side view of the imaging system 300, cut along line C-C illustrated in FIG. 4B. FIG. 4D depicts a bottom view of the imaging system 300 depicting the processing board 335. FIGS. 4A-4D are described together below.

Figure 18B:
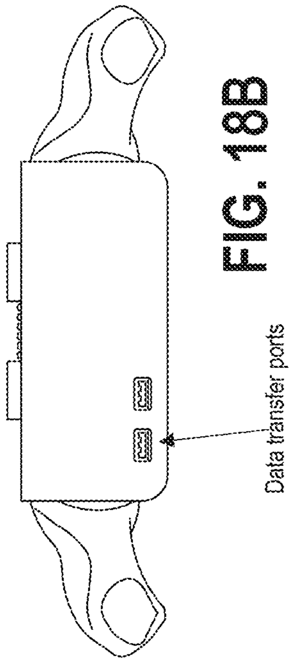
FIGS. 18A-18C illustrate an example handheld embodiment of a multispectral, multi-aperture imaging system.
Figure 18C:
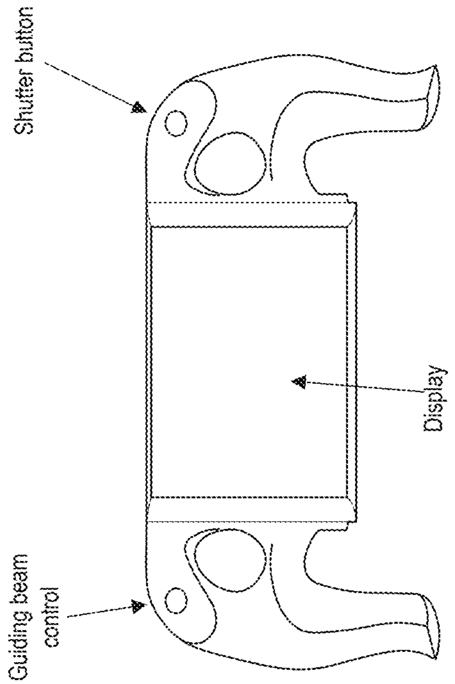
Figure 18A:
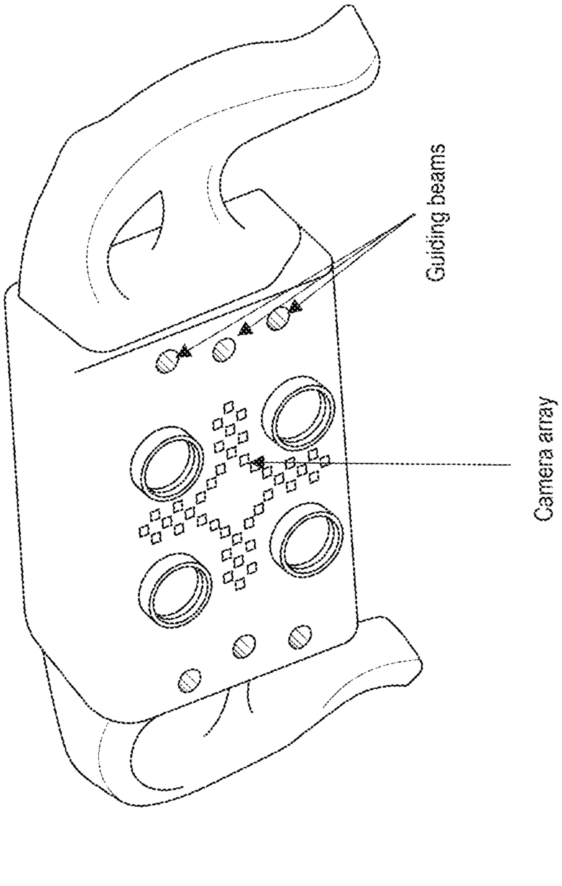
Figure 19A:
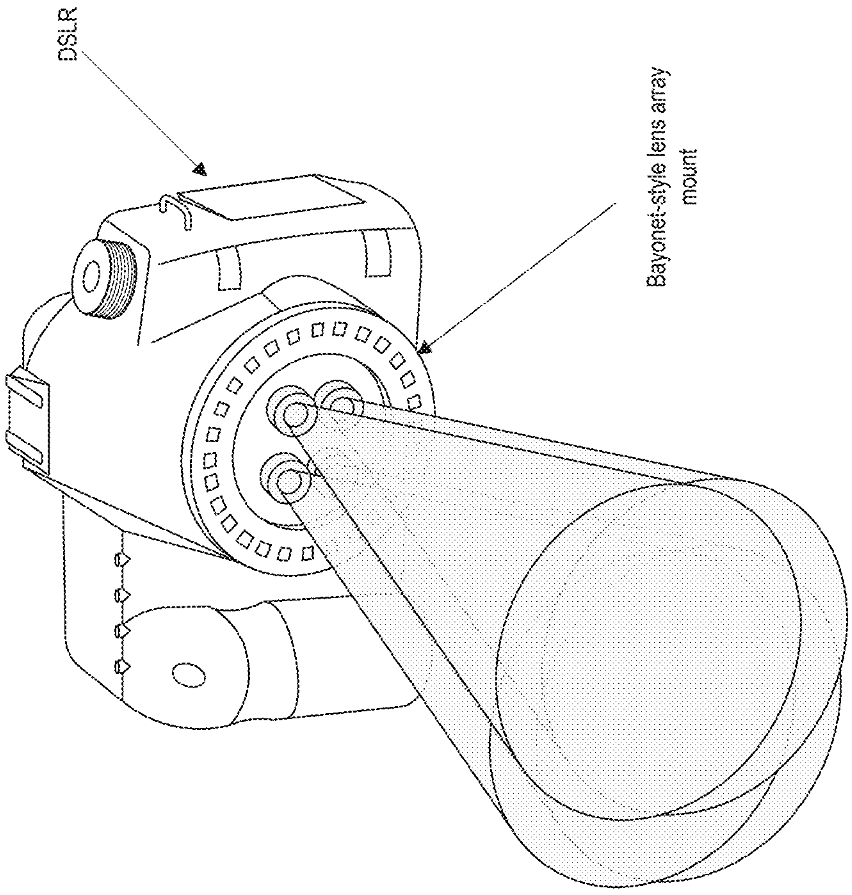
FIGS. 19A and 19B illustrate an example handheld embodiment of a multispectral, multi-aperture imaging system.
Figure 19B:
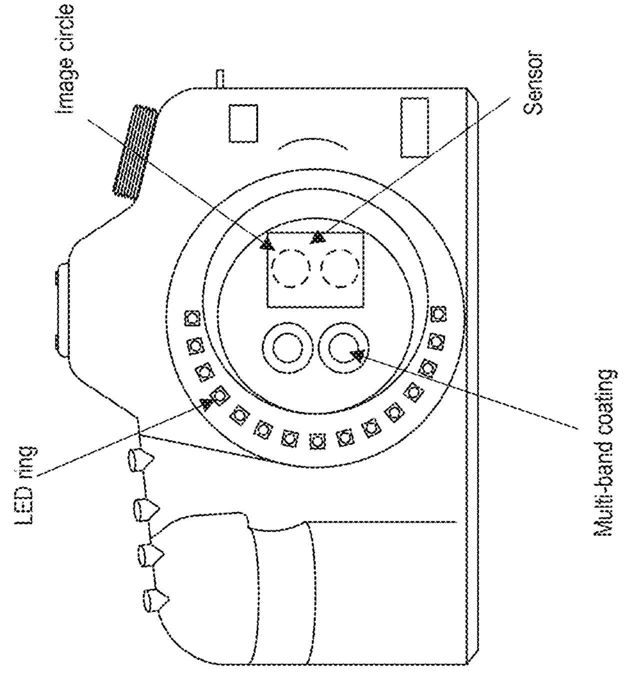
Figure 20A:
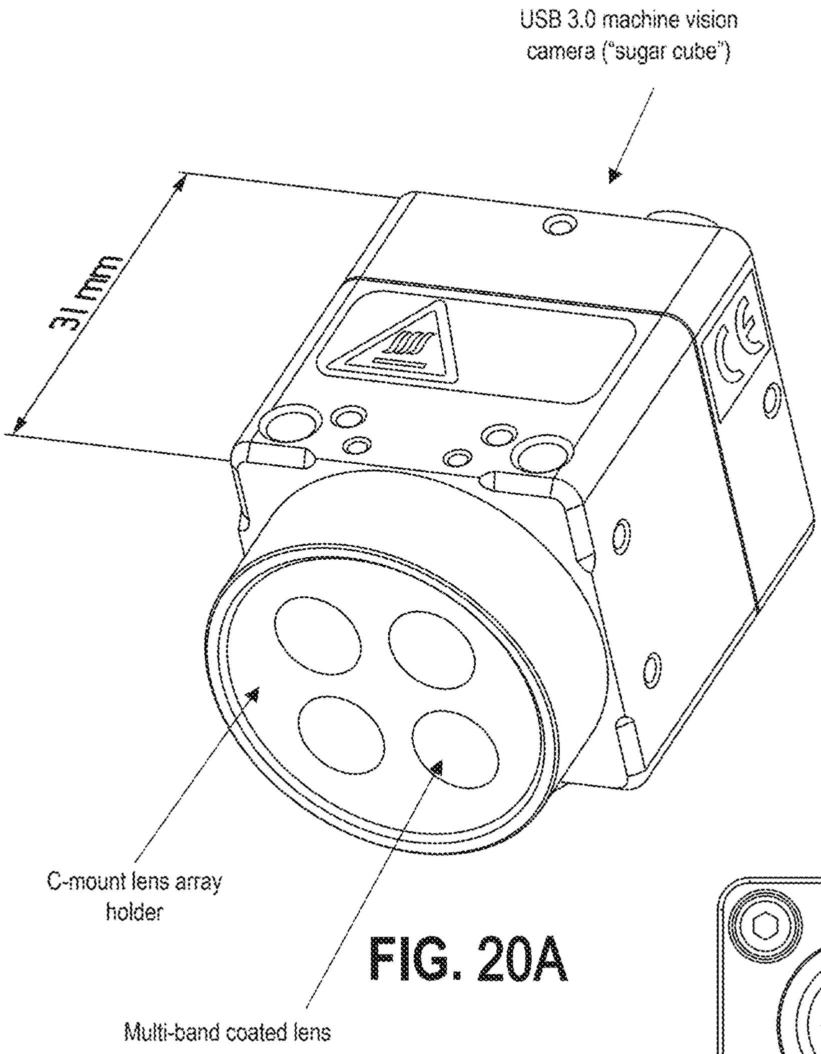
FIGS. 20A and 20B illustrate an example multispectral, multi-aperture imaging system for a small USB 3.0 enclosed in a common camera housing.
Figure 20B:
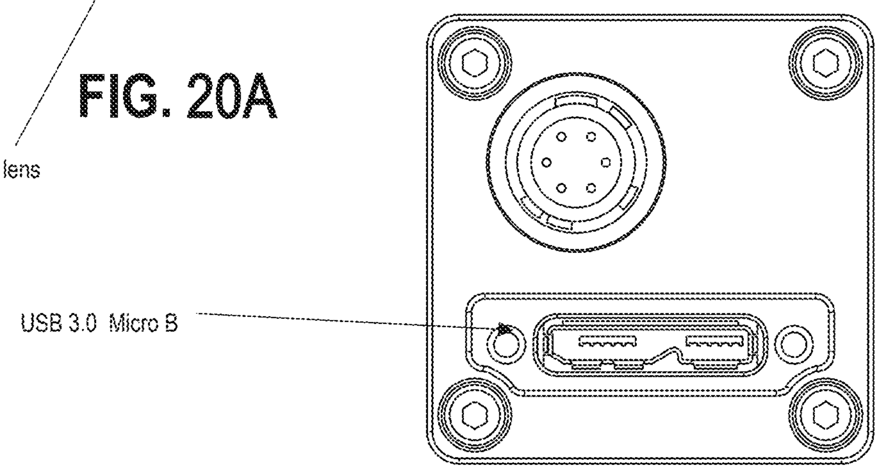

The housing 305 of the imaging system 300 may be encased in another housing. For example, handheld implementations may enclose the system within a housing optionally with one or more handles shaped to facilitate stable holding of the imaging system 300. Example handheld implementations are depicted in greater detail in FIGS. 18A-18C and in FIGS. 19A-19B. The upper surface of the housing 305 includes four openings 320A-320D. A different multi-bandpass filter 325A-325D is positioned over each opening 320A-320D and held in place by a filter cap 330A-330B. The multi-bandpass filters 325A-325D may be curved, and each pass a common waveband and at least one unique waveband, as described herein, in order to achieve high precision multi-spectral imaging across a greater number of spectral channels than would otherwise be captured by the image sensor due to its overlying color filter array. The image sensor, imaging lenses, and color filters described above are positioned within the camera housings 345A-345D. In some embodiments, a single camera housing may enclose the image sensors, imaging lenses, and color filters described above, for example, as shown in FIGS. 20A-20B. In the depicted implementation separate sensors are thus used (e.g., one sensor within each camera housing 345A-345D), but it will be appreciated that a single image sensor spanning across all of the regions exposed through the openings 320A-320D could be used in other implementations. The camera housings 345A-345D are secured to the system housing 305 using supports 340 in this embodiment, and can be secured using other suitable means in various implementations.

The upper surface of the housing 305 supports an optional illumination board 310 covered by an optical diffusing element 315. The illumination board 310 is described in further detail with respect to FIG. 4E, below. The diffusing element 315 can be composed of glass, plastic, or other optical material for diffusing light emitted from the illumination board 310 such that the object space receives substantially spatially-even illumination. Even illumination of the target object can be beneficial in certain imaging applications, for example clinical analysis of imaged tissue, because it provides, within each wavelength, a substantially even amount of illumination across the object surface. In some embodiments, the imaging systems disclosed herein may utilize ambient light instead of or in addition to light from the optional illumination board.

Due to heat generated by the illumination board 310 in use, the imaging system 300 includes a heat sink 350 including a number of heat dissipating fins 355. The heat dissipating fins 355 can extend into the space between the camera housings 345A-345D, and the upper portion of the heat sink 350 can draw heat from the illumination board 310 to the fins 355. The heat sink 350 can be made from suitable thermally conductive materials. The heat sink 350 may further help to dissipate heat from other components such that some implementations of imaging systems may be fanless.

A number of supports 365 in the housing 305 secure a processing board 335 in communication with the cameras 345A-345D. The processing board 335 can control operation of the imaging system 300. Although not illustrated, the imaging system 300 can also be configured with one or more memories, for example storing data generated by use of the imaging system and/or modules of computer-executable instructions for system control. The processing board 335 can be configured in a variety of ways, depending upon system design goals. For example, the processing board can be configured (e.g., by a module of computer-executable instructions) to control activation of particular LEDs of the illumination board 310. Some implementations can use a highly stable synchronous step-down LED driver, which can enable software control of analog LED current and also detect LED failure. Some implementations can additionally provide image data analysis functionality to the processing board (e.g., by modules of computer-executable instructions) 335 or to a separate processing board. Although not illustrated, the imaging system 300 can include data interconnects between the sensors and the processing board 335 such that the processing board 335 can receive and process data from the sensors, and between the illumination board 310 and the processing board 335 such that the processing board can drive activation of particular LEDs of the illumination board 310.

FIG. 4E depicts an example illumination board 310 that may be included in the imaging system 300, in isolation from the other components. The illumination board 310 includes four arms extending from a central region, with LEDs positioned along each arm in three columns. The spaces between LEDs in adjacent columns are laterally offset from one another to create separation between adjacent LEDs. Each column of LEDs includes a number of rows having different colors of LEDs. Four green LEDs 371 are positioned in the center region, with one green LED in each corner of the center region. Starting from the innermost row (e.g., closest to the center), each column includes a row of two deep red LEDs 372 (for a total of eight deep red LEDs). Continuing radially outward, each arm has a row of one amber LED 374 in the central column, a row of two short blue LEDs 376 in the outermost columns (for a total of eight short blue LEDs), another row of one amber LED 374 in the central column (for a total of eight amber LEDs), a row having one non-PPG NIR LED 373 and one red LED 375 in the outermost columns (for a total of four of each), and one PPG NIR LED 377 in the central column (for a total of four PPG NIR LEDs). A "PPG" LED refers to an LED activated during a number of sequential exposure for capturing photoplethysmographic (PPG) information representing pulsatile blood flow in living tissue. It will be understood that a variety of other colors and/or arrangements thereof may be used in illumination boards of other embodiments.

Figure 5:
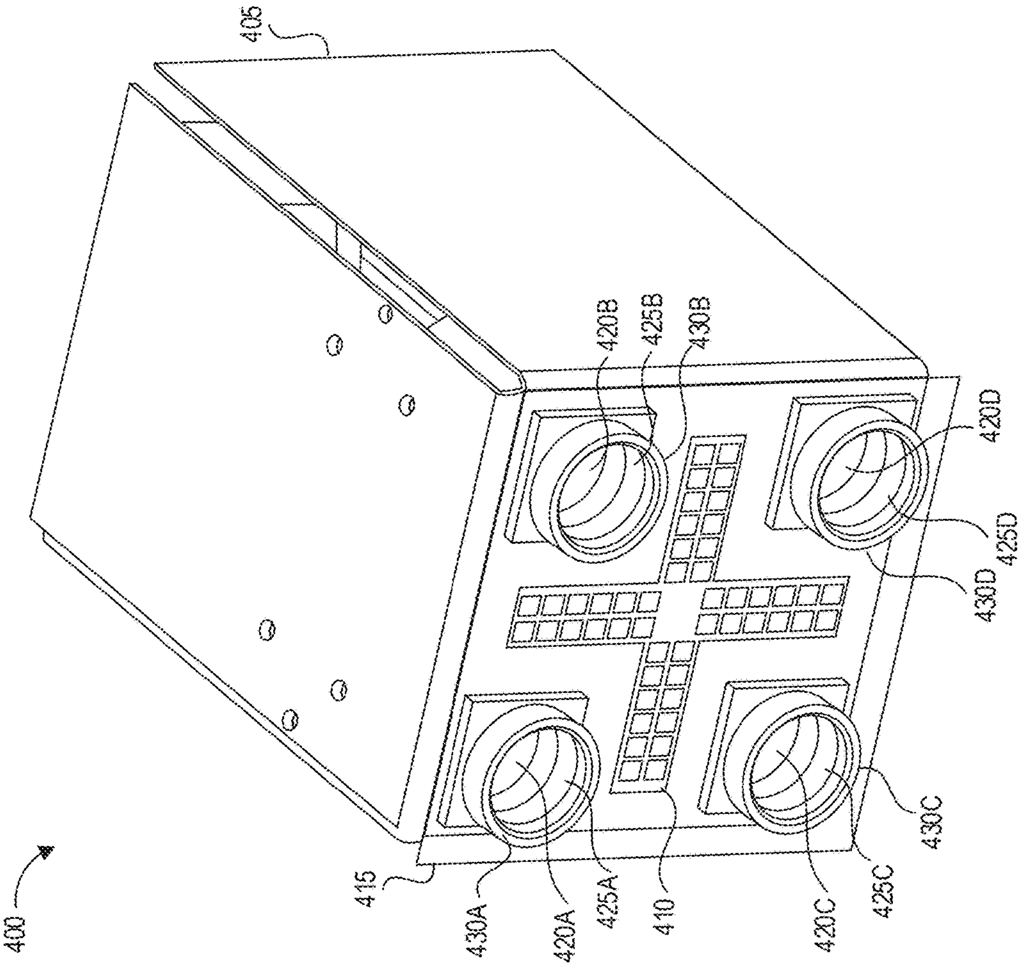
FIG. 5 depicts another embodiment of a multispectral multi-aperture imaging system, with an optical design as described with respect to FIGS. 3A and 3B.

FIG. 5 depicts another embodiment of a multispectral multi-aperture imaging system, with an optical design as described with respect to FIGS. 3A and 3B. Similar to the design of the imaging system 300, the imaging system 400 includes four light paths, here shown as openings 420A-420D having multi-bandpass filter lens groups 425A-425D, which are secured to housing 405 by retaining rings 430A-430D. The imaging system 400 also includes an illumination board 410 secured to the front face of the housing 405 between the retaining rings 430A-430D, and a diffuser 415 positioned over the illumination board 410 to assist with emitting spatially even light onto the target object.

The illumination board 410 of the system 400 includes four branches of LEDs in a cross shape, with each branch including two columns of closely-spaced LEDs. Thus, the illumination board 410 is more compact than the illumination board 310 described above, and may be suitable for use with imaging systems having smaller form factor requirements. In this example configuration, each branch includes an outermost row having one green LED and one blue LED, and moving inwards includes two rows of yellow LEDs, a row of orange LEDs, a row having one red LED and one deep red LED, and a row having one amber LED and one NIR LED. Accordingly, in this implementation the LEDs are arranged such that LEDs that emit light of longer wavelengths are in the center of the illumination board 410, while LEDs that emit light of shorter wavelengths are at the edges of the illumination board 410.

Figure 6A:
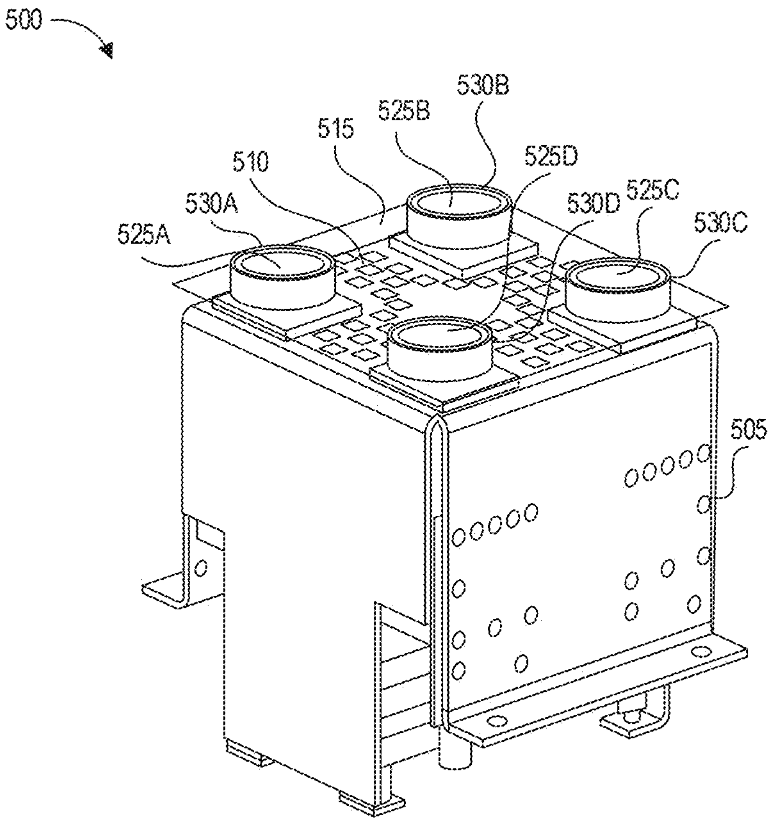
FIGS. 6A-6C depict another embodiment of a multispectral multi-aperture imaging system, with an optical design as described with respect to FIGS. 3A and 3B.
Figure 6C:
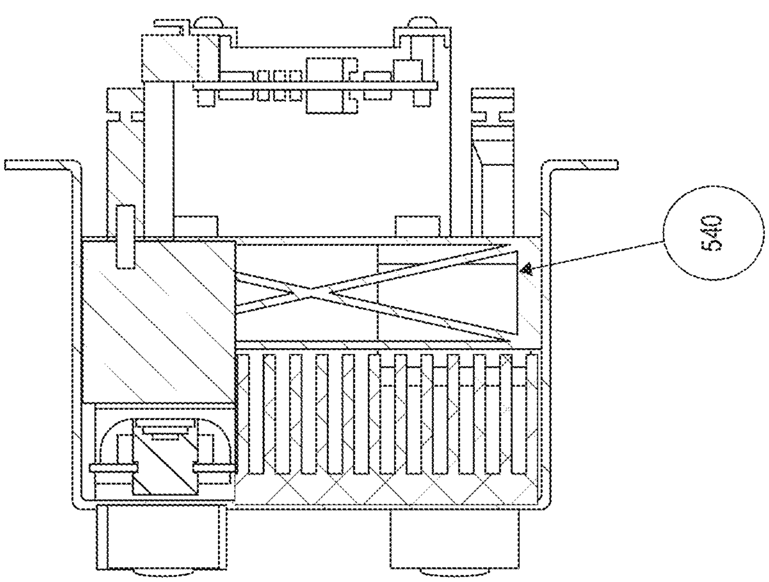
Figure 6B:
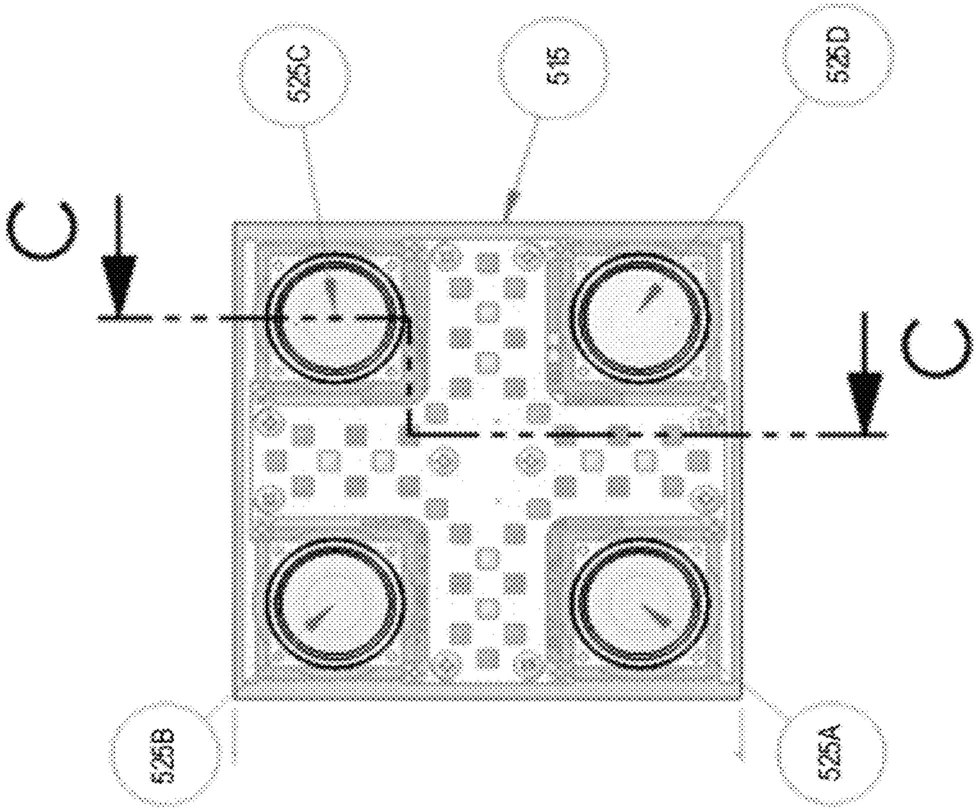

FIGS. 6A-6C depict another embodiment of a multispectral multi-aperture imaging system 500, with an optical design as described with respect to FIGS. 3A and 3B. Specifically, FIG. 6A depicts a perspective view of the imaging system 500, FIG. 6B depicts a front view of the imaging system 500, and FIG. 6C depicts a cutaway side view of the imaging system 500, cut along line C-C illustrated in FIG. 6B. The imaging system 500 includes similar components to those described above with respect to imaging system 300 (e.g., a housing 505, illumination board 510, diffusing plate 515, multi-bandpass filters 525A-525D secured over openings via retaining rings 530A-530D), but depicts a shorter form factor (e.g., in an embodiment with fewer and/or smaller embedded computing components). The system 500 also includes a direct camera-to-frame mount 540 for added rigidity and robustness of camera alignment.

Figure 7B:
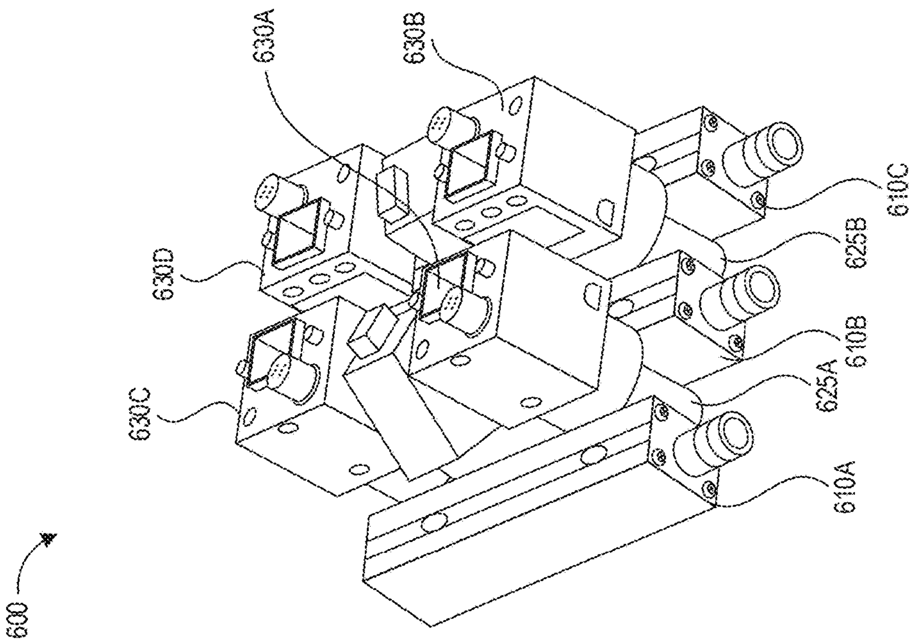
FIGS. 7A-7B depict another embodiment of a multispectral multi-aperture imaging system, with an optical design as described with respect to FIGS. 3A and 3B.
Figure 7A:
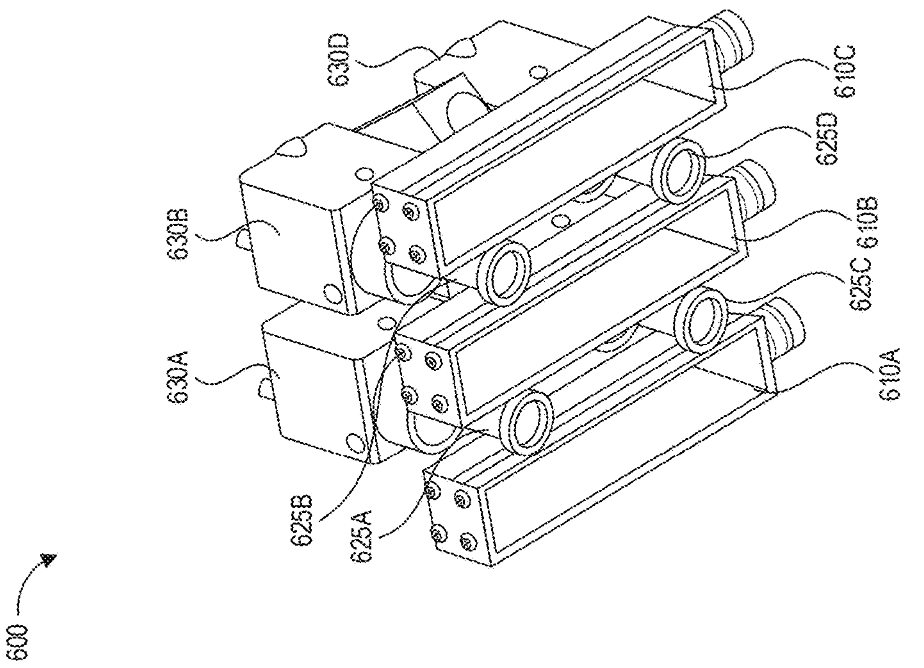

FIGS. 7A-7B depict another embodiment of a multispectral multi-aperture imaging system 600. FIGS. 7A-7B illustrate another possible arrangement of light sources 610A-610C around a multi-aperture imaging system 600. As depicted, four lens assemblies with multi-bandpass filters 625A-625D with an optical design as described with respect to FIGS. 3A-3D can be disposed in a rectangular or square configuration to provide light to four cameras 630A-630D (including image sensors). Three rectangular light emitting elements 610A-610C can be disposed parallel to one another outside of and between the lens assemblies with multi-bandpass filters 625A-625D. These can be broad-spectrum light emitting panels or arrangements of LEDs that emit discrete wavebands of light.

Figure 8B:
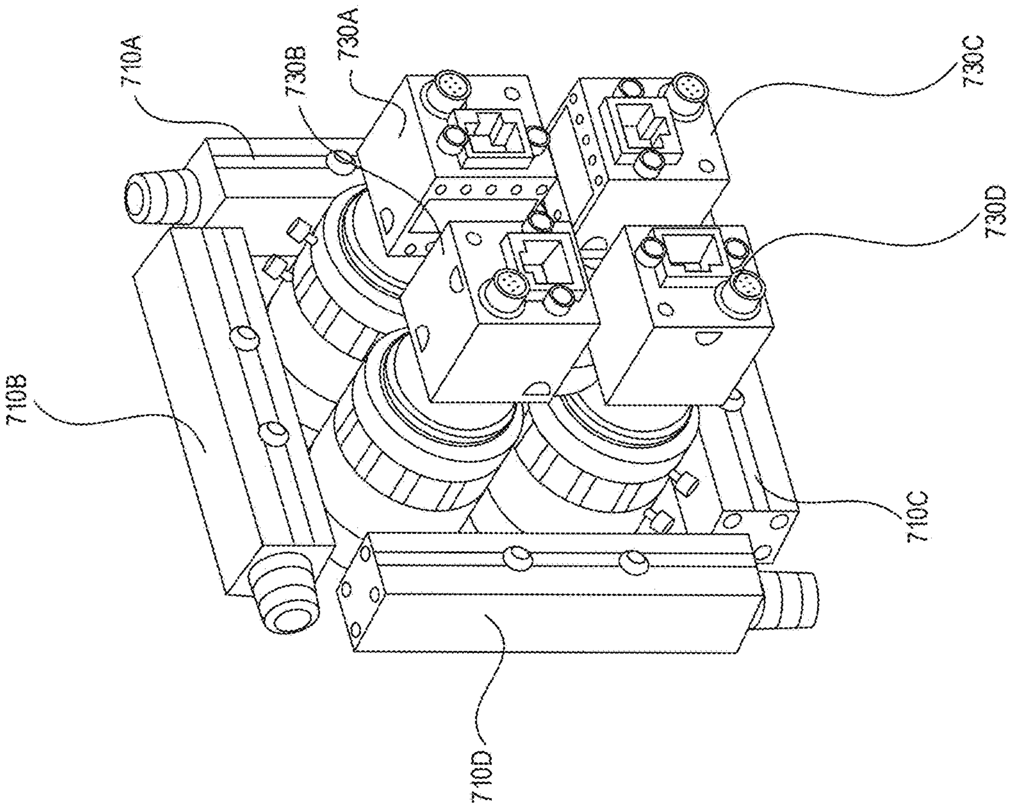
FIGS. 8A-8B depict another embodiment of a multispectral multi-aperture imaging system, with an optical design as described with respect to FIGS. 3A and 3B.
Figure 8A:
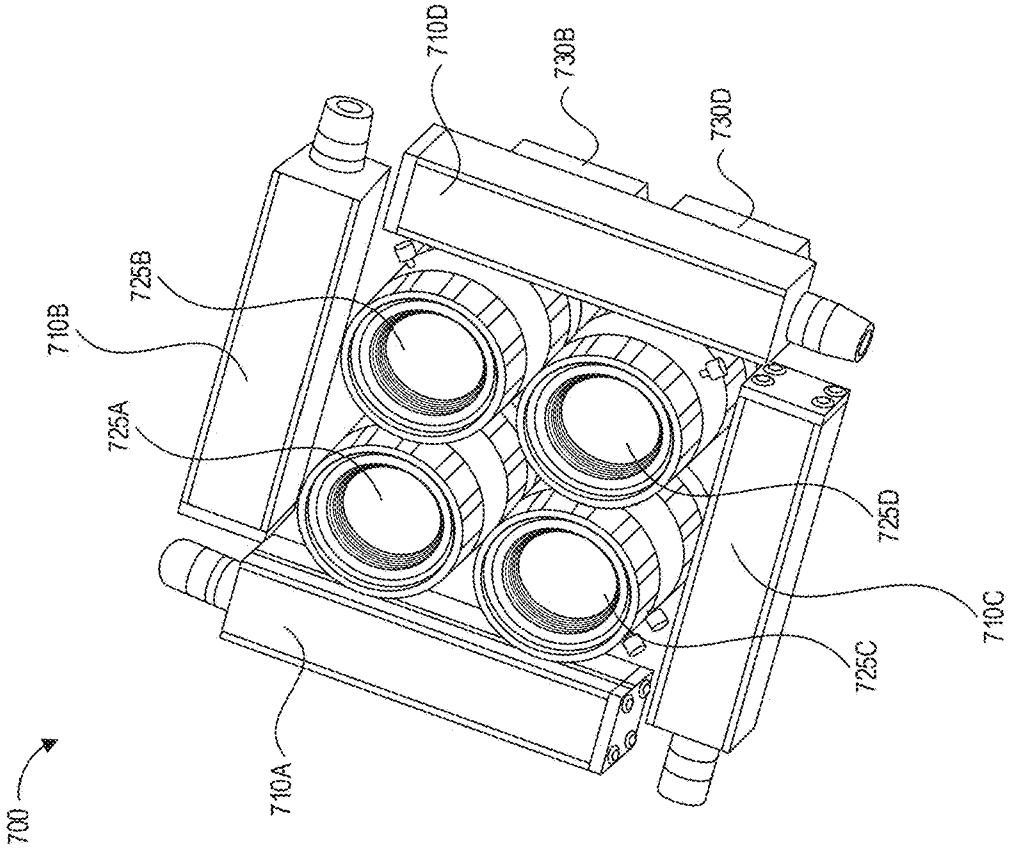

FIGS. 8A-8B depict another embodiment of a multispectral multi-aperture imaging system 700. FIGS. 8A-8B illustrate another possible arrangement of light sources 710A-710D around a multi-aperture imaging system 700. As depicted, four lens assemblies with multi-bandpass filters 725A-725D, employing an optical design as described with respect to FIGS. 3A-3D, can be disposed in a rectangular or square configuration to provide light to four cameras 730A-730D (including image sensors). The four cameras 730A-730D are illustrated in a closer example configuration which may minimize perspective differences between the lenses. Four rectangular light emitting elements 710A-710D can be positioned in a square surrounding the lens assemblies with multi-bandpass filters 725A-725D. These can be broad-spectrum light emitting panels or arrangements of LEDs that emit discrete wavebands of light.

Figure 9A:
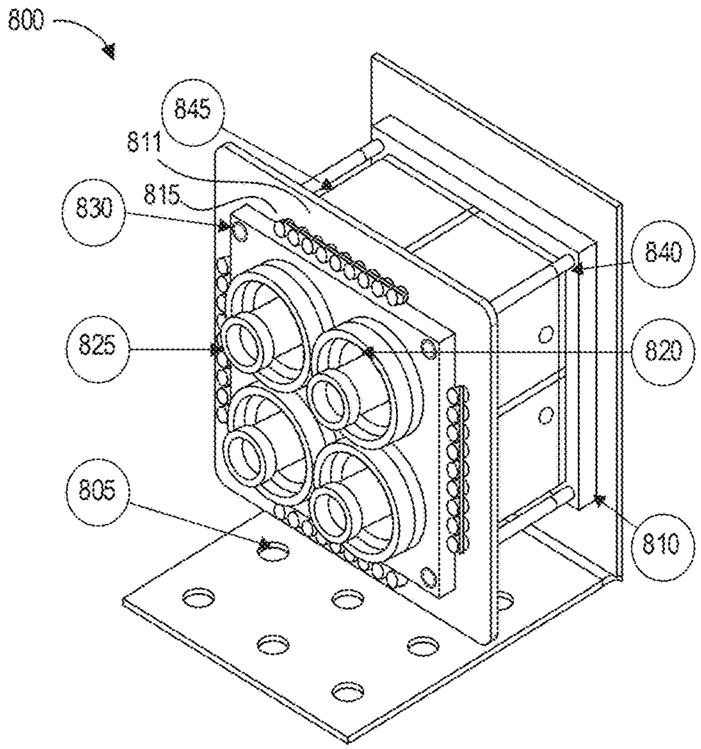
FIGS. 9A-9C depict another embodiment of a multispectral multi-aperture imaging system, with an optical design as described with respect to FIGS. 3A and 3B.
Figure 9B:
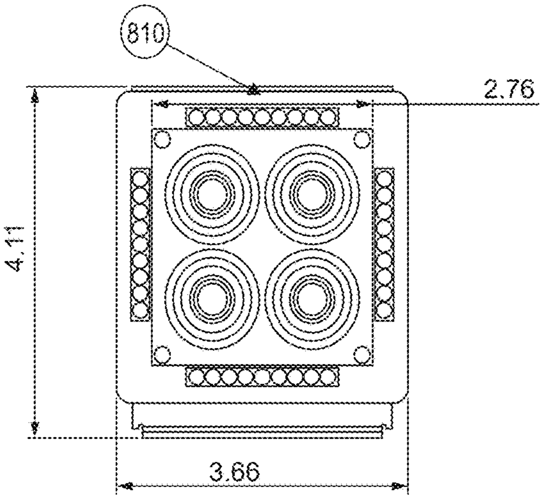
Figure 9C:
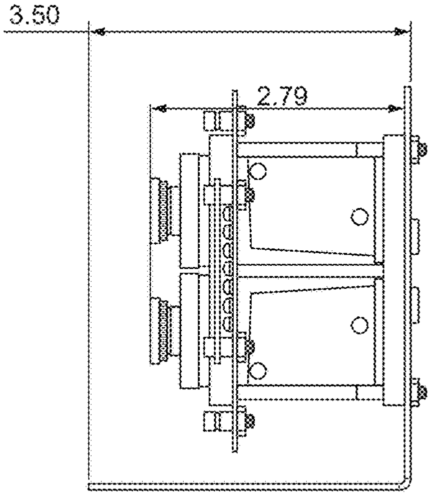

FIGS. 9A-9C depict another embodiment of a multispectral multi-aperture imaging system 800. The imaging system 800 includes a frame 805 coupled to a lens cluster frame front 830 that includes openings 820 and support structures for micro-video lenses 825, which can be provided with multi-bandpass filters using an optical design as described with respect to FIGS. 3A-3D. The micro-video lenses 825 provide light to four cameras 845 (including imaging lenses and image sensor regions) mounted on a lens cluster frame back 840. Four linear arrangements of LEDs 811 are disposed along the four sides of the lens cluster frame front 830, each provided with its own diffusing element 815. FIGS. 9B and 9C depict example dimensions in inches to show one possible size of the multi-aperture imaging system 800.

Figure 10B:
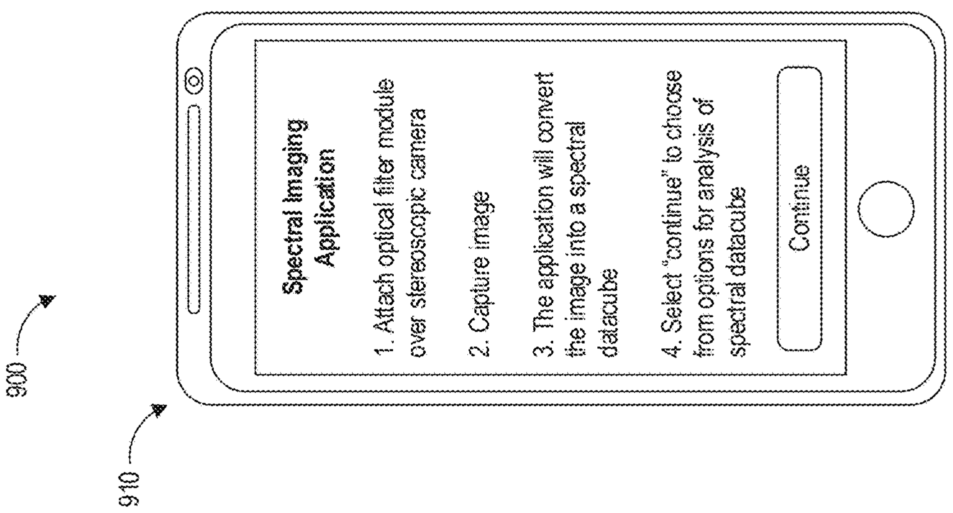
FIGS. 10A-10B depict another embodiment of a multispectral multi-aperture imaging system, with an optical design as described with respect to FIGS. 3A and 3B.
Figure 10A:
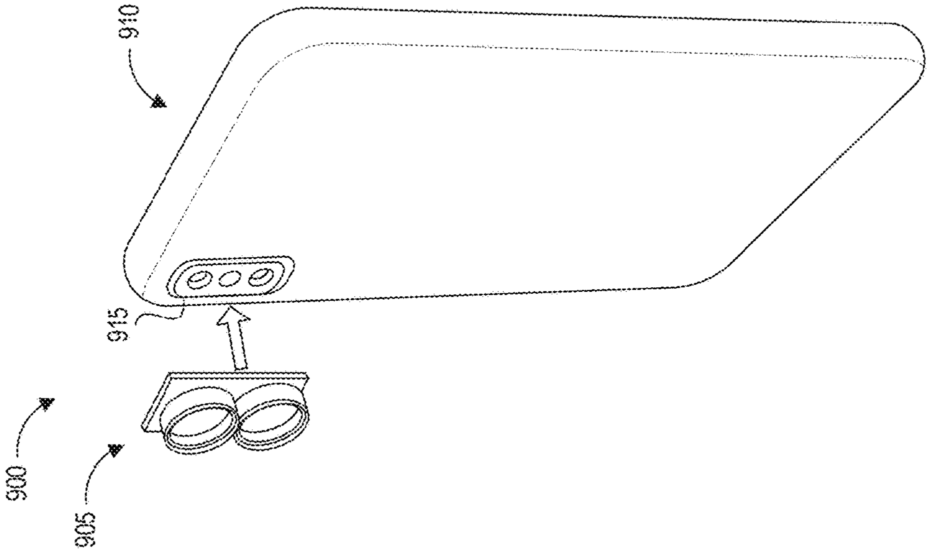

FIG. 10A depicts another embodiment of a multispectral multi-aperture imaging system 900, with an optical design as described with respect to FIGS. 3A-3D. The imaging system 900 can be implemented as a set of multi-bandpass filters 905 that are attachable over a multi-aperture camera 915 of a mobile device 910. For example, certain mobile devices 910 such as smartphones can be equipped with stereoscopic imaging systems having two openings leading to two image sensor regions. The disclosed multi-aperture spectral imaging techniques can be implemented in such devices by providing them with a suitable set of multi-bandpass filters 905 to pass multiple narrower wavebands of light to the sensor regions. Optionally, the set of multi-bandpass filters 905 can be equipped with an illuminant (such as an LED array and diffuser) that provides light at these wavebands to the object space.

The system 900 can also include a mobile application that configures the mobile device to perform the processing that generates the multispectral datacube, as well as processing the multispectral datacube (e.g., for clinical tissue classification, biometric recognition, materials analysis, or other applications). Alternatively, the mobile application may configure the device 910 to send the multispectral datacube over a network to a remote processing system, and then receive and display a result of the analysis. An example user interface 910 for such an application is shown in FIG. 10B.

Figure 11B:
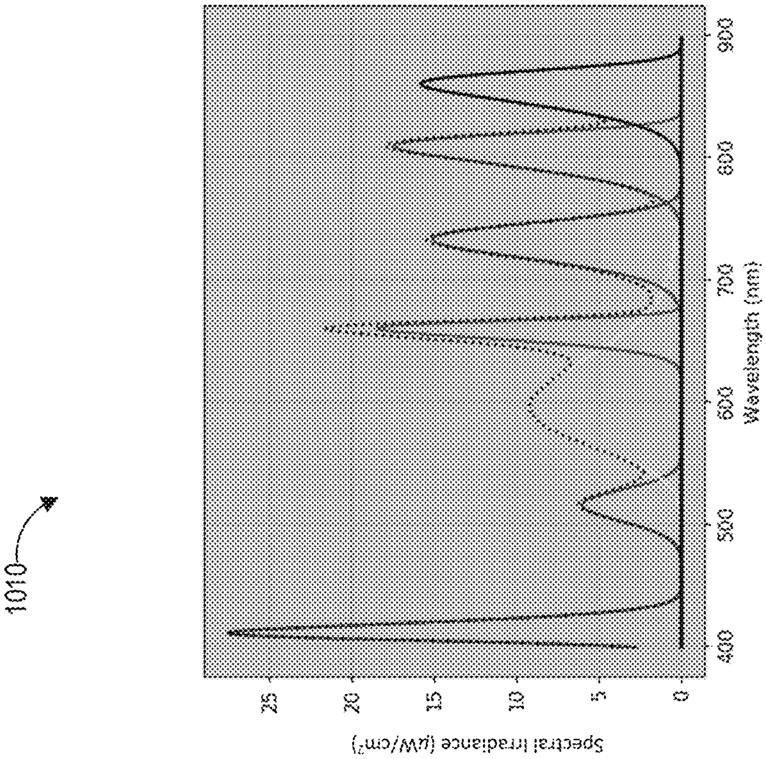
FIGS. 11A-11B depict an example set of wavebands that can be passed by the filters of the multispectral multi-aperture imaging systems of FIGS. 3A-10B.
Figure 11A:
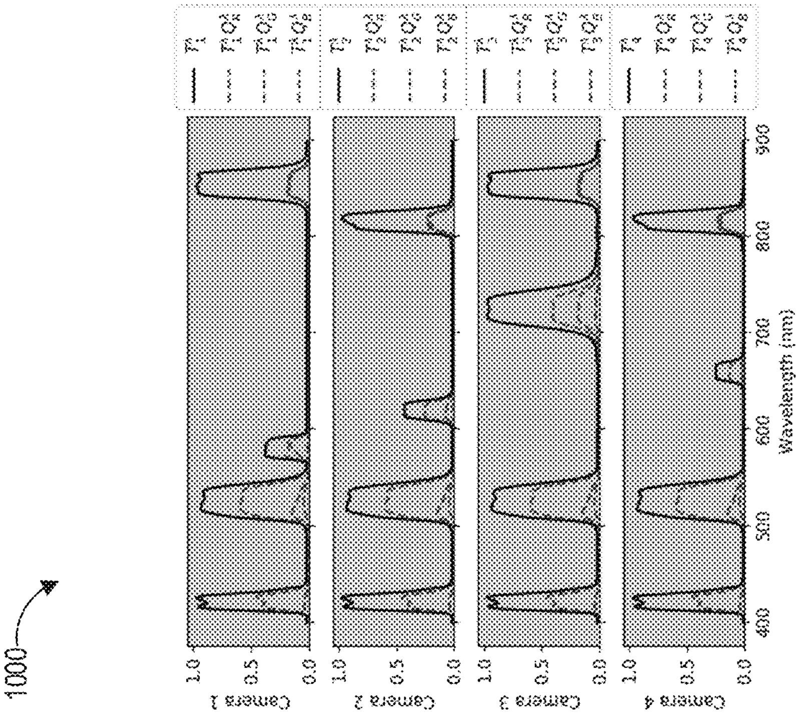

FIGS. 11A-11B depict an example set of wavebands that can be passed by the filters of four-filter implementations of the multispectral multi-aperture imaging systems of FIGS. 3A-10B, for example to an image sensor having the Bayer CFA (or another RGB or RGB-IR CFA). The spectral transmission response of wavebands as passed by the multi-bandpass filters are shown by the solid lines in the graphs 1000 of FIG. 11A and are denoted by $$T_n^\lambda,$$

where n represents the camera number, ranging from 1 through 4. The dashed lines represent the combined spectral response of $$T_n^\lambda$$

with either the spectral transmission of a green pixel, $$Q_G^\lambda,$$

a red pixel, $$Q_R^\lambda,$$

or a blue pixel, $$Q_B^\lambda,$$

that would be present in a typical Bayer CFA. These transmission curves also include the effects of quantum efficiency due to the sensor used in this example. As illustrated, this set of four cameras collectively captures eight unique channels or wavebands. Each filter passes two common wavebands (the two left-most peaks) to the respective cameras, as well as two additional wavebands. In this implementation, the first and third cameras receive light in a first shared NIR waveband (the right-most peak), and the second and fourth cameras receive light in a second shared NIR waveband (the peak second-most to the right). Each of the cameras also receives one unique waveband ranging from approximately 550 nm or 550 nm to approximately 800 nm or 800 nm. Thus, the camera can capture eight unique spectral channels using a compact configuration. A graph 1010 in FIG. 11B depicts the spectral irradiance of an LED board as described in FIG. 4E that may be used as illumination for the 4 cameras shown in FIG. 11A.

In this implementation, the eight wavebands have been selected based on producing spectral channels suitable for clinical tissue classification, and may also be optimized with respect to signal-to-noise ratio (SNR) and frame rate while limiting the number of LEDs (which introduce heat into the imaging system). The eight wavebands include a common waveband of blue light (the leftmost peak in the graphs 1000) that is passed by all four filters, because tissue (e.g., animal tissue including human tissue) exhibits higher contrast at blue wavelengths than at green or red wavelengths. Specifically, human tissue exhibits its highest contrast when imaged at a waveband centered on around 420 nm, as shown in the graphs 1000. Because the channel corresponding to the common waveband is used for disparity correction, this higher contrast can produce more accurate correction. For example in disparity correction the image processor can employ local or global methods to find a set of disparities so that a figure of merit corresponding to similarity between local image patches or images is maximized. Alternatively, the image processor can employ similar methods that minimize a figure of merit corresponding to dissimilarity. These figures of merit can be based on entropy, correlation, absolute differences, or on deep learning methods. Global methods of disparity calculation can operate iteratively, terminating when the figure of merit is stable. Local methods can be used to calculate disparity point by point, using a fixed patch in one image as an input into the figure of merit and a number of different patches, each determined by a different value of disparity under test, from the other image. All such methods can have constraints imposed on the range of disparities that are considered. These constraints can be based on knowledge of the object depth and distance, for instance. The constraints could also be imposed based on a range of gradients expected in an object. Constraints on the calculated disparities can also be imposed by projective geometry, such as the epipolar constraint. Disparity can be calculated at multiple resolutions, with the output of disparities calculated at lower resolutions acting as initial values or constraints on the disparities calculated at the next level of resolution. For instance, a disparity calculated at a resolution level of 4 pixels in one calculation can be used to set constraints of ±4 pixels in a next calculation of disparity at higher resolution. All algorithms that calculate from disparity will benefit from higher contrast, particularly if that source of contrast is correlated for all viewpoints. Generally speaking, the common waveband can be selected based on corresponding to the highest contrast imaging of the material that is expected to be imaged for a particular application.

After image capture, color separation between adjacent channels may not be perfect, and so this implementation also has an additional common waveband passed by all filters—depicted in the graphs 1000 as the green waveband adjacent to the blue waveband. This is because blue color filter pixels are sensitive to retions of the green spectrum due to its broad spectral bandpass. This typically manifests as spectral overlap, which may also be characterized as intentional crosstalk, between adjacent RGB pixels. This overlap enables the spectral sensitivity of color cameras to be similar to the spectral sensitivity of a human retina, such that the resultant color space is qualitatively similar to human vision. Accordingly, having a common green channel can enable separation of the portion of the signal generated by blue photodiodes that truly corresponds to received blue light, by separating out the portion of the signal due to green light. This can be accomplished using spectral unmixing algorithms that factor in the transmittance (shown in the legend by T with a solid black line) of the multi-band pass filter, the transmittance of the corresponding CFA color filter (shown in the legend by Q with dashed red, green, and blue lines). It will be appreciated that some implementations may use red light as a common waveband, and in such instances a second common channel may not be necessary.

Figure 12:
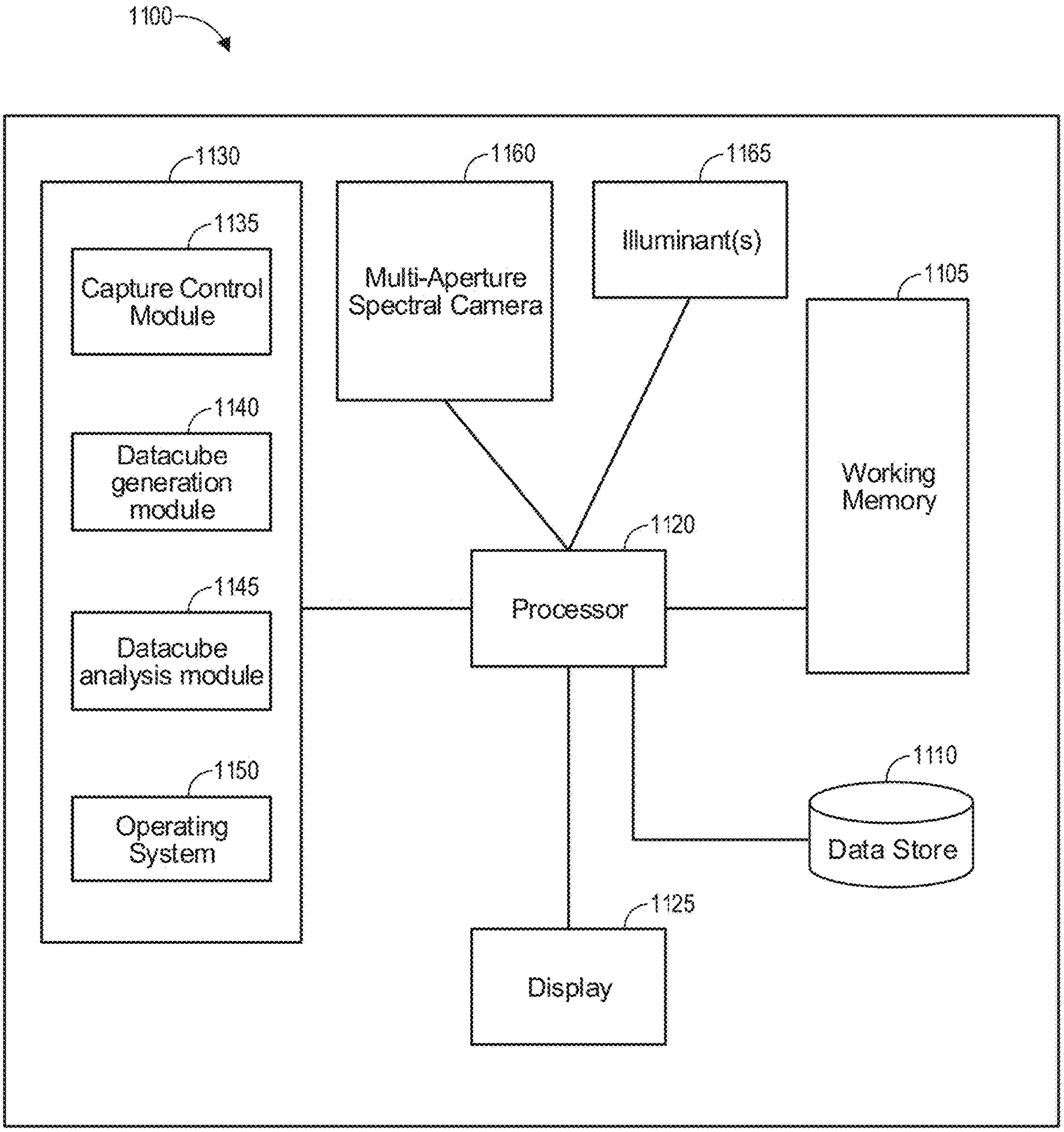
FIG. 12 depicts a schematic block diagram of an imaging system that can be used for the multispectral multi-aperture imaging systems of FIGS. 3A-10B.

FIG. 12 illustrates a high-level block diagram of an example compact imaging system 1100 with high resolution spectral imaging capabilities, the system 1100 having a set of components including a processor 1120 linked to an multi-aperture spectral camera 1160 and illuminant(s) 1165. A working memory 1105, storage 1110, electronic display 1125, and memory 1130 are also in communication with the processor 1120. As described herein, the system 1100 may capture a greater number of image channels than there are different colors of filters in the CFA of the image sensor by using different multi-bandpass filters placed over different openings of the multi-aperture spectral camera 1160.

System 1100 may be a device such as cell phone, digital camera, tablet computer, personal digital assistant, or the like. System 1100 may also be a more stationary device such as a desktop personal computer, video conferencing station, or the like that uses an internal or external camera for capturing images. System 1100 can also be a combination of an image capture device and a separate processing device receiving image data from the image capture device. A plurality of applications may be available to the user on system 1100. These applications may include traditional photographic applications, capture of still images and video, dynamic color correction applications, and brightness shading correction applications, among others.

The image capture system 1100 includes the multi-aperture spectral camera 1160 for capturing images. The multi-aperture spectral camera 1160 can be, for example, any of the devices of FIGS. 3A-10B. The multi-aperture spectral camera 1160 may be coupled to the processor 1120 to transmit captured images in different spectral channels and from different sensor regions to the image processor 1120. The illuminant(s) 1165 can also be controlled by the processor to emit light at certain wavelengths during certain exposures, as described in more detail below. The image processor 1120 may be configured to perform various operations on a received captured image in order to output a high quality, disparity corrected multispectral datacube.

Processor 1120 may be a general purpose processing unit or a processor specially designed for imaging applications. As shown, the processor 1120 is connected to a memory 1130 and a working memory 1105. In the illustrated embodiment, the memory 1130 stores a capture control module 1135, datacube generation module 1140, datacube analysis module 1145, and operating system 1150. These modules include instructions that configure the processor to perform various image processing and device management tasks. Working memory 1105 may be used by processor 1120 to store a working set of processor instructions contained in the modules of memory 1130. Alternatively, working memory 1105 may also be used by processor 1120 to store dynamic data created during the operation of device 1100.

As mentioned above, the processor 1120 is configured by several modules stored in the memory 1130. The capture control module 1135 includes instructions that configure the processor 1120 to adjust the focus position of the multi-aperture spectral camera 1160, in some implementations. The capture control module 1135 also includes instructions that configure the processor 1120 to capture images with the multi-aperture spectral camera 1160, for example multispectral images captured at different spectral channels as well as PPG images captured at the same spectral channel (e.g., a NIR channel). Non-contact PPG imaging normally uses near-infrared (NIR) wavelengths as illumination to take advantage of the increased photon penetration into the tissue at this wavelength. Therefore, processor 1120, along with capture control module 1135, multi-aperture spectral camera 1160, and working memory 1105 represent one means for capturing a set of spectral images and/or a sequence of images.

The datacube generation module 1140 includes instructions that configure the processor 1120 to generate a multispectral datacube based on intensity signals received from the photodiodes of different sensor regions. For example, the datacube generation module 1140 can estimate a disparity between the same regions of an imaged object based on a spectral channel corresponding to the common waveband passed by all multi-bandpass filters, and can use this disparity to register all spectral images across all captured channels to one another (e.g., such that the same point on the object is represented by substantially the same (x,y) pixel location across all spectral channels). The registered images collectively form the multispectral datacube, and the disparity information may be used to determine depths of different imaged objects, for example a depth difference between healthy tissue and a deepest location within a wound site. In some embodiments, the datacube generation module 1140 may also perform spectral unmixing to identify which portions of the photodiode intensity signals correspond to which passed wavebands, for example based on spectral unmixing algorithms that factor in filter transmittances and sensor quantum efficiency.

The datacube analysis module 1145 can implement various techniques to analyze the multispectral datacube generated by the datacube generation module 1140, depending upon the application. For example, some implementations of the datacube analysis module 1145 can provide the multispectral datacube (and optionally depth information) to a machine learning model trained to classify each pixel according to a certain state. These states may be clinical states in the case of tissue imaging, for example burn states (e.g., first degree burn, second degree burn, third degree burn, or healthy tissue categories), wound states (e.g., hemostasis, inflammation, proliferation, remodeling or healthy skin categories), healing potential (e.g., a score reflecting the likelihood that the tissue will heal from a wounded state, with or without a particular therapy), perfusion states, cancerous states, or other wound-related tissue states. The datacube analysis module 1145 can also analyze the multispectral datacube for biometric recognition and/or materials analysis.

Operating system module 1150 configures the processor 1120 to manage the memory and processing resources of the system 1100. For example, operating system module 1150 may include device drivers to manage hardware resources such as the electronic display 1125, storage 1110, multi-aperture spectral camera 1160, or illuminant(s) 1165. Therefore, in some embodiments, instructions contained in the image processing modules discussed above may not interact with these hardware resources directly, but instead interact through standard subroutines or APIs located in operating system component 1150. Instructions within operating system 1150 may then interact directly with these hardware components.

The processor 1120 may be further configured to control the display 1125 to display the captured images and/or a result of analyzing the multispectral datacube (e.g., a classified image) to a user. The display 1125 may be external to an imaging device including the multi-aperture spectral camera 1160 or may be part of the imaging device. The display 1125 may also be configured to provide a view finder for a user prior to capturing an image. The display 1125 may comprise an LCD or LED screen, and may implement touch sensitive technologies.

Processor 1120 may write data to storage module 1110, for example data representing captured images, multispectral datacubes, and datacube analysis results. While storage module 1110 is represented graphically as a traditional disk device, those with skill in the art would understand that the storage module 1110 may be configured as any storage media device. For example, the storage module 1110 may include a disk drive, such as a floppy disk drive, hard disk drive, optical disk drive or magneto-optical disk drive, or a solid state memory such as a FLASH memory, RAM, ROM, and/or EEPROM. The storage module 1110 can also include multiple memory units, and any one of the memory units may be configured to be within the image capture device 1100, or may be external to the image capture system 1100. For example, the storage module 1110 may include a ROM memory containing system program instructions stored within the image capture system 1100. The storage module 1110 may also include memory cards or high speed memories configured to store captured images which may be removable from the camera.

Although FIG. 12 depicts a system comprising separate components to include a processor, imaging sensor, and memory, one skilled in the art would recognize that these separate components may be combined in a variety of ways to achieve particular design objectives. For example, in an alternative embodiment, the memory components may be combined with processor components to save cost and improve performance.

Additionally, although FIG. 12 illustrates two memory components-memory component 1130 comprising several modules and a separate memory 1105 comprising a working memory-one with skill in the art would recognize several embodiments utilizing different memory architectures. For example, a design may utilize ROM or static RAM memory for the storage of processor instructions implementing the modules contained in memory 1130. Alternatively, processor instructions may be read at system startup from a disk storage device that is integrated into system 1100 or connected via an external device port. The processor instructions may then be loaded into RAM to facilitate execution by the processor. For example, working memory 1105 may be a RAM memory, with instructions loaded into working memory 1105 before execution by the processor 1120.

Overview of Example Image Processing Techniques

Figure 13:
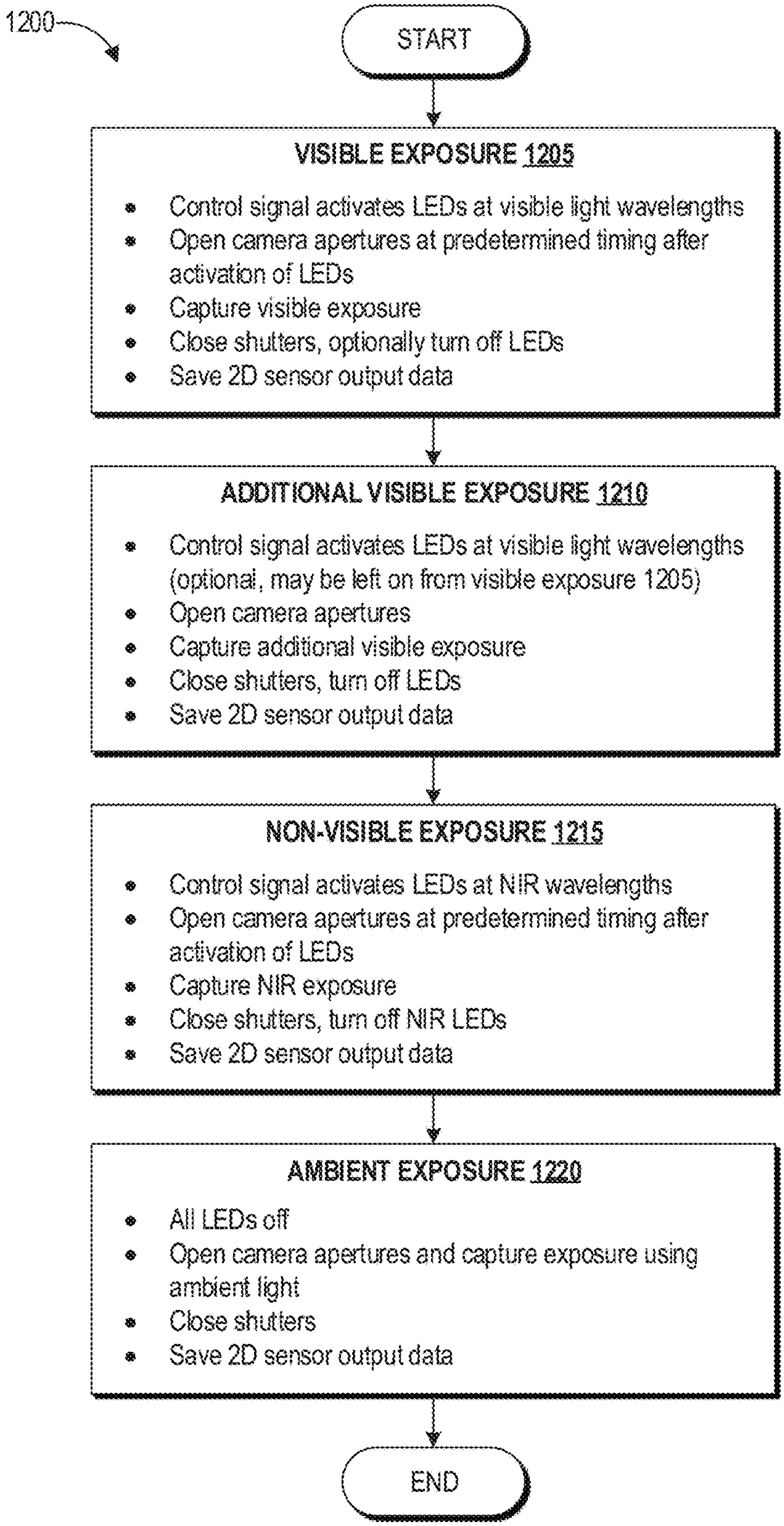
FIG. 13 is a flowchart of an example process for capturing image data using the multispectral multi-aperture imaging systems of FIGS. 3A-10B.

FIG. 13 is a flowchart of an example process 1200 for capturing image data using the multispectral multi-aperture imaging systems of FIGS. 3A-10B and 12. FIG. 13 depicts four example exposures that can be used to generate a multispectral datacube as described herein—a visible exposure 1205, an additional visible exposure 1210, a non-visible exposure 1215, and an ambient exposure 1220. It will be appreciated that these may be captured in any order, and some exposures may be optionally removed from or added to a particular workflow as described below. Further, the process 1200 is described with reference to the wavebands of FIGS. 11A and 11B, however similar workflows can be implemented using image data generated based on other sets of wavebands. Additionally, flat field correction may further be implemented in accordance with various known flat field correction techniques, to improve image acquisition and/or disparity correction in various embodiments.

For the visible exposure 1205, LEDs of first five peaks (the left five peaks corresponding to visible light in the graphs 1000 of FIG. 11A) can be turned on by a control signal to the illumination board. The wave of light output may need to stabilize, at a time specific to particular LEDs, for example 10 ms. The capture control module 1135 can begin the exposure of the four cameras after this time and can continue this exposure for a duration of around 30 ms, for example. Thereafter, the capture control module 1135 can cease the exposure and pull the data off of the sensor regions (e.g., by transferring raw photodiode intensity signals to the working memory 1105 and/or data store 1110). This data can include a common spectral channel for use in disparity correction as described herein.

In order to increase the SNR, some implementations can capture the additional visible exposure 1210 using the same process described for the visible exposure 1205. Having two identical or near-identical exposures can increase the SNR to yield more accurate analysis of the image data. However, this may be omitted in implementations where the SNR of a single image is acceptable. A duplicate exposure with the common spectral channel may also enable more accurate disparity correction in some implementations.

Some implementations can also capture a non-visible exposure 1215 corresponding to NIR or IR light. For example, the capture control module 1135 can activate two different NIR LEDs corresponding to the two NIR channels shown in FIG. 11A. The wave of light output may need to stabilize, at a time specific to particular LEDs, for example 10 ms. The capture control module 1135 can begin the exposure of the four cameras after this time and continue this exposure for a duration of around 30 ms, for example. Thereafter, the capture control module 1135 can cease the exposure and pull the data off of the sensor regions (e.g., by transferring raw photodiode intensity signals to the working memory 1105 and/or data store 1110). In this exposure, there may be no common waveband passed to all sensor regions, as it can safely be assumed that there is no change in the shape or positioning of the object relative to the exposures 1205, 1210 and, thus previously computed disparity values can be used to register the NIR channels.

In some implementations, multiple exposures can be captured sequentially to generate PPG data representing the change in shape of a tissue site due to pulsatile blood flow. These PPG exposures may be captured at a non-visible wavelength in some implementations. Although the combination of PPG data with multispectral data may increase the accuracy of certain medical imaging analyses, the capture of PPG data can also introduce additional time into the image capture process. This additional time can introduce errors due to movement of the handheld imager and/or object, in some implementations. Thus, certain implementations may omit capture of PPG data.

Some implementations can additionally capture the ambient exposure 1220. For this exposure, all LEDs can be turned off to capture an image using ambient illumination (e.g., sunlight, light from other illuminant sources). The capture control module 1135 can begin the exposure of the four cameras after this time and can keep the exposure ongoing for a desired duration of, for example, around 30 ms. Thereafter, the capture control module 1135 can cease the exposure and pull the data off of the sensor regions (e.g., by transferring raw photodiode intensity signals to the working memory 1105 and/or data store 1110). The intensity values of the ambient exposure 1220 can be subtracted from the values of the visible exposure 1205 (or the visible exposure 1205 corrected for SNR by the second exposure 1210) and also from the non-visible exposure 1215 in order to remove the influence of ambient light from the multispectral datacube. This can increase the accuracy of downstream analysis by isolating the portion of the generated signals that represent light emitted by the illuminants and reflected from the object/tissue site. Some implementations may omit this step if analytical accuracy is sufficient using just the visible 1205, 1210 and non-visible 1215 exposures.

It will be appreciated that the particular exposure times listed above are examples of one implementation, and that in other implementations exposure time can vary depending upon the image sensor, illuminant intensity, and imaged object.

Figure 14:
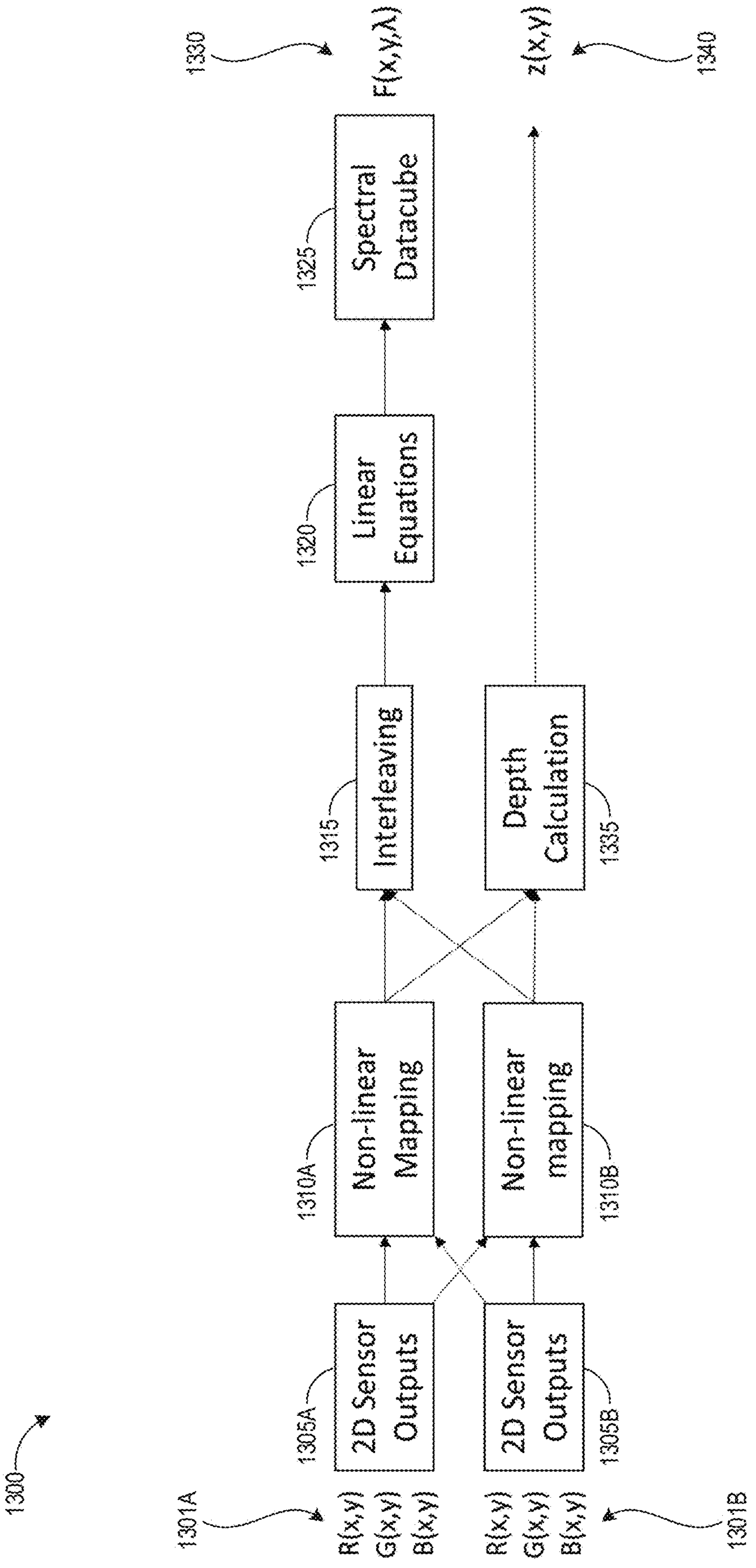
FIG. 14 depicts a schematic block diagram of a workflow for processing image data, for example image data captured using the process of FIG. 13 and/or using the multispectral multi-aperture imaging systems of FIGS. 3A-10B.

FIG. 14 depicts a schematic block diagram of a workflow 1300 for processing image data, for example image data captured using the process 1200 of FIG. 13 and/or using the multispectral multi-aperture imaging systems of FIGS. 3A-10B and 12. The workflow 1300 shows the output of two RGB sensor regions 1301A, 1301B, however the workflow 1300 can be extended to greater numbers of sensor regions and sensor regions corresponding to different CFA color channels.

The RGB sensor outputs from the two sensor regions 1301A, 1301B are stored at the 2D sensor outputs modules 1305A, 1305B, respectively. The values of both sensor regions are sent to the non-linear mapping modules 1310A, 1310B, which can perform disparity correction by identifying disparity between the captured images using the common channel and then applying this determined disparity across all channels to register all spectral images to one another.

The outputs of both non-linear mapping modules 1310A, 1310B are then provided to the depth calculation module 1335, which can compute a depth of a particular region of interest in the image data. For example, the depth may represent the distance between the object and the image sensor. In some implementations, multiple depth values can be computed and compared to determine the depth of the object relative to something other than the image sensor. For example, a greatest depth of a wound bed can be determined, as well as a depth (greatest, lowest, or average) of healthy tissue surrounding the wound bed. By subtracting the depth of the healthy tissue from the depth of the wound bed, the deepest depth of the wound can be determined. This depth comparison can additionally be performed at other points in the wound bed (e.g., all or some predetermined sampling) in order to build a 3D map of the depth of the wound at various points (shown in FIG. 14 as z(x,y) where z would be a depth value). In some embodiments, greater disparity may improve the depth calculation, although greater disparity may also result in more computationally intensive algorithms for such depth calculations.

The outputs of both non-linear mapping modules 1310A, 1310B are also provided to the linear equations module 1320, which can treat the sensed values as set of linear equations for spectral unmixing. One implementation can use the Moore-Penrose pseudo-inverse equation as a function of at least sensor quantum efficiency and filter transmittance values to compute actual spectral values (e.g., intensity of light at particular wavelengths that were incident at each (x,y) image point). This can be used in implementations that require high accuracy, such as clinical diagnostics and other biological applications. Application of the spectral unmixing can also provide an estimate of photon flux and SNR.

Based on the disparity-corrected spectral channel images and the spectral unmixing, the workflow 1300 can generate a spectral datacube 1325, for example in the illustrated format of F(x,y,λ) where F represents the intensity of light at a specific (x,y) image location at a specific wavelength or waveband λ.

Figure 15:
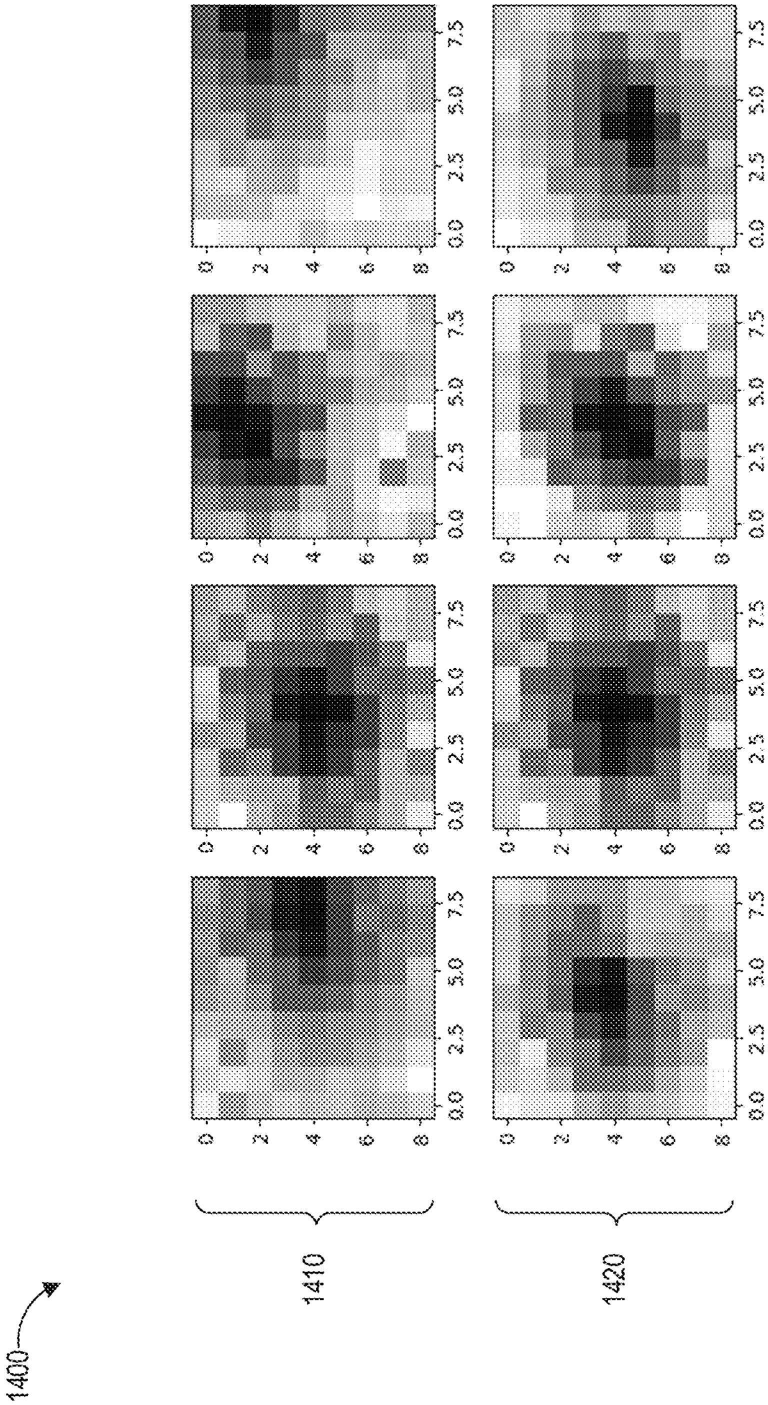
FIG. 15 graphically depicts disparity and disparity correction for processing image data, for example image data captured using the process of FIG. 13 and/or using the multispectral multi-aperture imaging systems of FIGS. 3A-10B.

FIG. 15 graphically depicts disparity and disparity correction for processing image data, for example image data captured using the process of FIG. 13 and/or using the multispectral multi-aperture imaging systems of FIGS. 3A-10B and 12. The first set of images 1410 show image data of the same physical location on an object as captured by four different sensor regions. As illustrated, this object location is not in the same location across the raw images, based on the (x,y) coordinate frames of the photodiode grids of the image sensor regions. The second set of images 1420 shows that same object location after disparity correction, which is now in the same (x,y) location in the coordinate frame of the registered images. It will be appreciated that such registration may involve cropping certain data from edge regions of the images that do not entirely overlap with one another.

Figure 16:
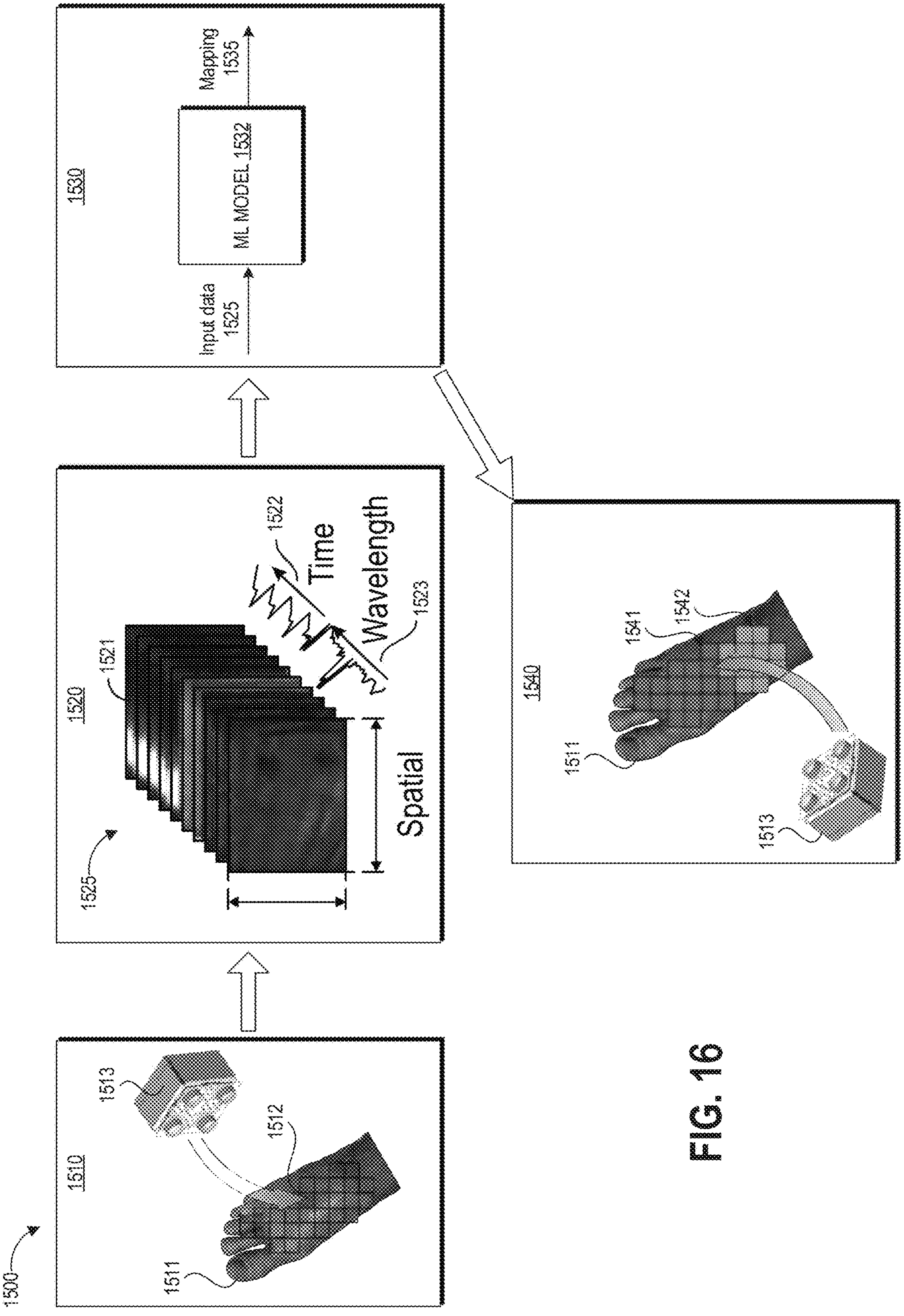
FIG. 16 graphically depicts a workflow for performing pixel-wise classification on multispectral image data, for example image data captured using the process of FIG. 13, processed according to FIGS. 14 and 15, and/or using the multispectral multi-aperture imaging systems of FIGS. 3A-10B.

FIG. 16 graphically depicts a workflow 1500 for performing pixel-wise classification on multispectral image data, for example image data captured using the process of FIG. 13, processed according to FIGS. 14 and 15, and/or using the multispectral multi-aperture imaging systems of FIGS. 3A-10B and 12.

At block 1510, the multispectral multi-aperture imaging system 1513 can capture image data representing physical points 1512 on an object 1511. In this example, the object 1511 includes tissue of a patient that has a wound. A wound can comprise a burn, a diabetic ulcer (e.g., a diabetic foot ulcer), a non-diabetic ulcer (e.g., pressure ulcers or slow-healing wounds), a chronic ulcer, a post-surgical incision, an amputation site (before or after the amputation procedure), a cancerous lesion, or damaged tissue. Where PPG information is included, the disclosed imaging systems provide a method to assess pathologies involving changes to tissue blood flow and pulse rate including: tissue perfusion; cardiovascular health; wounds such as ulcers; peripheral arterial disease, and respiratory health.

At block 1520, the data captured by the multispectral multi-aperture imaging system 1513 can be processed into a multispectral datacube 1525 having a number of different wavelengths 1523, and, optionally, a number of different images at the same wavelength corresponding to different times (PPG data 1522). For example, the image processor 1120 can be configured by the datacube generation module 1140 to generate the multispectral datacube 1525 according to the workflow 1300. Some implementations may also associated depth values with various points along the spatial dimensions, as described above.

At block 1530, the multispectral datacube 1525 can be analyzed as input data 1525 into a machine learning model 1532 to generate a classified mapping 1535 of the imaged tissue. The classified mapping can assign each pixel in the image data (which, after registration, represent specific points on the imaged object 1511) to a certain tissue classification, or to a certain healing potential score. The different classifications and scores can be represented using visually distinct colors or patterns in the output classified image. Thus, even though a number of images are captured of the object 1511, the output can be a single image of the object (e.g., a typical RGB image) overlaid with visual representations of pixel-wise classification.

The machine learning model 1532 can be an artificial neural network in some implementations. Artificial neural networks are artificial in the sense that they are computational entities, inspired by biological neural networks but modified for implementation by computing devices. Artificial neural networks are used to model complex relationships between inputs and outputs or to find patterns in data, where the dependency between the inputs and the outputs cannot be easily ascertained. A neural network typically includes an input layer, one or more intermediate ("hidden") layers, and an output layer, with each layer including a number of nodes. The number of nodes can vary between layers. A neural network is considered "deep" when it includes two or more hidden layers. The nodes in each layer connect to some or all nodes in the subsequent layer and the weights of these connections are typically learnt from data during the training process, for example through backpropagation in which the network parameters are tuned to produce expected outputs given corresponding inputs in labeled training data. Thus, an artificial neural network is an adaptive system that is configured to change its structure (e.g., the connection configuration and/or weights) based on information that flows through the network during training, and the weights of the hidden layers can be considered as an encoding of meaningful patterns in the data.

A fully connected neural network is one in which each node in the input layer is connected to each node in the subsequent layer (the first hidden layer), each node in that first hidden layer is connected in turn to each node in the subsequent hidden layer, and so on until each node in the final hidden layer is connected to each node in the output layer.

A CNN is a type of artificial neural network, and like the artificial neural network described above, a CNN is made up of nodes and has learnable weights. However, the layers of a CNN can have nodes arranged in three dimensions: width, height, and depth, corresponding to the 2×2 array of pixel values in each video frame (e.g., the width and height) and to the number of video frames in the sequence (e.g., the depth). The nodes of a layer may only be locally connected to a small region of the width and height layer before it, called a receptive field. The hidden layer weights can take the form of a convolutional filter applied to the receptive field. In some embodiments, the convolutional filters can be two-dimensional, and thus, convolutions with the same filter can be repeated for each frame (or convolved transformation of an image) in the input volume or for designated subset of the frames. In other embodiments, the convolutional filters can be three-dimensional and thus extend through the full depth of nodes of the input volume. The nodes in each convolutional layer of a CNN can share weights such that the convolutional filter of a given layer is replicated across the entire width and height of the input volume (e.g., across an entire frame), reducing the overall number of trainable weights and increasing applicability of the CNN to data sets outside of the training data. Values of a layer may be pooled to reduce the number of computations in a subsequent layer (e.g., values representing certain pixels may be passed forward while others are discarded), and further along the depth of the CNN pool masks may reintroduce any discarded values to return the number of data points to the previous size. A number of layers, optionally with some being fully connected, can be stacked to form the CNN architecture.

During training, an artificial neural network can be exposed to pairs in its training data and can modify its parameters to be able to predict the output of a pair when provided with the input. For example, the training data can include multispectral datacubes (the input) and classified mappings (the expected output) that have been labeled, for example by a clinician who has designated areas of the wound that correspond to certain clinical states, and/or with healing (1) or non-healing (0) labels sometime after initial imaging of the wound when actual healing is known. Other implementations of the machine learning model 1532 can be trained to make other types of predictions, for example the likelihood of a wound healing to a particular percentage area reduction over a specified time period (e.g., at least 50% area reduction within 30 days) or wound states such as, hemostasis, inflammation, proliferation, remodeling or healthy skin categories. Some implementations may also incorporate patient metrics into the input data to further increase classification accuracy, or may segment training data based on patient metrics to train different instances of the machine learning model 1532 for use with other patients having those same patient metrics. Patient metrics can include textual information or medical history or aspects thereof describing characteristics of the patient or the patient's health status, for example the area of a wound, lesion, or ulcer, the BMI of the patient, the diabetic status of the patient, the existence of peripheral vascular disease or chronic inflammation in the patient, the number of other wounds the patient has or has had, whether the patient is or has recently taken immunosuppressant drugs (e.g., chemotherapy) or other drugs that positively or adversely affect wound healing rate, HbA1c, chronic kidney failure stage IV, type II vs type I diabetes, chronic anemia, asthma, drug use, smoking status, diabetic neuropathy, deep vein thrombosis, previous myocardial infarction, transient ischemic attacks, or sleep apnea or any combination thereof. These metrics can be converted into a vector representation through appropriate processing, for example through word-to-vec embeddings, a vector having binary values representing whether the patient does or does not have the patient metric (e.g., does or does not have type I diabetes), or numerical values representing a degree to which the patient has each patient metric.

At block 1540, the classified mapping 1535 can be output to a user. In this example, the classified mapping 1535 uses a first color 1541 to denote pixels classified according to a first state and uses a second color 1542 to denote pixels classified according to a second state. The classification and resulting classified mapping 1535 may exclude background pixels, for example based on object recognition, background color identification, and/or depth values. As illustrated, some implementations of the multispectral multi-aperture imaging system 1513 can project the classified mapping 1535 back on to the tissue site. This can be particularly beneficial when the classified mapping includes a visual representation of a recommended margin and/or depth of excision.

These methods and systems may provide assistance to clinicians and surgeons in the process of dermal wound management, such as burn excision, amputation level, lesion removal, and wound triage decisions. Alternatives described herein can be used to identify and/or classify the severity of decubitus ulcers, hyperaemia, limb deterioration, Raynaud's Phenomenon, scleroderma, chronic wounds, abrasions, lacerations, hemorrhaging, rupture injuries, punctures, penetrating wounds, skin cancers, such as basal cell carcinoma, squamous cell carcinoma, melanoma, actinic keratosis, or any type of tissue change, wherein the nature and quality of the tissue differs from a normal state. The devices described herein may also be used to monitor healthy tissue, facilitate and improve wound treatment procedures, for example allowing for a faster and more refined approach for determining the margin for debridement, and evaluate the progress of recovery from a wound or disease, especially after a treatment has been applied. In some alternatives described herein, devices are provided that allow for the identification of healthy tissue adjacent to wounded tissue, the determination of an excision margin and/or depth, the monitoring of the recovery process after implantation of a prosthetic, such as a left ventricular assist device, the evaluation of the viability of a tissue graft or regenerative cell implant, or the monitoring of surgical recovery, especially after reconstructive procedures. Moreover, alternatives described herein may be used to evaluate the change in a wound or the generation of healthy tissue after a wound, in particular, after introduction of a therapeutic agent, such as a steroid, hepatocyte growth factor, fibroblast growth factor, an antibiotic, or regenerative cells, such as an isolated or concentrated cell population that comprises stem cells, endothelial cells and/or endothelial precursor cells.

Overview of Example Distributed Computing Environment

Figure 17:
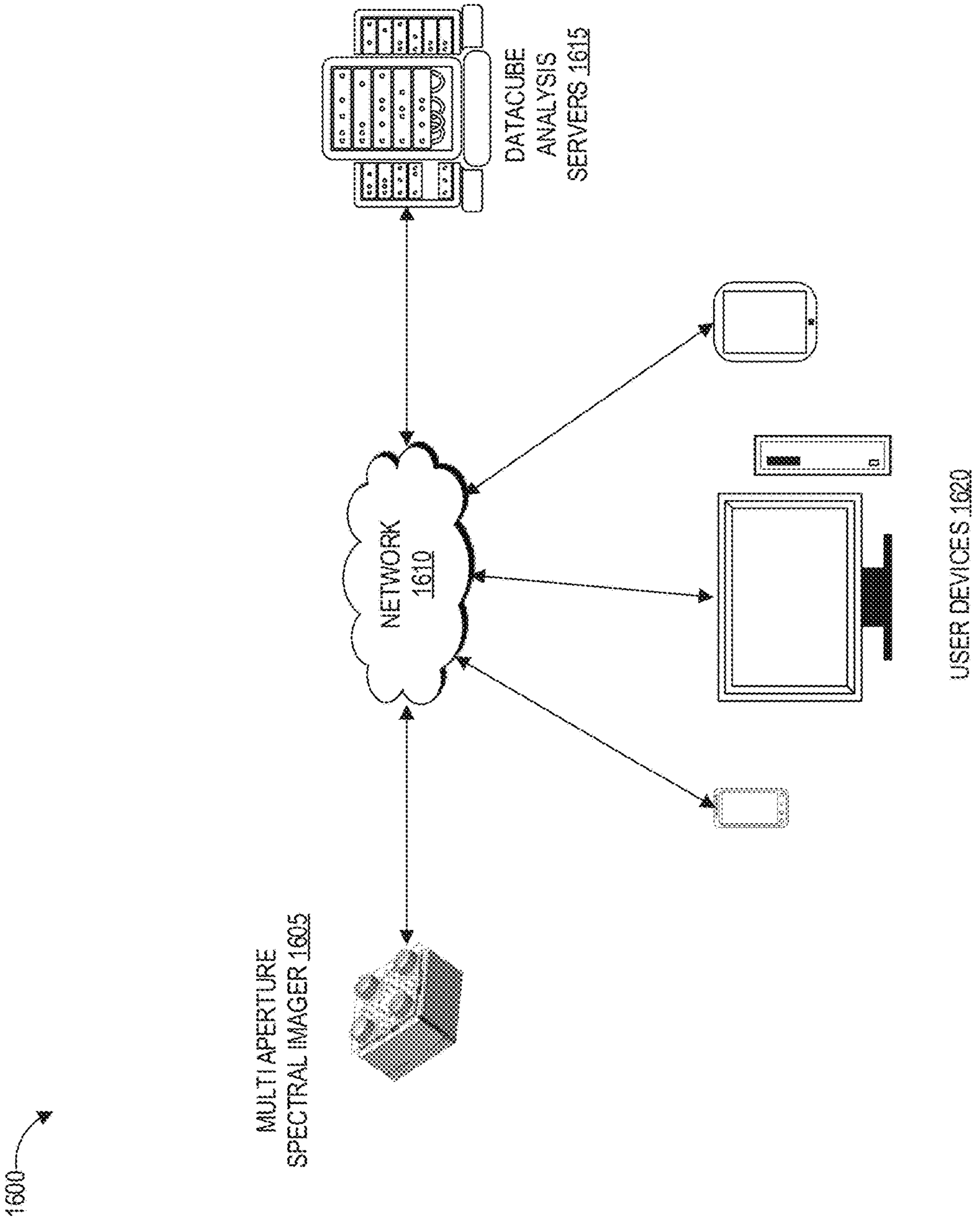
FIG. 17 depicts a schematic block diagram of an example distributed computing system including the multispectral multi-aperture imaging systems of FIGS. 3A-10B.

FIG. 17 depicts a schematic block diagram of an example distributed computing system 1600 including a multispectral multi-aperture imaging system 1605, which can be any of the multispectral multi-aperture imaging systems of FIGS. 3A-10B and 12. As depicted the datacube analysis servers 1615 may include one or more computers, perhaps arranged in a cluster of servers or as a server farm. The memory and processors that make up these computers may be located within one computer or distributed throughout many computers (including computers that are remote from one another).

The multispectral multi-aperture imaging system 1605 can include networking hardware (e.g., a wireless Internet, satellite, Bluetooth, or other transceiver) for communicating over the network 1610 with user devices 1620 and datacube analysis servers 1615. For example, in some implementations the processor of the multispectral multi-aperture imaging system 1605 may be configured to control image capture, and then send raw data to the datacube analysis servers 1615. Other implementations of the processor of the multispectral multi-aperture imaging system 1605 may be configured to control image capture and perform spectral unmixing and disparity correction to generate a multispectral datacube, which is then sent to the datacube analysis servers 1615. Some implementations can perform full processing and analysis locally on the multispectral multi-aperture imaging system 1605, and may send the multispectral datacube and resulting analysis to the datacube analysis servers 1615 for aggregate analysis and/or use in training or retraining machine learning models. As such, the datacube analysis servers 1615 may provide updated machine learning models to the multispectral multi-aperture imaging system 1605. The processing load of generating the end result of analyzing the multispectral datacube can be split between the multi-aperture imaging system 1605 and the datacube analysis servers 1615 in various ways, depending upon the processing power of the multi-aperture imaging system 1605.

The network 1610 can comprise any appropriate network, including an intranet, the Internet, a cellular network, a local area network or any other such network or combination thereof. User devices 1620 can include any network-equipped computing device, for example desktop computers, laptops, smartphones, tablets, e-readers, gaming consoles, and the like. For example, results (e.g., classified images) determined by the multi-aperture imaging system 1605 and the datacube analysis servers 1615 may be sent to designated user devices of patients, doctors, hospital information systems storing electronic patient medical records, and/or centralized health databases (e.g., of the Center for Disease Control) in tissue classification scenarios.

Example Implementation Outcomes

Background: Morbidity and mortality resulting from burns is a major problem for wounded warfighters and their care providers. The incidence of burns among combat casualties has historically been 5-20% with approximately 20% of these casualties requiring complex burn surgery at the US Army Institute of Surgical Research (ISR) burn center or equivalent. Burn surgery requires specialized training and is therefore provided by ISR staff rather than US Military Hospital staff. The limited number of burn specialists leads to high logistical complexity of providing care to burned soldiers. Therefore, a new objective method of pre-operative and intra-operative detection of burn depth could enable a broader pool of medical staff, including non-ISR personnel, to be enlisted in the care of patients with burn wounds sustained in combat. This augmented pool of care providers could then be leveraged to provide more complex burn care further forward in the role of care of warfighters with burn wounds.

In order to begin addressing this need, a novel cart-based imaging device that uses multispectral imaging (MSI) and artificial intelligence (AI) algorithms to aide in the preoperative determination of burn healing potential has been developed. This device acquires images from a wide area of tissue (e.g., 5.9×7.9 in2) in a short amount of time (e.g., within 6, 5, 4, 3, 2, or 1 second(s)) and does not require the injection of imaging contrast agents. This study based in a civilian population shows that the accuracy of this device in determining burn healing potential exceeds clinical judgement by burn experts (e.g., 70-80%).

Methods: Civilian subjects with various burn severities were imaged within 72 hours of their burn injury and then at several subsequent time points up to 7 days post-burn. True burn severity in each image was determined using either 3-week healing assessments or punch biopsies. The accuracy of the device to identify and differentiate healing and non-healing burn tissue in first, second, and third degree burn injuries was analyzed on a per image pixel basis.

Results: Data were collected from 38 civilian subjects with 58 total burns and 393 images. The AI algorithm achieved 87.5% sensitivity and 90.7% specificity in predicting non-healing burn tissue.

Conclusions: The device and its AI algorithm demonstrated accuracy in determining burn healing potential that exceeds the accuracy of clinical judgement of burn experts. Future work is focused on redesigning the device for portability and evaluating its use in an intra-operative setting. Design changes for portability include reducing the size of the device to a portable system, increasing the field of view, reducing acquisition time to a single snapshot, and evaluating the device for use in an intra-operative setting using a porcine model. These developments have been implemented in a benchtop MSI subsystem that shows equivalency in basic imaging tests.

Additional Illuminants for Image Registration

Figure 21:
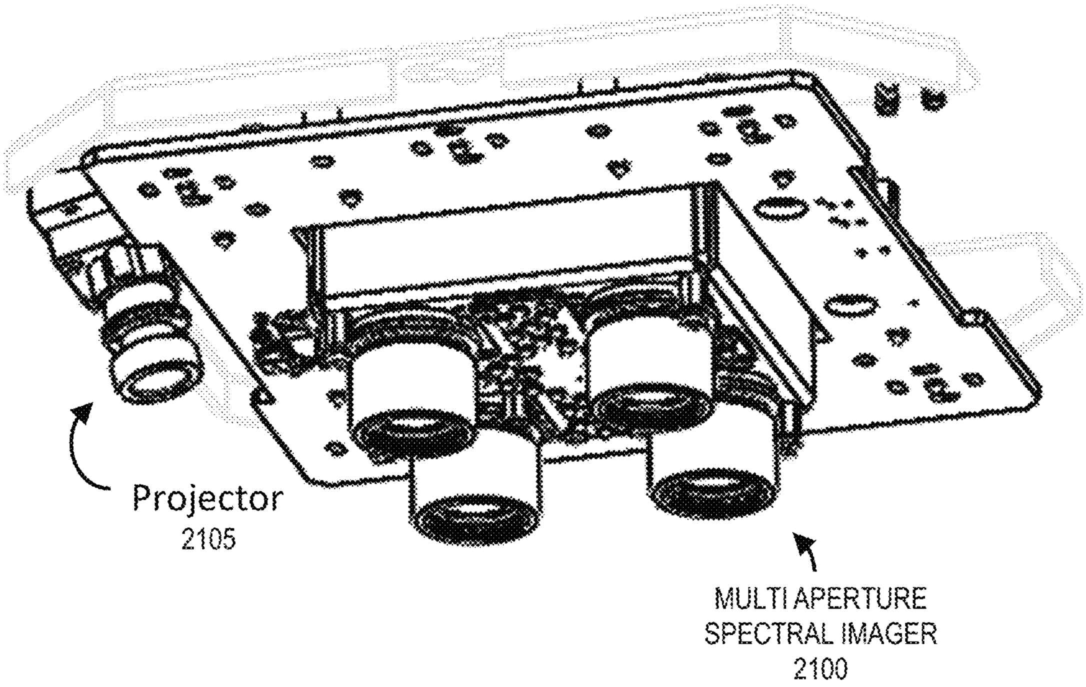
FIG. 21 illustrates an example multispectral, multi-aperture imaging system including an additional illuminant for improved image registration.

In various embodiments, one or more additional illuminants may be used in conjunction with any of the embodiments disclosed herein in order to improve the accuracy of image registration. FIG. 21 illustrates an example embodiment of a multi aperture spectral imager 2100 including a projector 2105. In some embodiments, the projector 2105 or other suitable illuminant may be, for example, one of the illuminants 1165 described with reference to FIG. 12 above. In embodiments including an additional illuminant such as a projector 2105 for registration, the method may further include an additional exposure. The additional illuminant such as the projector 2105 can project, into the field of view of the imager 2100, one or more points, fringes, grids, random speckle, or any other suitable spatial pattern in a spectral band, multiple spectral bands, or in a broad band, that are individually or cumulatively visible in all cameras of the imager 2100. For example, the projector 2105 may project light of the shared or common channel, broadband illumination, or cumulatively visible illumination that can be used to confirm the accuracy of the registration of the image calculated based on the aforementioned common band approach. As used herein, "cumulatively visible illumination" refers to a plurality of wavelengths selected such that the pattern is transduced by each of the image sensors in the multi-spectral imaging system. For example, cumulatively visible illumination may include a plurality of wavelengths such that every channel transduces at least one of the plurality of wavelengths, even if none of the plurality of wavelengths is common to all channels. In some embodiments, the type of pattern projected by the projector 2105 may be selected based on the number of apertures in which the pattern will be imaged. For example, if the pattern will be seen by only one aperture, the pattern may preferably by relatively dense (e.g., may have a relatively narrow autocorrelation such as on the order of 1-10 pixels, 20 pixels, less than 50 pixels, less than 100 pixels, etc.), while less dense or less narrowly autocorrelated patterns may be useful where the pattern will be imaged by a plurality of apertures. In some embodiments, the additional exposure that is captured with the projected spatial pattern is included in the calculation of disparity in order to improve the accuracy of the registration compared to embodiments without the exposure captured with a projected spatial pattern. In some embodiments, the additional illuminant projects, into the field of view of the imager, fringes in a spectral band, multiple spectral bands, or in a broad band, that are individually or cumulatively visible in all cameras, such as in the shared or common channel, or broadband illumination which can be used to improve the registration of images based on the phase of fringes. In some embodiments, the additional illuminant projects, into the field of view of the imager, a plurality of unique spatial arrangement of dots, grids, and/or speckle in a spectral band, multiple spectral bands, or in a broad band, that are individually or cumulatively visible in all cameras, such as in the shared or common channel, or broadband illumination which can be used to improve the registration of images. In some embodiments, the method further includes an additional sensor with a single aperture or a plurality of apertures, which can detect the shape of the object or objects in the field of view. For example, the sensor may use LIDAR, light field, or ultrasound techniques, to further improve the accuracy of registration of the images using the aforementioned common band approach. This additional sensor may be a single aperture or a multi-aperture sensor, sensitive to light-field information, or it may be sensitive to other signals, such as ultrasound or pulsed lasers.

Spectral Imaging Systems and Methods for Histological Assessment of Wounds Including Burns Introduction Microscopic analysis of tissues, or histology, is commonplace in modern medicine for the identification of tissue, the presence of disease, and the extent or severity of a disease. In many cases, histology is the gold standard of tissue analysis. However, histological analysis of tissues is not always an option in routine medical care. It is time consuming, expensive, requires specialized equipment, and the interpretation of slides requires a highly specialized pathologist. Therefore, tools that can replace this technique are desirable.

One such tool that can be used to quantify cellular features in a gross tissue area is multispectral imaging. Multispectral imaging measures light reflected from the tissue at specific wavelengths. Light interactions with tissue are dominated by absorption and scattering, which are properties of the tissue that arise from the molecular composition of the tissue and its underlying cellular structures. Through analysis of this reflected light, cellular properties can be measured, and even replace the need for pathology altogether. This is analogous to the field of remote sensing where spectral imaging is used in geologic surveys to identify the soil composition, such as the presence of certain minerals.

We demonstrate the ability for multispectral imaging to identify cellular characteristic of the tissue typically measured through histology in the setting of burn injury. In burn care, histopathology is used to determine the severity of a burn. Typically, this is not applied to every-day burn care, because collection of the tissue specimen covers a small area of the burn and is therefore not useful to make a diagnosis on a large burn area. While pathology is highly valued in determine the severity of a burn, it is not useful in a routine care setting. Therefore, the development of a device that could measure pathological features on a wide area of tissue without a requirement for collection of a tissue specimen would be valuable.

Optical coherence tomography (OCT), often described as optical pathology, could potentially solve this issue. The OCT device can acquire a detailed anatomical image of tissue structures near the surface of the tissue. OCT generates images by measuring the arrival times of light (usually infrared) that is incident on the tissue. The result is an image depicting the location of structures within the tissue. For instance, the epidermis, dermis, and structures such as sweat glands can be identified in detail. Image resolution ranges from 1 to 10 μm with an imaging depth of 1-2 mm. However, the small field of view and requirement for interpretation of the detailed image could be a challenge for application of this technique in the burn care environment.

Multispectral imaging (MSI) can assess a large area tissue in one image capture. MSI captures multiple independent measurements of reflected light from the tissue in rapid succession and is flexible to diagnosing not just the severity of the burn but identifying many other tissues, including the viable wound bed and hyperemia. Other advantages include the following: a large and scalable field of view, rapid data collection time, highly accurate determination of burn physiology, and adaptability to multiple diagnoses across the spectrum of burn care.

There are four levels of severity in burn injury: $1^{st}$ degree, superficial $2^{nd}$ degree, deep $2^{nd}$ degree, and $3^{rd}$ degree. The most important distinction is the line between superficial $2^{nd}$ degree and deep $2^{nd}$ degree, because this is the difference between a burn that will heal spontaneously through the skin's regenerative mechanisms, and a burn that will not heal and requires excision and grafting surgery.

There remains some debate as to the exact histology features of each of the four burn severities. For instance, while it is known that the skin can completely regenerates through cells in the adnexal structures, it is not completely understood at what density these viable adnexal structures should be present for regeneration to proceeded effectively. A panel of expert burn surgeons developed two decision trees for analysis of burn pathology, as illustrated in FIGS. 22A and 22B.

Figure 22A:
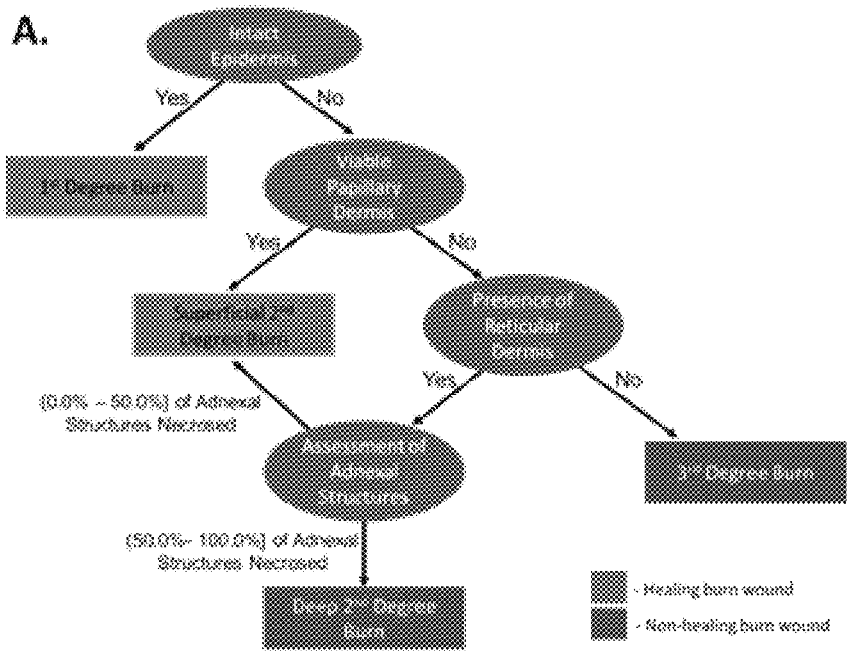
FIGS. 22A and 22B illustrate two example decision trees for analysis of burn pathology.
Figure 22B:
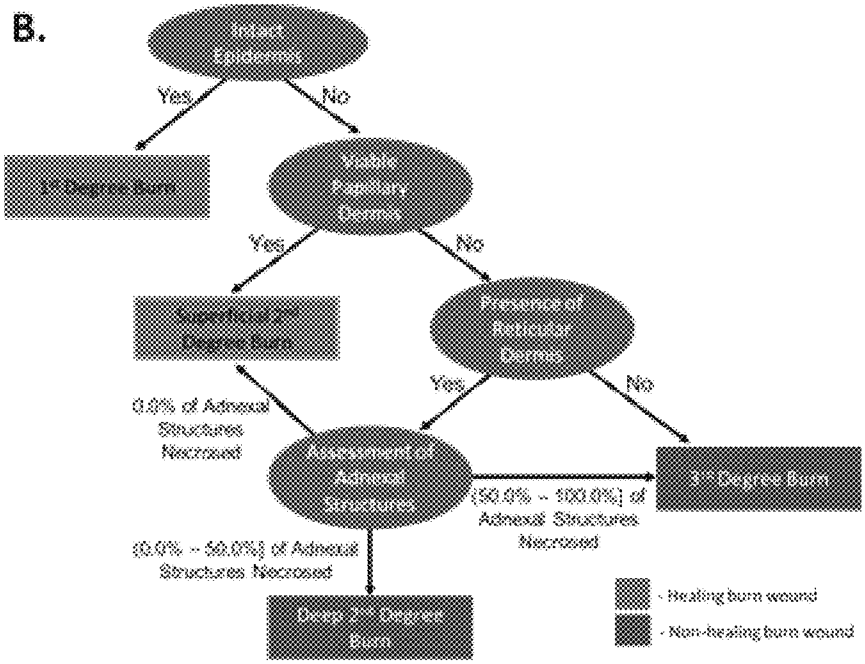

The decision trees illustrated in FIGS. 22A and 22B illustrate two methods of biopsy-guided assessment of burn severity. Adnexal structure damage is measured by counting the number of adnexal structures present in a tissue section, determining the viability of each structure individually, then computing the ratio of viable structures to total structures. In the figure, the notation (0.0%-50.0%] indicates the range from 0.0% to 50.0% excluding 0.0% and including 50.0%.

The difference in these decision trees is how the adnexal structures are involved in determining burn depth. In the first tree, tree-A, a healing burn (i.e., $1^{st}$ degree or superficial $2^{nd}$ degree) includes biopsy specimens with up to 50.0% of adnexal structures necrosed. Whereas in the second tree, tree-B, a healing burn can have no necrotic adnexal structures. Therefore, in tree-A a non-healing burn has 50.0% or more adnexal structures necrosed, and tree-B describes a non-healing burn as one with greater than 0.0% adnexal structures necrosed.

The purpose of the following analysis is to demonstrate that MSI can identify the percentage of adnexal structures damages in a burn injury. For example, the percentage of adnexal structures damages in a burn injury can be accomplished using spectral imaging with any of the spectral imaging systems and methods described within the present disclosure. To accomplish this, we simplify these decision trees to a binary decision, healing burn vs. non-healing burn. Then, we trained algorithms to determine the percent of adnexal structures necrosed using the criteria of both decision trees in FIGS. 22A nd 22B. This analysis is illustrated in FIG. 23.

Figure 23:
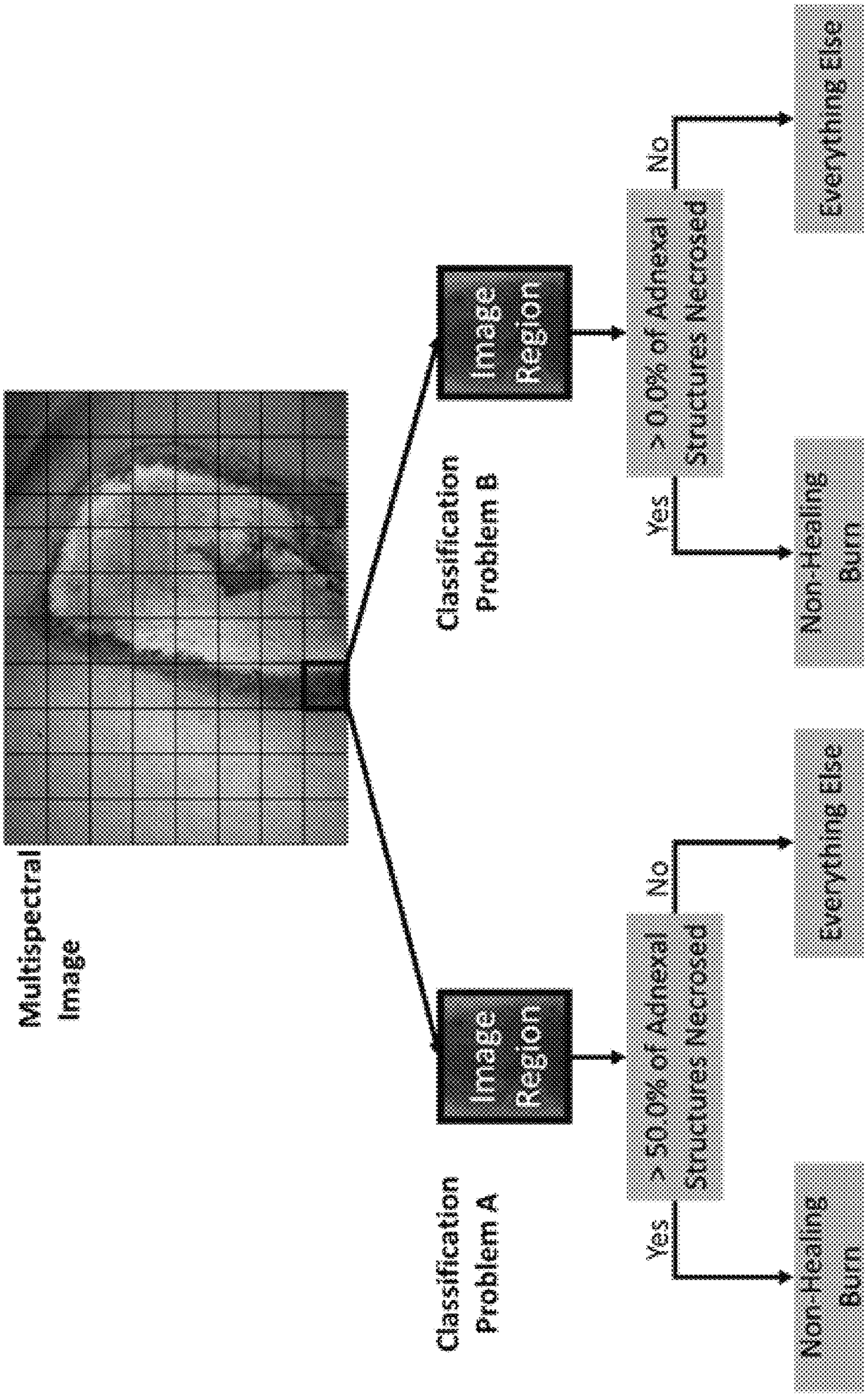
FIG. 23 illustrates two example classification problems for quantifying necrosis of adnexal structures in skin.

As illustrated in FIG. 23, two classification techniques were developed in this work to demonstrate that the data contained in the multispectral image could be used to quantify the necrosis of adnexal structures in the skin, in formation typically obtained through histology. In the classification problem, A, the MSI data would be used to identify 50.0% or more adnexal structure necrosis. In the second classification problem, B, the MSI data would be used to determine whether any (>0.0%) adnexal structures were necrosed.

While the determination of the correct decision tree is critical to the burn community, the purpose of our work was to demonstrate that MSI imaging could effectively recognize adnexal structure necrosis.

Materials and Methods

Imaging device: The multispectral imager was a multi-aperture snapshot multispectral imager. The system consisted of four color cameras positioned in each vertex of a square mounting frame with an x-shaped broad spectrum LED illumination panel mounted between the cameras, as shown in Table 1, below. The specific wavelength filters and resolution parameters of the SS imager are provided in Table 1.

Calibration of the SS imager included gain and current settings with the 95% reflectance standard. During calibration and owing to its multi-aperture design, a procedure to match corresponding points as they appear through each aperture was executed to obtain parameters for image rectification. The Calibration was performed monthly.

TABLE 1

| Specifications of the Snapshot multispectral imager. DeepView SnapShot (DV-SS) | |
|---|---|
| Operating Principle | Multi-band filters combined with color cameras followed by geometric correction and a linear transformation of raw image data into spectral channel data for each pixel. |
| Filter Bandpass: Center Wavelength (FWHM) | Channel 1: 420 ± 1% nm (20)<br>Channel.2: 525 ± 1% nm (35)<br>Channel 3: 581 ± 1% nm (20)<br>Channel 4: 620 ± 1% nm (20)<br>Channel 5: 660 ± 1% nm (20)<br>Channel 6: 726 ± 1% nm (41)<br>Channel 7: 820 ± 1% nm (20)<br>Channel 8: 855 ± 1% nm (30) |
| Image Resolution | 21 pixels per cm<br>452 pixels per $cm^2$ |
| Field-of-View (FOV) | 23 cm × 23 cm |
| Size | 14 cm × 22 cm × 22 cm** |
| Weight | 2.1 kg‡ |
| Imaging Speed | <1 second |
| Working Distance | 40 cm |

Study design: Following Internal Review Board approval, informed consent was obtained from all subjects prior to enrollment. Adult subjects greater than 18 years of age with flame, scald, or contact burns were candidates. Subjects must have been enrolled within 72 hours of their initial burn injury. Candidates were excluded from the study if their burns were isolated to regions other than the arms, legs, or torso, if they had inhalation injury, or if their burns were greater than 30% total body surface area (TBSA).

Imaging procedure: At the time of enrollment, up to three burn sites on a subject were identified for imaging. These sites were referred to as "study burns". Each study burn was imaged serially up to six separate times in the first 10 days post injury during imaging sessions. Serial imaging of each study burn was performed during routine dressing changes until the patient was discharged from the hospital or the study burn underwent surgical excision. At each imaging session, two MSI images were obtained from each study burn.

Biopsy collection and evaluation: Biopsies were only taken from areas of the study burn that were excised in the ongoing surgery. Biopsies were taken with a 4.0 mm diameter dermal punch. To guide placement of biopsies, physicians were provided a thin polycarbonate sheet pre-cut with an array of holes evenly spaced at 5.0 cm intervals.

Biopsies were immediately stored in formalin and sent for processing at a center specialized in dermatopathology. Each biopsy was fixed in paraffin, sectioned, mounted on slides, and stained with hematoxylin and eosin. Evaluation was performed by three pathologists blinded to one another and compiled according to majority-vote.

Biopsies were evaluated for burn severity using the two methods illustrated in FIGS. 22A and 22B.

In method A, biopsies of 3° burns were identified by non-viable papillary and reticular dermis. Biopsies of deep 2° burns were characterized by non-viable papillary dermis, non-viable epithelial structures of the reticular dermis, and less than 50% viability of adnexal structures of the reticular dermis. Superficial 2° burn was characterized in two ways: 1) a viable papillary dermis; or 2) a non-viable papillary dermis but viable epithelial structures, and greater than 50% viability of adnexal structures of the reticular dermis. Biopsies that contained 1° burns were identified as those with intact epidermis.

In method B, biopsies of 3° burns were identified by non-viable papillary and reticular dermis, or by having greater than or equal to 50.0% of its adnexal structures necrosed. Biopsies of deep 2° burns were characterized by non-viable papillary dermis, non-viable epithelial structures of the reticular dermis, and greater than 0.0% and less than 50% necrosis of the observed adnexal structures of the reticular dermis. Superficial 2° burn was characterized in two ways: 1) a viable papillary dermis; or 2) a non-viable papillary dermis but viable epithelial structures, and 0.0% necrosis of the observed adnexal structures of the reticular dermis. Biopsies that contained 1° burns were identified as those with intact epidermis.

Pseudocolor image generation: At many points in the study, clinicians were asked to directly label the multispectral images generated by the imaging device. To achieve this, a color photograph, termed a "pseudocolor" image, was constructed from the MSI data in one of two ways: 1) utilizing the available wavelengths closest to the red, blue, and green wavelengths of a standard digital photograph and then adjusting the intensity of each channel to be visually similar to color photography; or 2) by applying a linear transformation to the MSI, $T:\mathbb{R}^8 \rightarrow \mathbb{R}^3$, where $\mathbb{R}^3$ was a vector containing the standard RGB colors. Burn practitioners at the study site were able to adjust the brightness of pseudocolor images to improve their interpretation.

Image labeling: The true healing status of the study burn, or ground truth, used to train each algorithm was obtained using a panel of burn practitioners. This truthing panel consisted of three burn practitioners with at least one practitioner familiar with the patient and at least one independent of the study site and patient. By directly labeling each pseudocolor image, the panel generated one consensus labeled image for every study burn image that was co-located with the raw MSI data.

In one set of data, the panel of experts used the pathology features indicated in decision tree A from FIG. 22A. In the second set of data, the panel of experts used the pathology features indicated in decision tree B from FIG. 22B.

These labeled "ground truth" images indicated the location of 1°, superficial 2°, deep 2°, and 3° burn areas. These labeled images were used to generate algorithm masks that indicated the region of non-healing burn for each study burn image for later use in training, as shown in FIG. 24.

Figure 24:
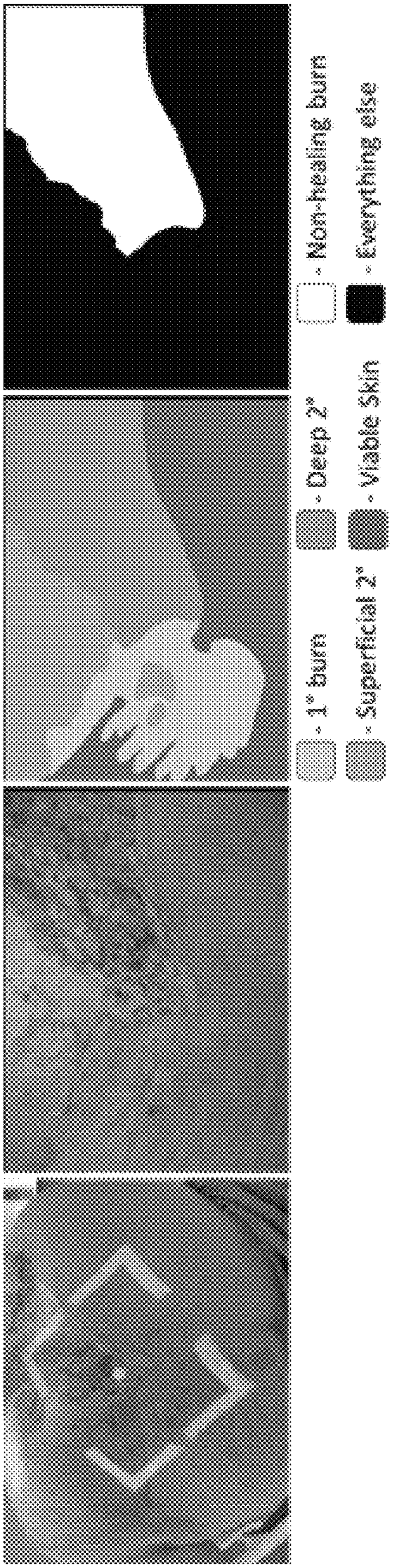
FIG. 24 illustrates the generation of imaging and ground truth masks for analysis of burn pathology.

As shown in FIG. 24, imaging and ground truth masks from a heterogeneous burn on the dorsal aspect of a subject. Green guiding beams indicate the location and distance of the MSI image; pseudocolor color image of the study burn generated from the MSI data; detailed ground truth provided by expert truthing panel; binary ground truth where all non-healing burn have been labeled as the target pixels in white.

Algorithm Development

Algorithm architectures and training: DL algorithms for image segmentation were developed to identify pixels within an image that represented non-healing burn tissue. The algorithms were trained with MSI images as the input data and labeled masks from the expert truthing panel as ground truth. These masks contained only two classes: "non-healing burn" versus "everything else" (e.g., healing burn, viable skin, and background) (FIG. 24). The masks that only contained two classes were generated from the multi-class masks provided by the truthing panel by combining deep 2° and 3° burn labels into non-healing burn and all other classes into the "everything else" category.

The algorithms were trained using stochastic gradient descent with a momentum optimizer and cross-entropy loss. The hyperparameters of learning rate, momentum, number of epochs, weight decay, and batch size were determined through experimentation with each algorithm.

Figure 25:
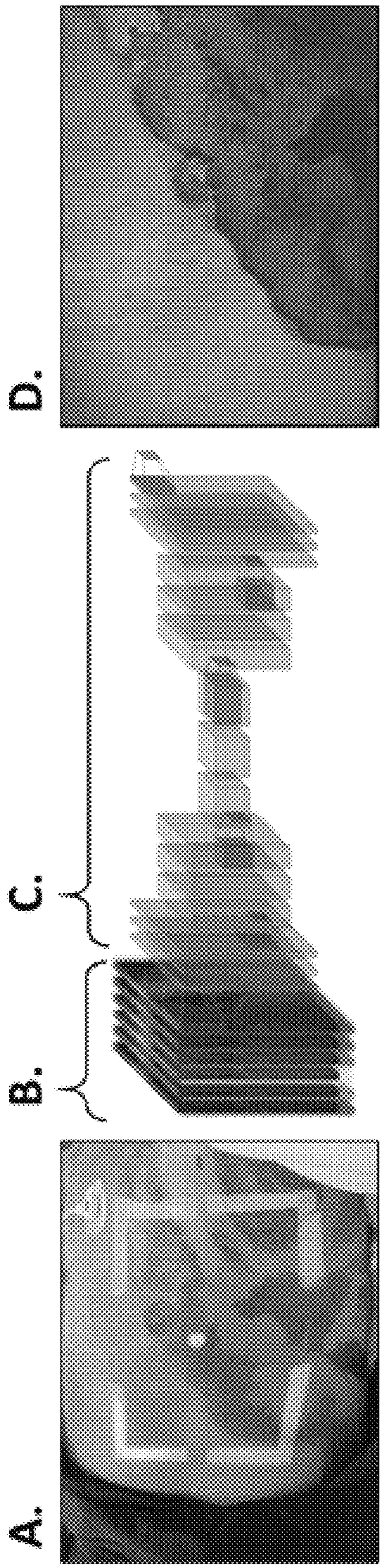
FIG. 25 illustrates an example process of generating Deep View device output in analysis of burn pathology.

FIG. 25 illustrates an example process of generating Deep View device output. A.) the green focus-and-framing beams indicate the region of tissue being imaged by the multispectral imaging sensor on the DeepView device. B.) the multispectral data acquired from the patient. This stack of images is often referred to as a datacube. C.) the DL algorithm used to process the multispectral data. D.) the output to the physician is an image of the burn with the non-healing burn area highlighted in purple.

The CNN output was a map displaying the probability of each pixel belonging to the non-healing burn class, $P(\text{pixel}_{ij}=\text{non-healing burn}|\lambda_1, \lambda_2, \ldots, \lambda_8, \Phi)$. From this probability map, a binary image was generated, where each pixel was categorized as positive or negative for non-healing burn (FIG. 25). This categorization was determined by applying a threshold, τ, to the probability of each pixel in the probability map (eq. 1). The threshold, τ, was selected by plotting the receiver operating characteristic (ROC) curve for every threshold from 0.0 to 1.0 and selecting the point on the ROC curve where the specificity was just above 0.90. This ensured that we obtained the highest sensitivity possible with a minimum specificity of 0.90.

$$1_A := \begin{cases} 1 \text{ if } P(\text{pixel}_{ij}) \geq \tau \\ 0 \text{ if otherwise} \end{cases} \quad \text{eq. 1}$$

Image Processing (IP) Algorithm Architectures: The following DL algorithms were used in this work:

SegNet: SegNet is an encoder-decoder fully convolutional neural network architecture for semantic segmentation. The novelty is that its decoder up-samples its lower resolution input feature maps and uses pooling indices computed in the max-pooling step of the corresponding encoder to perform non-linear up-sampling.

SegNet with filter-bank regularization: This algorithm is architecturally the same as the previous SegNet algorithm. The difference is that the convolutional kernels in the first layer are constrained (regularized) using a structured pre-computed filter bank. This method can influence the deep convolutional neural network kernels to learn more typical spatial structures and features. One benefit is to prevent overfitting during the training process.

SegNet with auxiliary loss: In this method, an auxiliary loss which takes image-based category information into consideration is included in the SegNet architecture so that the network can have both pixel-based and image-based features for the final prediction.

3-Dimensional SegNet: This version of SegNet is similar to the base SegNet in architecture. However, the convolutional kernels are three-dimensional instead of the standard two-dimensional kernels used in all the other CNN architectures. The 3D kernel has a 3×3×n shape where n is the number of channels in the feature map. For example, in the first layer, the kernel is 3×3×8 for the 8-channel MSI image used as input to the CNN.

SegNet (Multi-Class): In this approach, this CNN is the same as the baseline SegNet architecture except that the output layer uses cross-entropy loss with a soft-max function. This allows for the architecture to assign each pixel to one of 3 or more classes. In this architecture, we train the algorithm to learn the detailed mask images drawn by the truthing panel including 1°, superficial 2°, deep 2°, 3° burns as well as normal skin and background. These multiclass outputs are then converted to binary outputs of non-healing and not non-healing burn by simply mapping all predicted deep 2° and 3° burn pixels to non-healing burn.

SegNet Up-sampling Difficult Observations: In this final version of SegNet, we use the baseline SegNet architecture, but during training the images that are known to be difficult are used more often. This higher proportion of difficult images in training influences the algorithm to learn more from them resulting in improved performance on these difficult images.

U-Net: U-Net is an encoder-decoder DL semantic segmentation approach which works with very few training images. The U-Net algorithm uses the skip connection idea to keep the high-resolution features and make better localization.

Dilated fully connected neural network (dFCN): dFNC It is a deep fully convolutional network for semantic segmentation based on dilated convolution. In this scheme, the dilated convolutions allow the receptive field of each convolutional kernel to be increased, and at the same time not reduce the input resolution. This network can produce a pixel-level labeling without the typical encoder-decoder "hourglass" structure.

Averaging Ensemble: In this averaging ensemble, the final predicted probability of each pixel is the average probability of the corresponding pixel predicted by the eight prior DL algorithms.

Weighted Averaging Ensemble: This ensemble is a modified version of the averaging ensemble where the predicted probability of each DL model is multiplied by the weight and then their average is measured to represent the final predicted probability. The weight is the normalized sensitivity of the DL model.

Algorithm scoring: Image pixels were considered the primary unit of analysis for algorithm evaluations. Due to the limited sample size of the study, algorithm testing results were estimated using the leave-one-out cross-validation (LOOCV). For each fold of CV, the leave-out set was defined at the level of the subject to prevent exposing the algorithm to data from the subjects and burns in the left-out set.

All pixels classified by the algorithm on the left-out images were compared to the ground truth mask that indicated the true location of non-healing burn within the image, if present at all. True positives (TP) were defined as pixels in the algorithm's output image classified as non-healing burn that were also labeled as non-healing burn in the ground truth generated by the panel of experts. In the same manner we defined other pixels in the algorithm output as false positive (FP), true negative (TN), and false negative (FN) pixels. These results were summarized for every left-out set image and used to score the algorithm with five metrics, as shown in Table 2 below. The algorithm was compared to the baseline score obtained by classifying all pixels as negative (or not non-healing burn).

TABLE 2 accuracy metrics used to evaluate segmentation algorithm performance.

| Metric | Computation | |
|---|---|---|
| Rate of Accurate Classifications (i.e., Accuracy) | $\text{Accuracy} = \frac{TP+TN}{TP+FP+TN+FN}$ | eq. 2 |
| True Positive Rate (TPR; also known as Sensitivity) | $TPR = \frac{TP}{TP+FN}$ | eq. 3 |
| True Negative Rate (TNR; also known as Specificity) | $TNR = \frac{TN}{TN+FP}$ | eq. 4 |
| Area Under the Receiver Operating Characteristic Curve (AUC) | $AUC = \int_{-\infty}^{\infty} TPR(T)(-FPR(T))dT$ | eq. 5 |
| | Where TPR and FPR are probability density functions with respect to T, the classifier threshold. | |
| Sørensen-Dice (Dice) Score | $DSC = \frac{2TP}{2TP+FN+FP}$ | eq. 6 |

Results—Classification Problem A

The following section represents results obtained for image data labeled by the pathology features indicated in decision tree A from FIG. 22A.

Clinical study data: The data labeled using the methods described by the pathology features indicated in decision tree A from FIG. 22A included thirty-eight (38) subjects and a total of 58 study burns.

TABLE 3

Summary of burn depths for each image in POC study images.

| | Back-ground | Viable | 1° | Superficial 2° | Deep 2° | 3° |
|---|---|---|---|---|---|---|
| Percent of Images* | — | — | 17.8% | 75.6% | 51.7% | 16.8% |
| Percent of Pixels** | 24.6% | 31.4% | 1.9% | 21.5% | 11.9% | 8.3% |

*The summed percent of images should not add to 100%, as some images contain more than one type of burn.

**The summed percent of pixels should not add to 100%, as some classes of pixels were not reported (e.g., Silvadene cream, wound bed after excision, donor site after excision).

Out of the 58 burn wounds, 28 contain at least some area of non-healing burn based upon final ground truthing. These non-healing burn areas represent 20.2% of the total number of pixels across all study burn images, as shown in Table 3 above.

The largest subgroup of subjects was non-Hispanic white males. Burn locations were approximately evenly distributed across the arms, trunk (abdomen and chest), and legs. Additionally, many (81.6%) of the burns enrolled were caused by flame, as opposed to scalds or contact burns (5.3% and 13.2%, respectively).

The mean age of all subjects was 47.4 years (standard deviation 17.2). As per the study's exclusion criteria, subjects were required to have less than 30% TBSA, with a reported average of 14.0% (standard deviation 7.1%).

From the ground truth assessments, of each burn depth was represented in the data set, as shown in Table 3 above. The most predominant burn in the study was superficial 2° (23 burns), followed by 1° (16 burns), deep 2° (12 burns), and 3° (7 burns). It is challenging to collect 1° burn pixels, as 1° burns seldom appear in a burn center and their care will not necessarily include many follow up visits and opportunities for data acquisition.

Classifier comparison: We compared two types of classifiers: individual deep learning (DL) algorithms (Dilated FCN, SegNet and uNet), and ensembles of the DL algorithms (a voting ensemble as well as weighted ensembles). Accuracy metrics (Table 2) were obtained using cross validation and are listed in Table 4, below.

TABLE 4

Algorithm performance metrics by architecture.

| Rank | Algorithm | AUC* | Accuracy (Acc) | TPR (SE) | TNR (SP) | Training Speed† | Inferencing Speed |
|---|---|---|---|---|---|---|---|
| 1 | **TPR Ensemble | 0.955 | 0.900 (0.005) | 0.875 (0.010) | 0.907 (0.005) | 12.758 h | 1.127 s |
| 2 | **Voting Ensemble | 0.954 | 0.899 (0.005) | 0.877 (0.01) | 0.904 (0.006) | 12.758 h | 1.080 s |
| 3 | **AUC Ensemble | 0.954 | 0.899 (0.005) | 0.877 (0.01) | 0.905 (0.006) | 12.758 h | 1.127 s |
| 4 | **Accuracy Ensemble | 0.954 | 0.899 (0.005) | 0.876 (0.01) | 0.905 (0.006) | 12.758 h | 1.133 s |
| 5 | **TNR Ensemble | 0.954 | 0.899 (0.005) | 0.877 (0.01) | 0.904 (0.006) | 12.758 h | 1.132 s |
| 6 | SegNet | 0.929 | 0.885 (0.006) | 0.796 (0.015) | 0.907 (0.006) | 4.200 h | 0.354 s |
| 7 | Dilated FCN | 0.925 | 0.894 (0.005) | 0.846 (0.011) | 0.906 (0.006) | 4.647 h | 0.361 s |
| 8 | uNet | 0.911 | 0.872 (0.006) | 0.733 (0.017) | 0.908 (0.005) | 3.911 h | 0.390 s |
| | BASELINE (all negative) | 0.500 | 0.798 | 0.000 | 1.000 | — | — |

*AUC was used to rank algorithm performance.

**Trained with Dilated FCN, SegNet, and uNet.

†Training speed calculated per fold, or per all images associated with a single study burn.

All algorithm accuracy metrics should be compared to the baseline, determined by classifying all pixels as negative (or no non-healing burn). In the baseline, all the pixels representing the background, viable skin, and healing burns (i.e., 1° and superficial 2°) will be correctly classified, and all pixels representing non-healing burns (deep 2°, and 3°) will be incorrect. Given the current data, the baseline accuracy metrics are AUC 0.5, accuracy 79.8%, TPR 0%, and TNR 100%.

The deep learning algorithms represent a dramatic improvement over the baseline. However, the top-performing group of algorithms is the ensemble models. The TPR-ensemble had AUC of 0.955 and accuracy rate of 90.0% (95% confidence interval [CI]: 89.0 to 91.0%); whereas SegNet, the best deep learning algorithm, had AUC of 0.929 and an accuracy rate of 88.5% (95% CI: 87.3% to 89.7%). The gains are especially evident in terms of TPR, with 87.5% for the ensemble compared to 79.6% for SegNet.

The TPR-ensemble model of the Dilated Fully Convolutional Network, SegNet, and uNet architectures, all trained with MSI data, outperformed all other algorithms with an AUC of 0.955 and accuracy rate of 90.0% (95% CI: 89.0 to 91.0%). All of the other weighted ensemble algorithms had similar performance, and all other ensemble algorithms outperformed both the individual deep learning components (especially in terms of the TPR, indicative of the ensemble algorithms' ability to correctly identify non-healing burn tissue).

A one-way ANOVA was conducted with algorithm group (deep learning algorithms and ensemble models) as a two-level factor, and responses blocked by burn. The ANOVA includes three (3) deep learning algorithms (Dilated FCN, SegNet, and uNet), and five ensemble models (voting ensemble; ensembles weighted by accuracy, AUC, TNR, and TPR), as shown in Table 5, below.

TABLE 5

ANOVA for Algorithm Accuracy Results.

| ANOVA | Degrees of Freedom | Sum of Squares | Mean Squares | F-statistic | p-Value |
|---|---|---|---|---|---|
| Block (Burn) | 57 | 30.42 | 0.534 | 89.92 | <2e−16 |
| Algorithm | 1 | 0.17 | 0.172 | 28.98 | 2.85e−08 |
| Residuals | 3085 | 18.31 | 0.006 | | |

TABLE 6

Tukey's Honest Significant Difference Test for Pairwise Comparisons of Algorithm Group Accuracy Rates.

| Comparison | Estimate | 95% CI | Adjusted p-value* |
|---|---|---|---|
| Ensembles - Deep Learning | 1.53% | (0.97%, 2.08%) | 1e−07 |

*p-value adjusted for multiple comparisons

From Table 5, at least one burn had a significantly different accuracy rate than the others (p-value<2e-16) and at least one algorithm group had a significantly different mean accuracy than the others (p-value=2.85e-08).

From Tukey's Honest Significant Difference Test (Table 6), the p-values indicate that the ensemble models had significantly higher mean accuracy than the deep learning algorithms. On average, they were 1.53% more accurate than the deep learning classifiers.

Figure 26:
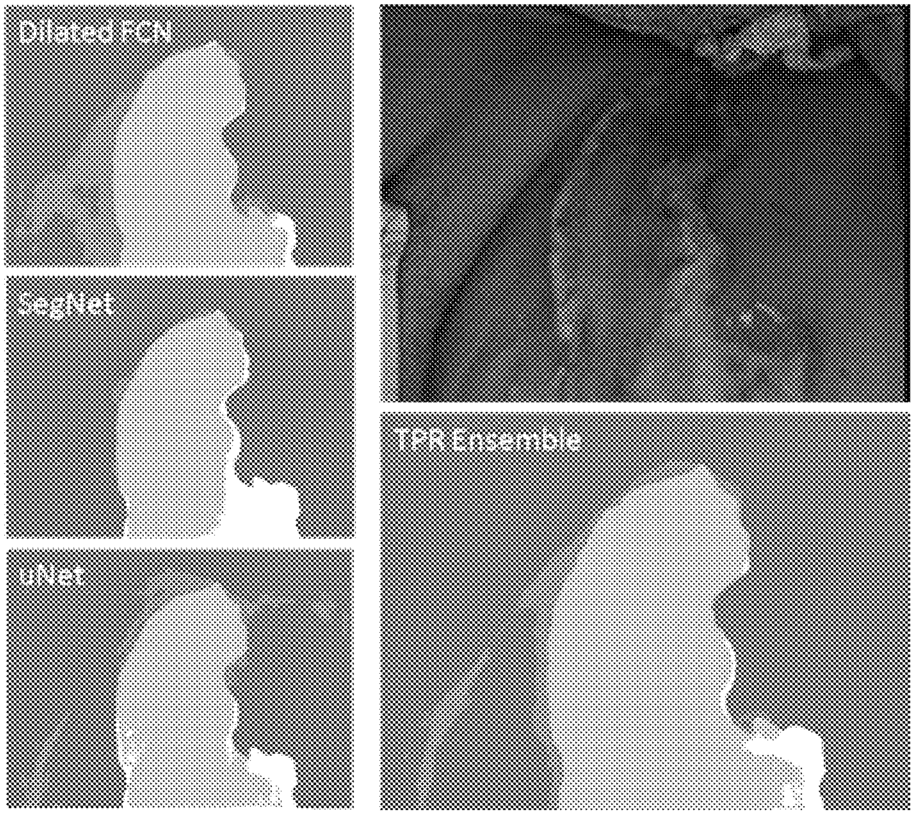
FIG. 26 illustrates sample outputs for burn histology from several machine learning algorithms.

A visual example of the individual algorithms and the resulting ensemble is shown in FIG. 26. Demonstrative of the high TPR and TNR of the ensemble prediction, the highlights indicating non-healing burn cover nearly all of the white area, which represents true non-healing pixels, and only a very small gray area, which represents all other classes. Each algorithm in the ensemble makes different kinds of predictions and errors and combining them in the ensemble results in an accurate prediction and avoids errors inherent to a single algorithm.

FIG. 26 shows sample outputs from different machine learning algorithms. (Left) Algorithm predictions overlaid on ground truth masks for individual deep learning algorithms. Gray areas represent areas of background, viable skin, and healing burn, as per the ground truth. White areas represent areas of non-healing burn as per the ground truth. Blue areas represent areas of non-healing burn as predicted by the algorithm. (Top Right) Color image of a POC study burn (Subject 006, 56 year-old-female). (Bottom Right) TPR-ensemble output.

Accuracy within burn severities: The TPR-ensemble algorithm demonstrated AUC equal to 0.955. The Receiver Operating Characteristic (ROC) curve is shown in Table 7, below.

TABLE 7

Accuracy by Tissue Type.

| | Severity | | | |
|---|---|---|---|---|
| | 1° | Superficial 2° | Deep 2° | 3° |
| Accuracy | 0.974 | 0.809 | 0.839 | 0.930 |

Accuracies by burn class (1°, superficial 2°, deep 2°, and 3° burn injuries) appear in Table 7, above. The relationship between overall accuracy of the TPR-ensemble (90%) and accuracy for individual tissue types is a weighted average of the accuracy for each class where the weights are the proportion of pixels belonging to that class. Note this weighted average includes all classes of tissue defined in this study such as: background; viable skin; and all burn severities.

Results—Classification Problem B

The following section represents results obtained for image data labeled by the pathology features indicated in decision tree B from FIG. 22B.

Clinical study data: A total of 25 subjects, 20 males and 5 females, were enrolled with a mean age of 45.72 (±17.77 SD). The average total body surface area of burns was 14.24 (±12.22 SD). Race was described as 11 Black and 14 White, with one subject of Hispanic ethnicity. Skin tone was self-reported using the Fitzpatrick scale, an index with six categories of increasing melanin content. The Fitzpatrick scores indicated: 12 subjects identified as category II; 4 subjects as categories III and IV; nine subjects as categories V and VI; and 0 subjects identified as category I. Two subjects reported type II diabetes and 14 were current smokers.

From these 25 subjects, 56 study burns were imaged with both the DV-FW and DV-SS devices. Forty-eight (48) burns were from flame, the remaining burns were evenly split into contact and scald. A majority of study burns selected for imaging occurred on the anterior surface of the body (73%). Twenty-two (22) burns were imaged on the leg and thigh, 18 on the arm and forearm, and 16 on the trunk.

Of these 56 Study Burns, 44 underwent surgical excision. The follow-up protocol for these 44 burns was to obtain a series of punch biopsies from the excised area in the OR immediately prior to excision. This was conducted for all 44 burns. The remaining 12 study burn areas were treated with conservative wound care and their follow-up was a 21-day healing assessment.

Classifier comparison: We compared two types of classifiers: individual deep learning (DL) algorithms (Dilated FCN, SegNet, SegNet with Auxiliary Loss, SegNet with Filter-Bank Regularization, and uNet), and ensembles of the DL algorithms (a voting ensemble as well as weighted ensembles). Accuracy metrics, as shown in Table 2 above, were obtained using cross validation and are listed for this example in Table 8 below. These accuracy metrics are further illustrated in FIGS. 27A and 27B.

Figure 27A:
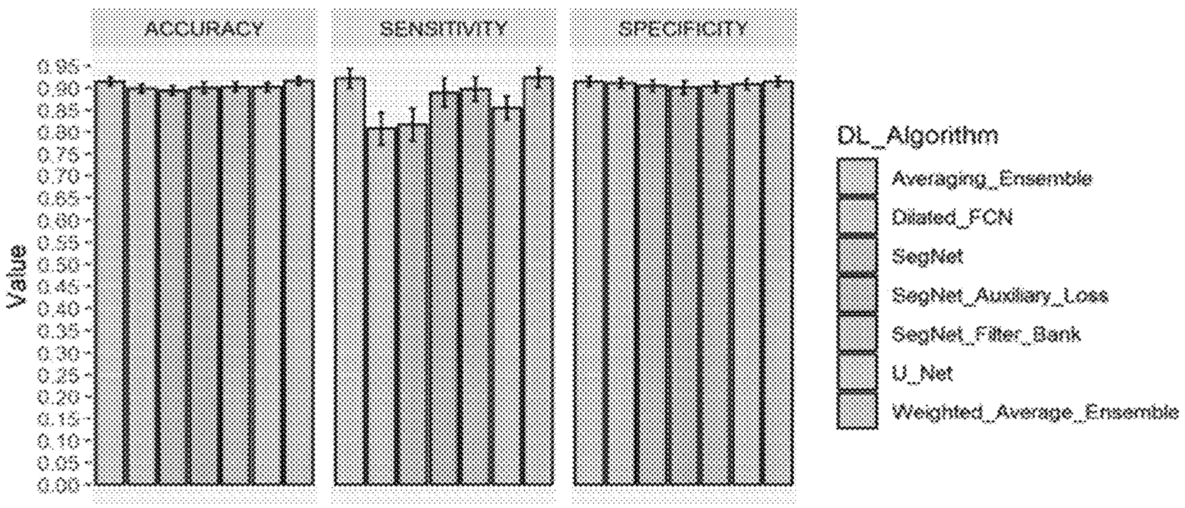
FIGS. 27A and 27B illustrate example accuracy metrics associated with histological analysis using the spectral imaging systems and methods described herein.
Figure 27B:
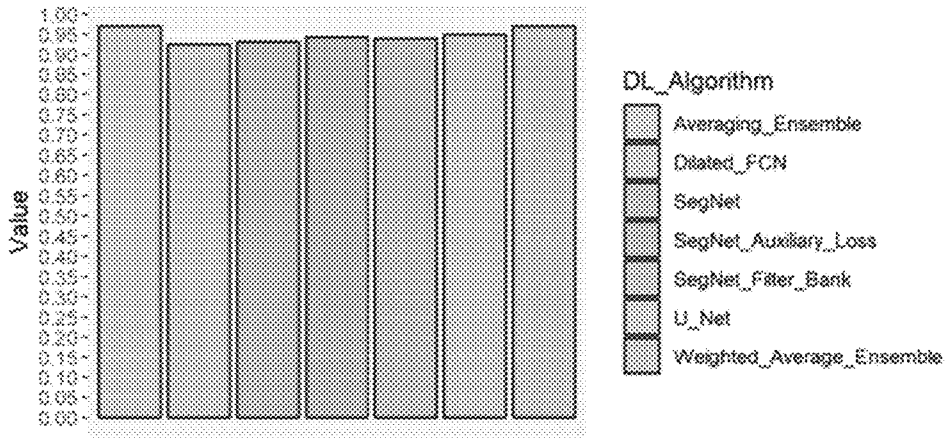

FIG. 27A is a bar diagram of accuracy metrics for algorithms generated to solve Classification Problem B. FIG. 27B is a bar diagram of AUCs for algorithms generated to solve Classification Problem B.

TABLE 8

Accuracy metrics for algorithms generated to solve Classification Problem B.

| Deep Learning Algorithm | Metric | Value | ±95% CI |
|---|---|---|---|
| Dilated_FCN | Accuracy | 0.899179 | 0.009564422 |
| Dilated_FCN | Sensitivity | 0.807572 | 0.037014739 |
| Dilated_FCN | Specificity | 0.911566 | 0.010654487 |
| Dilated_FCN | AUC | 0.924268 | |
| SegNet | Accuracy | 0.894727 | 0.010581947 |
| SegNet | Sensitivity | 0.816425 | 0.037905555 |
| SegNet | Specificity | 0.905315 | 0.011810311 |
| SegNet | AUC | 0.931457 | |
| SegNet_Auxiliary_Loss | Accuracy | 0.900237 | 0.012576146 |
| SegNet_Auxiliary_Loss | Sensitivity | 0.889892 | 0.032222824 |
| SegNet_Auxiliary_Loss | Specificity | 0.901636 | 0.014732132 |
| SegNet_Auxiliary_Loss | AUC | 0.942048 | |
| SegNet_Filter_Bank | Accuracy | 0.902809 | 0.010203503 |
| SegNet_Filter_Bank | Sensitivity | 0.897311 | 0.025789759 |
| SegNet_Filter_Bank | Specificity | 0.903552 | 0.011343372 |
| SegNet_Filter_Bank | AUC | 0.939487 | |
| U_Net | Accuracy | 0.902794 | 0.010283708 |
| U_Net | Sensitivity | 0.85559 | 0.02664729 |
| U_Net | Specificity | 0.909177 | 0.011634774 |
| U_Net | AUC | 0.948823 | |
| Averaging_Ensemble | Accuracy | 0.915555 | 0.009728824 |
| Averaging_Ensemble | Sensitivity | 0.922901 | 0.022060835 |
| Averaging_Ensemble | Specificity | 0.914561 | 0.01115219 |
| Averaging_Ensemble | AUC | 0.970496 | |
| Weighted_Average_Ensemble | Accuracy | 0.915854 | 0.009717206 |
| Weighted_Average_Ensemble | Sensitivity | 0.923229 | 0.021923662 |
| Weighted_Average_Ensemble | Specificity | 0.914857 | 0.011135854 |
| Weighted_Average_Ensemble | AUC | 0.97057 | |

Example Burn Depth Analysis Using Spectral Imaging

Introduction

Burn care is a highly specialized area of medicine challenged by wounds of diverse severity and patients with equally diverse confounding illness or injuries impacting healing. Even burn experts are only 77% accurate in their burn depth assessment (BDA) leaving almost a quarter of patients to undergo unnecessary surgery or conversely suffer a delay in treatment. To aid clinicians in BDA, new technologies are being studied with machine learning algorithms calibrated to histologic standards. Unfortunately, histologic assessment is rarely done in burn care and can be discordant with visual assessment. Our goal was to review and assess the largest burn wound biopsy library and submit a burn biopsy algorithm (BBA) for categorizing BDA based-upon histologic analysis as a work-in-progress.

Methods

The study was an IRB-approved, prospective, multicenter design with multiple wounds per patient. Patients with burn wounds assessed by the burn expert as unlikely to heal and require excision and autograft were enrolled with 4 mm biopsies procured every 25 $cm^2$. Burn biopsies were obtained immediately prior to excision and assessed histologically following hematoxylin and eosin staining by a board-certified dermatopathologist, for presence or absence of epidermis, papillary dermis, and adnexal necrosis. The BBA was used to categorize histological findings into $1^{st}$ degree (°), superficial 2°, deep 2°, or 3° burn. These categorizations were compared to visual assessment of the burn by three expert burn surgeons, algorithm was a decision tree that consisted of the following: biopsies of 3° burns were identified by non-viable papillary and reticular dermis, or by having greater than or equal to 50.0% of its adnexal structures necrosed. Biopsies of deep 2° burns were characterized by non-viable papillary dermis, non-viable epithelial structures of the reticular dermis, and greater than 0.0% and less than 50% necrosis of the observed adnexal structures of the reticular dermis. Superficial 2° burn was characterized in two ways: 1) a viable papillary dermis; or 2) a non-viable papillary dermis but viable epithelial structures, and 0.0% necrosis of the observed adnexal structures of the reticular dermis. Biopsies that contained 1° burns were identified as those with intact epidermis.

Results

At the time of submission, 65 patients were enrolled with 117 wounds and 487 biopsies. The burn biopsy algorithm was used to categorize 100% of the burn regions into four different categories. Still photos were obtained at the time of enrollment and before excision intraoperatively. The first two were likely to heal and not require excision and labeled $1^{st}$ degree or Superficial $2^{nd}$ degree. The last two were assessed unlikely to heal within 21 days and labeled deep $2^{nd}$ degree or $3^{rd}$ degree burn wounds.

Conclusions

Our study demonstrates that a BBA with objective histologic criteria can be used to categorize BDA. Clinical intrigue regarding regenerative capacity remains an intrinsic component of this research that will hopefully be answered with additional data analysis as a component of the on-going study. This study serves as the largest analysis of burn biopsies by modern day burn experts and as a the first to define histologic parameters for BDA.

Example Algorithm Training for Histological Assessment of Wounds Including Burns Introduction Clinical evaluation of the burn wound: Clinical evaluation of the burn wound is the most widely used and the least expensive method of assessing burn wound depth. This method relies on a subjective evaluation of the external features of the wound such as wound appearance, capillary refill, and burn wound sensibility to touch [1-4]. These burn wound characteristics can be readily observed and therefore clinical assessment of the burn wound can be made immediately, easily, and with minimal costs involved. Unfortunately, the clinical features used to assess burn depth have been shown to be accurate in only approximately 70% of the cases, even when carried out by an experienced burn surgeon.

Histological assessment of burn depth: Punch biopsy of burn tissue with subsequent histological analysis is frequently considered as the 'gold standard' of burn depth assessment, serving as the basis for comparison of other diagnostic modalities. Burn depth is described in terms of the anatomical depth at which the boundary between healthy and necrotic tissue is observed. Assessment is performed by a board-certified pathologist on thin sections (paraffin-embedded) of the tissue following hematoxylin and eosin (H&E) staining. Using this simple technique, the pathologist can determine changes to cellular viability, collagen denaturation and evaluation of adnexal structures damage and assessment of patent blood vessel caused by the burn injury.

The depth of the wound dictates the healing mechanism: The amount of time needed for re-epithelialization to complete depends on many factors, including specifics of the wound (e.g. location, depth, size, presence of infection) and age of the patient.

Skin wounds can be of variable depth and thus can affect one or more skin layers. To describe the nature of a lesion, wounds are typically classified as partial- or full-thickness wounds. Partial-thickness wounds involve the epidermis and may involve a portion of the dermis. These wounds can be further classified in "superficial" and "deep" partial-thickness wounds, depending on the amount of dermis affected. Typically, epithelial-derived adnexal structures such as hair follicles, sebaceous glands, apocrine glands, and/or eccrine sweat glands remain partially intact in a partial-thickness wound. Whether superficial or deep, a partial-thickness wound heals primarily by re-epithelialization. Repair of the epidermal layer is achieved through regeneration of the epidermal cells both from the perimeter of the wound and from the adnexal structures of the epidermis (e.g., hair follicles, sweat glands, and sebaceous glands). Therefore, presence of viable adnexal structures is critical to ensure wound repair in 21 days. In contrast, full-thickness wounds destroy the entire dermis, and possibly more. They do not heal by re-epithelialization alone but require formation of a so-called granulation tissue to fill the void of the wound before epithelial covering.

Figure 28:
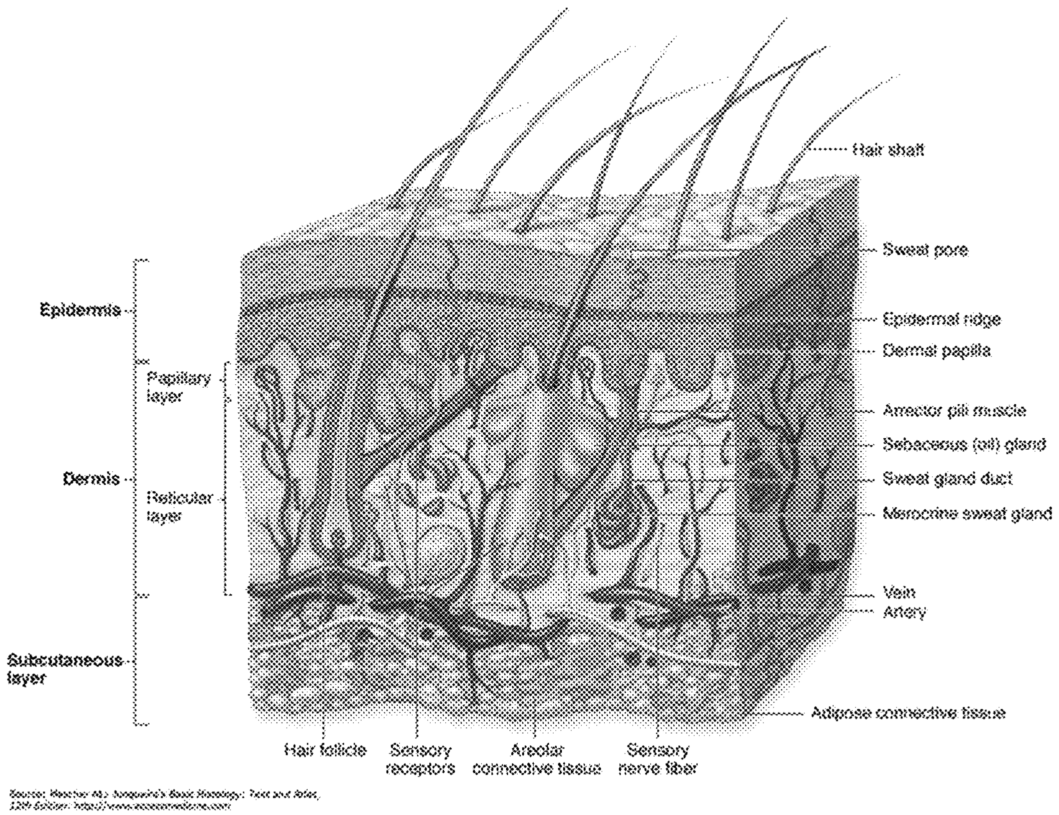
FIG. 28 illustrates example anatomical structures of the skin.

FIG. 28 illustrates skin anatomy including papillary dermis, reticular dermis, epithelial structures, and adnexal structures. Example adnexal structures include arrector pili muscles, sebaceous glands, sweat glands, cutaneous sensory receptors, and hair follicles. Example epithelial structures include arteries, veins, and capillaries.

The dermis itself is divided into two regions, the uppermost being the papillary dermis. It is composed mostly of connective tissue and serves only to strengthen the connection between the epidermis and the dermis. When thermal injury only extends into the papillary region of the skin, the injured skin can regenerate and therefore the burn is considered superficial.

Just below this region is the reticular dermis. It contains connective tissue as well as epithelial and adnexal structures such as hair follicles, sebaceous and sweat glands, cutaneous sensory receptors, and blood vessels. When thermal injury occurs in this region it is of critical importance to identify the viability of these structures, because viable adnexal structures ensure wound repair within 21 days. Therefore, damaged reticular dermis with viable adnexal structures is considered a superficial second degree burn. Damage that is deeper than the reticular dermis indicates a full-thickness, third degree burn.

H&E staining: Damage to the reticular and/or papillary dermis can be readily determined using H&E staining. Damage to the dermis can be identified by hyalinized collagen (magenta discoloration) and a lack of detectable individual collagen fibers. Within a high power microscopic field, the pathologist can easily discern normal and damaged collagen. Adnexal structure damage is readily detectable as follicular epithelia exhibit features consistent with cell injury (e.g., cell swelling, cytoplasmic vacuolization, nuclear pyknosis, etc.).

Histopathology Methods

Specimen Handling: The burn site where biopsies (4-6 mm diameter) were collected was photographed with a point-and-shoot digital camera before and after punch biopsies in order to clearly mark the biopsy locations in the burn wound. The specimens were immediately labeled and preserved in formalin, per the POC clinical protocol, and sent to Cockerell Dermatopathology Laboratories in Dallas, TX.

Pathology Reading: At Cockerell Dermatopathology, the specimens were processed and reviewed by three board certified pathologists who were blinded to the subject and burn information. Independently, each pathologist identified the depth of injury in the specimen based on specific pathological features of the burn. Following independent analysis, the pathologists combined their findings into a single conclusion of the pathological findings of each specimen. Their findings were documented in a pathology report.

Figure 29:
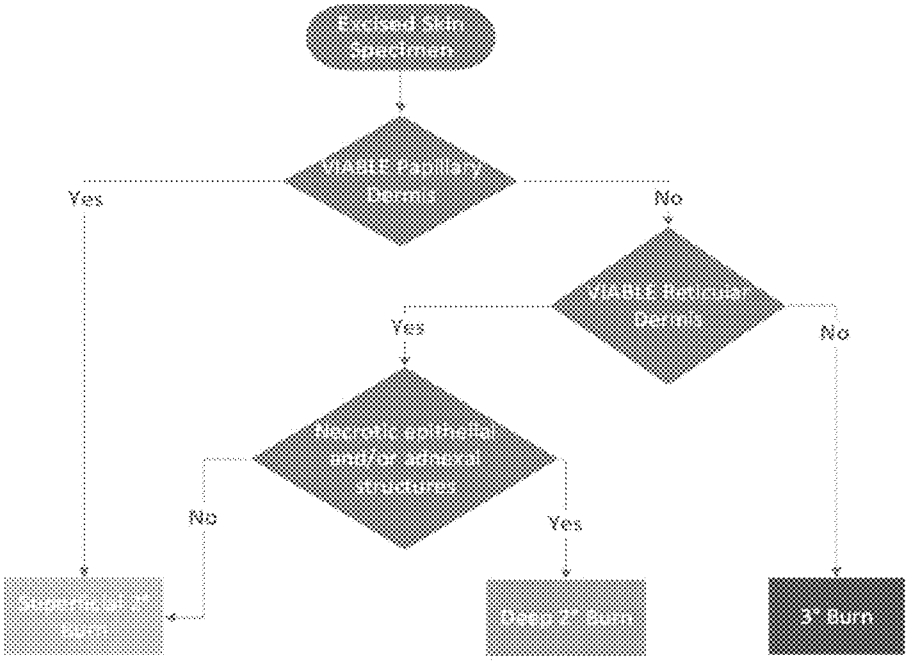
FIG. 29 illustrates a logical flow used to assess thermal injury and burn severity.

Histological assessment of burn depth required the pathologist to review specific structures of the skin specimen for thermal injury. FIG. 29 illustrates a logical flow used to describe these structures and their importance in determining burn severity. Briefly, the papillary dermis was reviewed for damage, and if no damage was found, the burn was considered superficial second-degree. If damage to the papillary dermis had occurred, the pathologist looked deeper to assess the reticular dermis. If no damage to the reticular dermis was found, the burn could still be considered superficial second-degree. If complete, full-thickness damage to the reticular dermis had occurred the burn was third-degree. However, if there was partial damage to the reticular dermis, the pathologist was required to review individual epithelial and adnexal structures within the reticular dermis. If epithelial or adnexal structures, which reside in the half of the overall dermis, demonstrated necrosis the burn was considered deep second-degree. If there was no necrosis to these structures then a burn remained superficial second-degree.

Figure 30A:
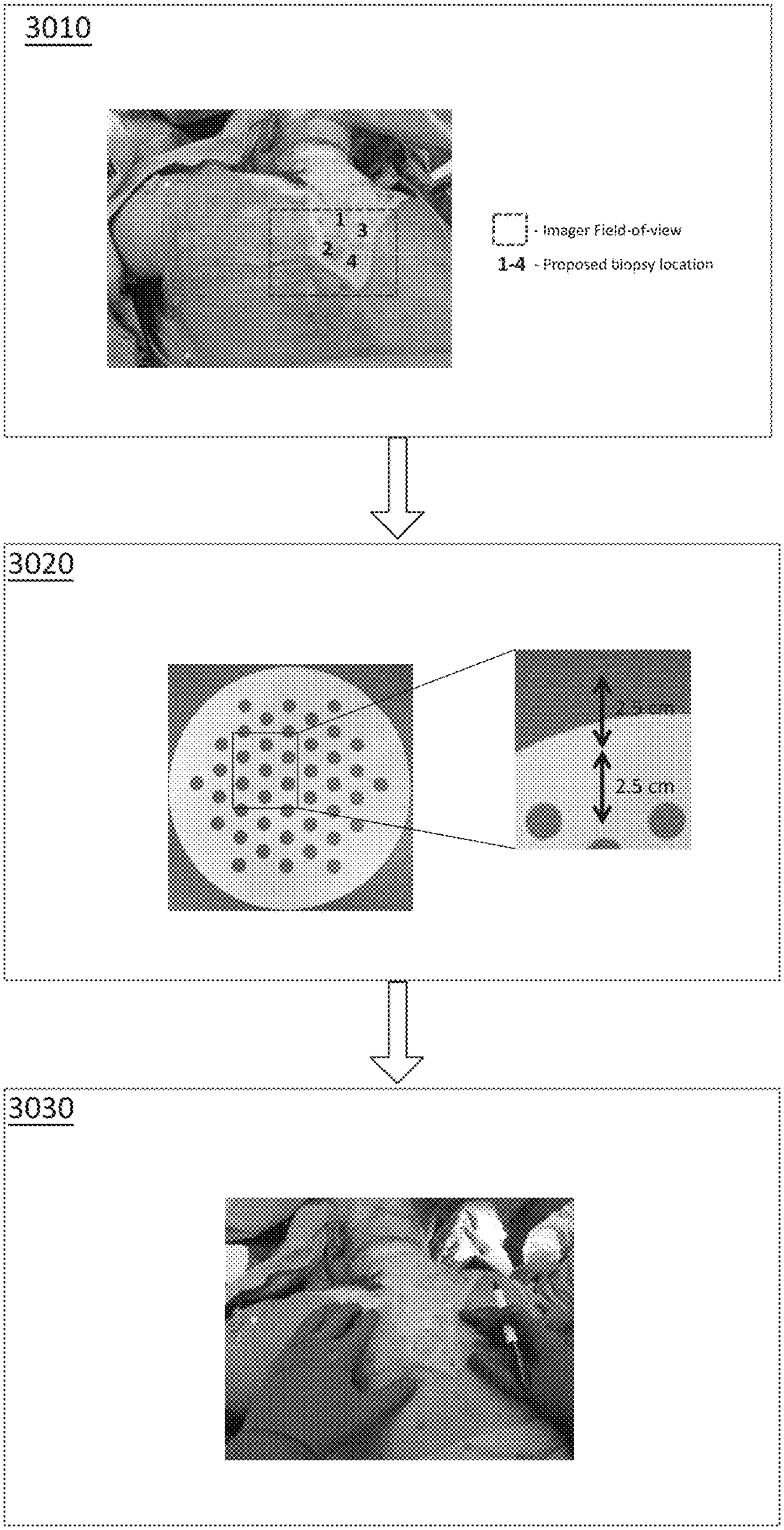
FIGS. 30A-30C illustrate an example method of developing and training an algorithm for histological assessment of wounds based on spectral imaging.
Figure 30B:
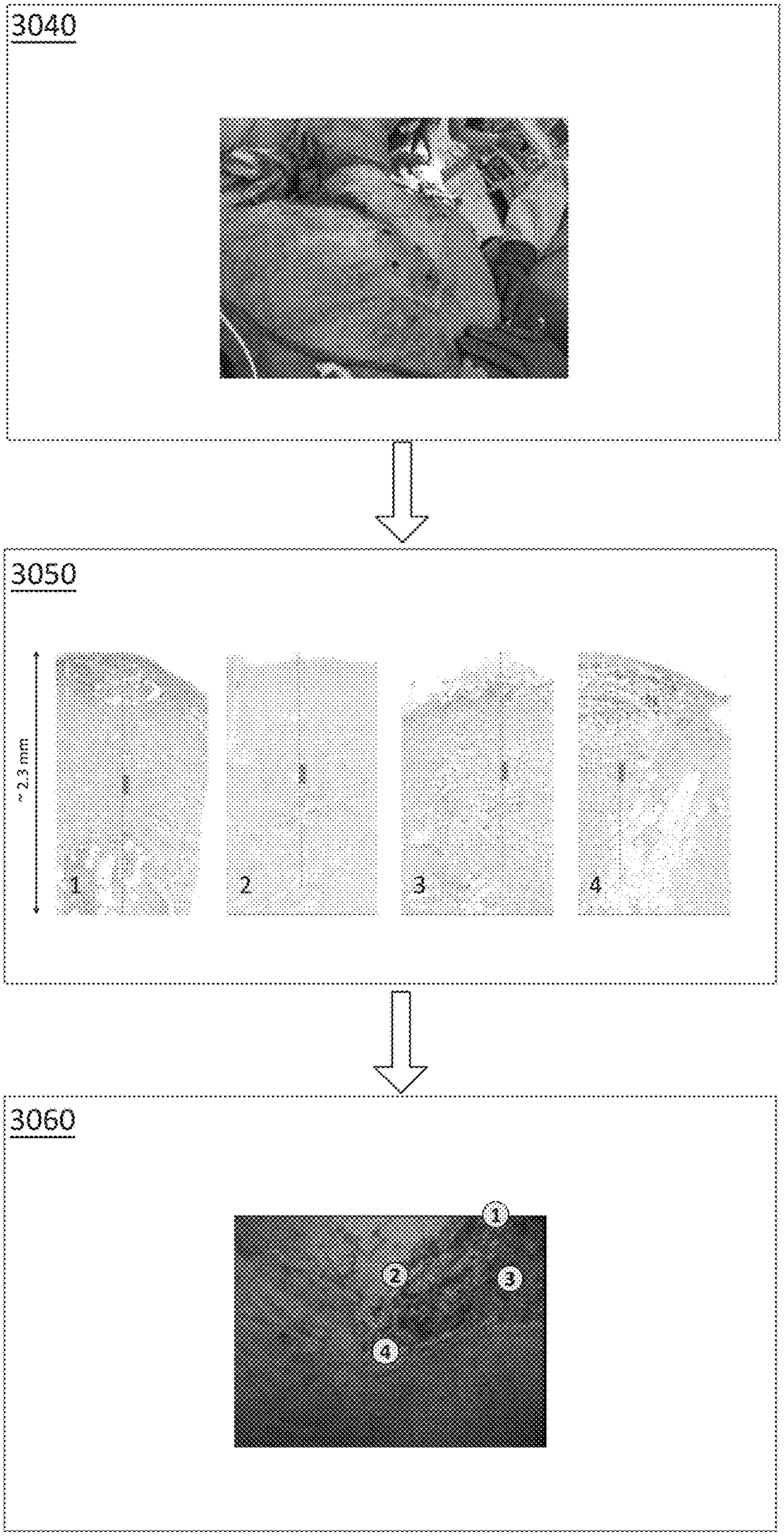
Figure 30C:
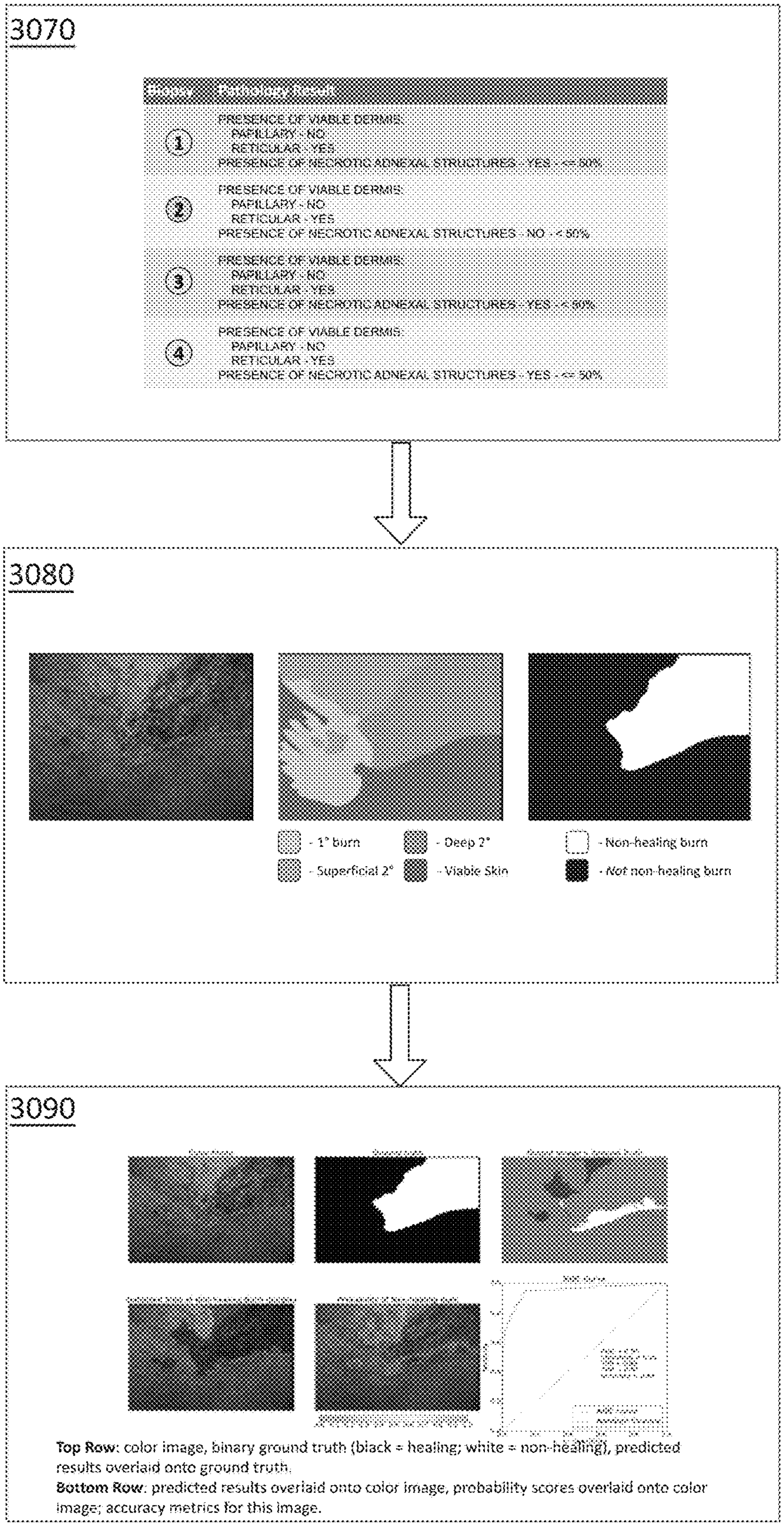

FIGS. 30A-30C illustrate an example method of developing an algorithm for histological assessment of wounds based on spectral imaging. At step 3010, prior to excision, practioners determine biopsy locations within an imager field-of-view. Each region to be excised within the study burn site may be identified.

At step 3020, a biopsy guide tool can be designed and provided. In the example of FIGS. 30A-30C, the biopsy guide tool can be a serializable, thin, and flexible plastic guide tool having apertures spaced to ensure selected biopsy locations occur within 5.0 cm from one another.

At step 3030, the biopsy locations are labeled using the guide tool and a surgical pen.

At step 3040, biopsies (e.g., 4.0 mm punch biopsies) are collected at the labeled biopsy locations. The collected biopsies may be stored, e.g., in formalin or the like.

At step 3050, each collected biopsy can be independently reviewed. The biopsies may be reviewed by, for example, two or three or more pathologists blinded to subject and burn information. The biopsies may be H&E stained and evaluated using a standard set of criteria as discussed above.

At step 3060, the biopsy locations may be overlaid onto an image of the biopsy site generated using the spectral imaging device.

At step 3070, an expert truthing panel may review the independent results of the pathologists' review and determine a pathology result for each biopsy.

At step 3080, one or more ground truth masks may be determined corresponding to criteria such as, for example, a burn depth status, or a healing status such as non-healing or not non-healing. Step 3080 illustrates two such example ground truth masks. The image in the center is a detailed ground truth mask indicating burn depth status of regions of the original color image of the burn shown at left. The image at right is a binary ground truth mask indicating healing status of regions of the original color image of the burn shown at left.

At step 3090, one or more machine learning algorithms are trained and tested based on the developed ground truth mask or masks.

Terminology

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips or magnetic disks, into a different state. In some embodiments, the computer system may be a cloud-based computing system whose processing resources are shared by multiple distinct business entities or other users.

The disclosed processes may begin in response to an event, such as on a predetermined or dynamically determined schedule, on demand when initiated by a user or system administer, or in response to some other event. When the process is initiated, a set of executable program instructions stored on one or more non-transitory computer-readable media (e.g., hard drive, flash memory, removable media, etc.) may be loaded into memory (e.g., RAM) of a server or other computing device. The executable instructions may then be executed by a hardware-based computer processor of the computing device. In some embodiments, the process or portions thereof may be implemented on multiple computing devices and/or multiple processors, serially or in parallel.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on computer hardware, or combinations of both. Moreover, the various illustrative logical blocks and modules described in connection with the embodiments disclosed herein can be implemented or performed by a machine, such as a processor device, a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein.

A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements or steps. Thus, such conditional language is not generally intended to imply that features, elements or steps are in any way required for one or more embodiments or that one or more embodiments necessarily include logic for deciding, with or without other input or prompting, whether these features, elements or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, or Z). Thus, such disjunctive language is not generally intended to, and should not, imply that certain embodiments require at least one of X, at least one of Y, and at least one of Z to each be present.

While the above detailed description has shown, described, and pointed out novel features as applied to various embodiments, it can be understood that various omissions, substitutions, and changes in the form and details of the devices or algorithms illustrated can be made without departing from the scope of the disclosure. As can be recognized, certain embodiments described herein can be embodied within a form that does not provide all of the features and benefits set forth herein, as some features can be used or practiced separately from others. All changes which come within the meaning and range of equivalency of the claims are to be embraced within their scope.

What is claimed is:

1. A system for assessing or predicting wound status, the system comprising:
- at least one light detection element configured to collect light of at least a first wavelength after being reflected from a tissue region comprising a burn; and
- one or more processors in communication with the at least one light detection element and configured to:
  - receive a signal from the at least one light detection element, the signal representing light of the first wavelength reflected from the tissue region;
  - generate, based on the signal, an image having a plurality of pixels depicting the tissue region;
  - determine, based on the signal, a reflectance intensity value at the first wavelength for each pixel of at least a subset of the plurality of pixels;
  - determine, using at least one deep learning (DL) algorithm, a burn status corresponding to each pixel of the subset of pixels depicting the tissue region, wherein the burn status corresponds to necrosis of adnexal structures within at least a portion of the burn; and
  - generate a classified image based at least in part on the image and the determined burn status corresponding to each pixel of the subset of pixels depicting the tissue region.

2. The system of claim 1, wherein the classified image comprises pixels having different visual representations based on the burn status corresponding to each pixel.

3. The system of claim 1, wherein the one or more processors are further configured to cause a visual display of the classified image.

4. The system of claim 1, wherein the burn status corresponding to each pixel is selected from a non-healing burn status and a healing burn status.

5. The system of claim 1, wherein the burn status corresponding to each pixel is a status associated with burn depth.

6. The system of claim 5, wherein the burn status corresponding to each pixel is selected from a first degree burn status, a superficial second degree burn status, a deep second degree burn status, and a third degree burn status.

7. The system of claim 1, wherein determining the burn status corresponding to each pixel of the subset of pixels depicting the tissue region comprises identifying a percentage of necrotic adnexal structures within the at least a portion of the burn.

8. The system of claim 7, wherein a non-healing burn status corresponds to necrosis of greater than 50.0% of the adnexal structures.

9. The system of claim 7, wherein a non-healing burn status corresponds to necrosis of greater than 0.0% of the adnexal structures.

10. The system of claim 1, wherein the at least one DL algorithm comprises a convolutional neural network.

11. The system of claim 10, wherein the convolutional neural network comprises a SegNet.

12. The system of claim 1, wherein the at least one DL algorithm comprises an ensemble of a plurality of DL algorithms.

13. The system of claim 12, wherein the at least one DL algorithm comprises a weighted averaging ensemble.

14. The system of claim 12, wherein the at least one DL algorithm comprises a TPR ensemble.

15. The system of claim 1, wherein the at least one DL algorithm is trained using a wound database.

16. The system of claim 15, wherein the wound database comprises a burn database.

17. The system of claim 1, wherein the at least one DL algorithm is trained based at least in part on a plurality of ground truth masks, wherein at least some of the ground truth masks are generated based at least in part on the presence of necrotic adnexal structures in burn tissue biopsies.

18. The system of claim 1, wherein the one or more processors are further configured to determine, based at least in part on the burn status corresponding to each pixel of the subset of pixels depicting the tissue region, a predictive score associated with healing of the burn over a predetermined time interval following generation of the image.

19. The system of claim 18, wherein the predictive score corresponds to a probability of healing without surgery or skin grafting.

20. The system of claim 18, wherein the predetermined time interval is 21 days.

21. A method of detecting cellular viability or damage, collagen denaturation, damage to adnexal structures or adnexal structure necrosis and/or damage to blood vessels of a subject after a wound comprising:

selecting a subject having a wound;

imaging a region of the wound, using the system of claim 1;

evaluating the image using a DL algorithm trained with a wound, database;

displaying whether cells of the wound are viable or damaged, collagen is denatured, adnexal structures are damaged or necrotic and/or blood vessels are damaged within the imaged region of the wound; and providing a predictive score for healing of the wound, over a set time period of 21-30 days, without advanced care such as surgery or skin grafting.

22. The method of claim 21, wherein the damaged adnexal structures evaluated comprise hair follicles, sebaceous glands, apocrine glands and/or eccrine sweat glands.

23. The method of claim 21, wherein the cell viability or damage, collagen denaturation, damage to adnexal structures or adnexal structure necrosis and/or damage to blood vessels of the subject are evaluated in the papillary region of the skin.

24. The method of claim 21, wherein the cell viability or damage, collagen denaturation, damage to adnexal structures or adnexal structure necrosis and/or damage to blood vessels of the subject are evaluated in the reticular dermis of the skin.

25. The method of claim 21, wherein the cell viability or damage, collagen denaturation, damage to adnexal structures or adnexal structure necrosis and/or damage to blood vessels of the subject are evaluated deeper than the reticular dermis of the skin.

26. The method of claim 21, wherein hyalinized collagen or lack of detectable individual collagen fibers is detected.

27. The method of claim 21, wherein the cellular damage is cell swelling, cytoplasmic vacuolization, or nuclear pyknosis.

28. The method of claim 21, wherein when 50% or greater of the adnexual structures analyzed is identified as being damaged or necrotic, a predictive score of non-healing burn is provided and said subject is provided guidance to receive advanced care such as skin grafting or surgery or said subject is provided skin grafting or surgery.

29. The method of claim 21, wherein the DL algorithm was trained using stochastic gradient descent with a momentum optimizer and cross-entropy loss.

30. The method of claim 21, wherein the DL algorithm is selected from SegNet, SegNet with filter-bank regularization, SegNet with auxiliary loss, U-Net, Dilated fully connected neural network (dFCN), Averaging Ensemble, TPR-ensemble, or Weighted Averaging Ensemble.

31. The method of claim 21, wherein the DL algorithm is SegNet.

* * * * *